United States Patent
Winters et al.

(10) Patent No.: US 8,853,418 B2
(45) Date of Patent: Oct. 7, 2014

(54) CYCLOPENTYLPYRAZOLES AS N-TYPE CALCIUM CHANNEL BLOCKERS

(71) Applicant: Janssen Pharmaceutica NV, Beerse (BE)

(72) Inventors: Michael Winters, Morgantown, PA (US); Zhihua Sui, Piscataway, NJ (US); Christopher Flores, Lansdale, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/968,470

(22) Filed: Aug. 16, 2013

(65) Prior Publication Data

US 2014/0051660 A1  Feb. 20, 2014

Related U.S. Application Data

(60) Provisional application No. 61/683,775, filed on Aug. 16, 2012.

(51) Int. Cl.
| | | |
|---|---|---|
| *A61K 31/695* | (2006.01) | |
| *C07D 231/56* | (2006.01) | |
| *C07D 401/12* | (2006.01) | |
| *C07D 231/54* | (2006.01) | |
| *C07D 405/12* | (2006.01) | |
| *C07F 7/18* | (2006.01) | |
| *C07D 405/04* | (2006.01) | |
| *C07D 401/04* | (2006.01) | |
| *C07D 403/04* | (2006.01) | |
| *C07D 491/113* | (2006.01) | |
| *A61K 31/416* | (2006.01) | |

(52) U.S. Cl.
CPC ............ *C07D 231/54* (2013.01); *C07D 401/12* (2013.01); *C07D 405/12* (2013.01); *C07F 7/1856* (2013.01); *C07D 405/04* (2013.01); *C07D 401/04* (2013.01); *C07D 403/04* (2013.01); *C07D 491/113* (2013.01); *A61K 31/416* (2013.01)

USPC .......................................... 548/360.1; 514/63

(58) Field of Classification Search
CPC ..................................................... C07D 231/54
See application file for complete search history.

(56) References Cited

FOREIGN PATENT DOCUMENTS

WO   WO 98/22442 A2   5/1998

OTHER PUBLICATIONS

Alexi, X., J. Steroid Biochem. and Mol. Biol., 2009, vol. 117, pp. 159-167.*
International Search Report for Application No. PCT/US2013/055267 mailed Dec. 17, 2013.
Faidallah, H., et al., "Synthesis of Some Sulfonamides, Disubstituted Sulfonyluras or Thioureas and Some Structurally Related Variants. A Class of Promising Antitumor Agent"., Medical Chemistry Research, vol. 16, No. 1, pp. 300-318 (2007).

* cited by examiner

*Primary Examiner* — Heidi Reese
(74) *Attorney, Agent, or Firm* — Peter L. Herridge

(57) ABSTRACT

Disclosed are compounds, compositions and methods for treating various diseases, syndromes, conditions and disorders, including pain. Such compounds are represented by Formula (I) as follows:

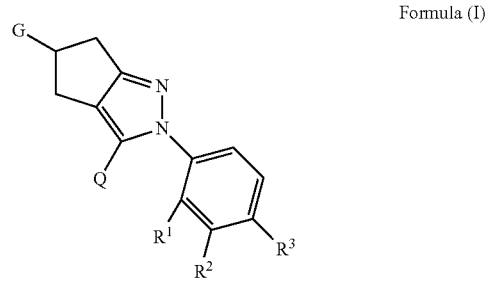

Formula (I)

wherein $R^1$, $R^2$, $R^3$, Q, and G are defined herein.

21 Claims, 1 Drawing Sheet

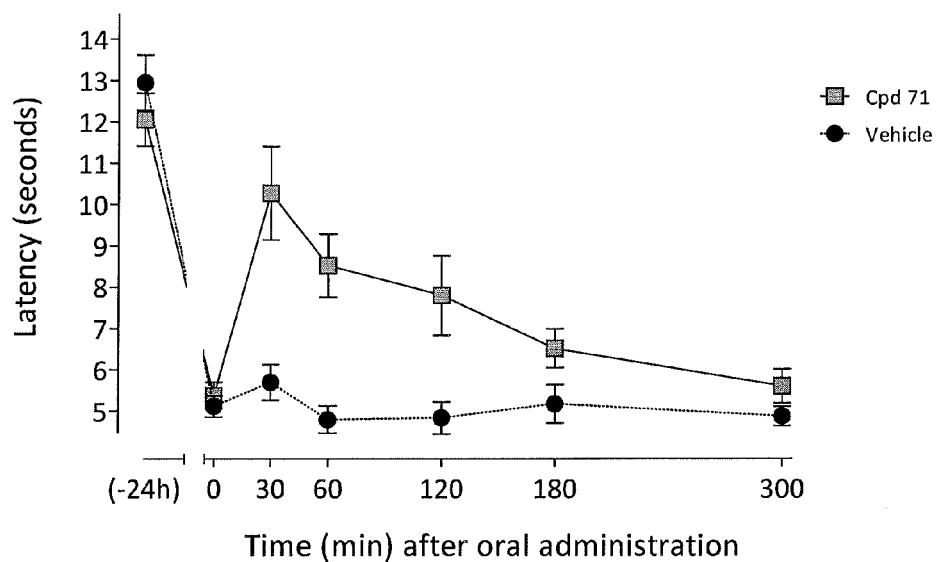

CYCLOPENTYLPYRAZOLES AS N-TYPE CALCIUM CHANNEL BLOCKERS

CROSS REFERENCE TO RELATED APPLICATIONS

This application claims priority of the benefits of the filing of U.S. Provisional Application Ser. No. 61/683,775, filed Aug. 16, 2012. The complete disclosures of the aforementioned related U.S. patent application is/are hereby incorporated herein by reference for all purposes.

STATEMENT REGARDING FEDERALLY SPONSORED RESEARCH OR DEVELOPMENT

The research and development of the invention described below was not federally sponsored.

BACKGROUND OF THE INVENTION

Calcium ions play a fundamental role in the physiology and biochemistry of organisms and of cells. The entry of calcium into cells through ion channels mediates a variety of cellular and physiological responses, including gene expression, signal transduction, neurotransmitter release, muscle contraction and hormone secretion. Ion channels are classified by gating, or what opens and closes the channel to the flux of ions. Voltage-gated ion channels open or close depending on the voltage gradient across the plasma membrane, whereas ligand-gated ion channels open or close depending on the binding of ligands to the channel. The classification of voltage-gated calcium channels divides them into three groups: (i) high voltage-activated channels, which include L-, N-, P- and Q-type channels; (ii) intermediate voltage-activated R-type channels; and (iii) low voltage-activated T-type channels.

The N-type calcium channel is distributed mainly in central and peripheral neurons, being localized primarily to presynaptic nerve terminals. This channel regulates the calcium flux required for depolarization-evoked release of neurotransmitters from synaptic endings. The transmission of pain signals from the periphery to the central nervous system (CNS) is mediated, inter alia, by N-type calcium channels located in the spinal cord. Inhibition of the N-type calcium channel in the superficial dorsal horn leads to a decrease in membrane excitability and neurotransmitter release, resulting in pain relief. In addition, knock-out mice lacking the N-type calcium channel exhibit reduced nociceptive behaviors in animal models of pain.

N-type calcium channels have been shown to mediate the development and maintenance of the neuronal sensitization processes associated with neuropathic pain and therefore provide attractive targets for the development of analgesic drugs. Three N-type calcium channel modulators are currently approved for the treatment of pain: ω-conotoxin MVIIA (ziconotide), marketed as Prialt®, potently and selectively blocks the N-type calcium channel and is indicated for the management of severe chronic pain; gabapentin, marketed as Neurontin®, and pregabalin, marketed as Lyrica®, bind with high affinity to the α2δ subunit of the N-type calcium channel and are indicated for the treatment of fibromyalgia, diabetic nerve pain and/or post-herpetic neuralgia pain.

It is an object of the present invention to provide N-Type calcium channel blockers. It is also an object of the invention to provide a method of treating, ameliorating or preventing pain by the administration of a compound of Formula (I). And, it is an object of the invention to provide a pharmaceutical composition comprising a compound of Formula (I), useful for treating, ameliorating or preventing pain.

SUMMARY OF THE INVENTION

The present invention is directed to a compound of Formula (I)

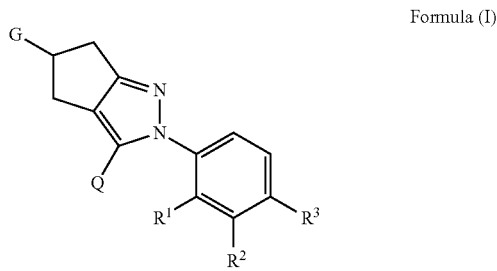

Formula (I)

wherein $R^1$ is selected from the group consisting of $C_{1-4}$alkyl, $C_{1-4}$alkoxy, trifluoromethoxy, and trifluoromethyl;

$R^2$ is hydrogen; or, $R^2$ may be taken with $R^1$ and the phenyl ring to which $R^1$ and $R^2$ are both attached to form 2,3-dihydrobenzofuran-7-yl;

$R^3$ is hydrogen, chloro, or fluoro;

Q is selected from the group consisting of Q1, Q2, and Q3;

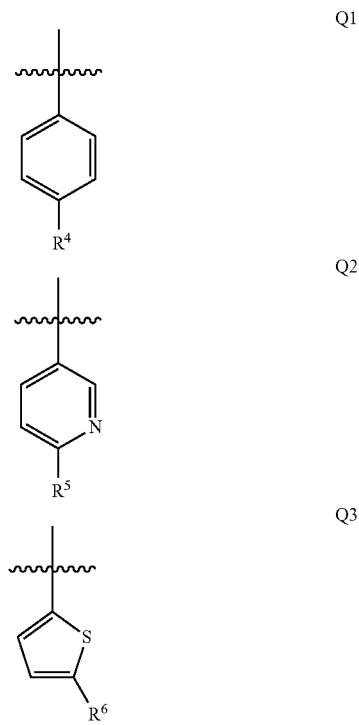

wherein $R^4$ is selected from the group consisting of hydrogen, $C_{1-4}$alkyl, $C_{1-4}$alkoxy, cyano, fluoro, chloro, hydroxy, di($C_{1-4}$alkyl)amino, ($C_{1-4}$alkyl)amino, amino, $C_{1-4}$alkylcarbonyl, and $C_{1-4}$alkylsulfonyl;

$R^5$ and $R^6$ are each independently selected from the group consisting of hydrogen, $C_{1-4}$alkyl, $C_{1-4}$alkoxy, cyano, chloro, and di($C_{1-4}$alkyl)amino;

G is selected from the group consisting of $C_{1-6}$alkyl, hydroxy($C_{1-4}$)alkyl, $C_{1-6}$alkoxy, hydroxy, allyl, 2-methyl-prop-1-enyl, cyano, oxime, phenoxy, $C_{1-4}$alkoxycarbonyl, $C_{3-6}$cycloalkyl, 4,4-dimethyl-cyclohexyl, $C_{3-6}$cycloalkyl($C_{1-4}$alkyl, $C_{3-6}$cycloalkyloxy, $C_{1-6}$alkylcarbonyloxy, di($C_{1-4}$alkyl)aminocarbonyloxy, di($C_{1-4}$alkyl)aminocarbonyloxy-$C_{1-4}$alkyl, $C_{1-4}$alkoxycarbonylamino-$C_{1-4}$alkyl, $C_{3-6}$cycloalkyl($C_{1-4}$)alkoxy, $C_{3-6}$cycloalkylcarbonyloxy, di($C_{1-4}$alkyl)aminosulfonyl-amino, di($C_{1-4}$alkyl)aminosulfonyl-(N-methyl)amino, $C_{1-4}$alkylsulfonyl-(N-methyl)amino, $C_{1-4}$alkylsulfonylamino, $C_{1-4}$alkylsulfonylamino-$C_{1-4}$alkyl, $C_{1-4}$alkylcarbonylamino-$C_{1-4}$alkyl, di($C_{1-4}$alkyl)aminocarbonylamino-$C_{1-4}$alkyl, trifluoromethylcarbonylamino, trifluoromethylcarbonylamino-$C_{1-4}$alkyl, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-$C_{1-4}$alkyl, 6-(morpholin-4-yl)-pyrimidin-3-yl, 4-methyl-piperidin-1-yl, (1,2,4)-bicyclo[2.2.1]heptan-2-yloxy, tetrahydro-2H-pyran-4-ylcarbonyloxy, tetrahydro-2H-pyran-4-yl($C_{1-4}$alkoxy, 1,2,3,4-tetrahydroquinolin-3-yl, aminocarbonyl, pyridin-3-yl optionally substituted with one to two substituents each independently selected from the group consisting of $C_{1-4}$alkyl, $C_{1-4}$alkoxy, chloro, cyclopropyl, morpholin-4-yl, and $C_{1-4}$alkoxycarbonyl;

1H-1,2,3-triazol-1-yl optionally substituted with one to two substituents each independently selected from the group consisting of $C_{1-4}$alkyl, 2-hydroxypropan-2-yl, methoxymethyl, $C_{3-6}$cycloalkyl, $C_{1-4}$alkoxycarbonyl, $C_{1-4}$alkylcarbonyloxy-$C_{1-4}$alkyl, and trimethylsilyl;

1H-imidazol-1-yl optionally independently substituted with one to three $C_{1-3}$alkyl substituents;

and a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;

provided that a compound of Formula (I) is other than
N-[3-(4-chlorophenyl)-2-(2-methoxyphenyl)-2,4,5,6-tetrahydrocyclopenta[c]pyrazol-5-yl]-N,N',N'-trimethylsulfamide; or
3-(4-chlorophenyl)-2-(2-methoxyphenyl)-4',4',5',5'-tetramethyl-2,6-dihydro-4H-spiro[cyclopenta[c]pyrazole-5,2'-[1,3]dioxolane];
and enantiomers, diastereomers, solvates and pharmaceutically acceptable salts thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent, and a compound of Formula (I), or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides, inter alia, methods for treating or ameliorating a N-Type calcium channel-modulated disorder in a subject, including a human or other mammal in which the disease, syndrome, or condition is affected by the modulation of the N-Type calcium channel, such as pain and the diseases that lead to such pain, using a compound of Formula (I).

The present invention also provides, inter alia, methods for producing the instant compounds and pharmaceutical compositions and medicaments thereof.

BRIEF DESCRIPTION OF THE DRAWINGS

FIG. 1 shows the antihyperalgesic effect of Compound 71 in a rat CFA radiant heat model of inflammatory pain.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g. $C_{1-8}$) refer independently to the number of carbon atoms in an alkyl moiety or to the alkyl portion of a larger alkyl-containing substituent. In substituent groups with multiple alkyl groups such as ($C_{1-6}$alkyl)$_2$-amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl and adamantyl.

The term "benzo-fused cycloalkyl" refers to a 5- to 8-membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members and which contains carbon atoms and from 1 to 4 heteroatoms independently selected from the group consisting of N, O, and S. Included within the term heterocyclyl is a nonaromatic cyclic ring of 5 to 7 members in which 1 to 2 members are nitrogen, or a nonaromatic cyclic ring of 5 to 7 members in which 0, 1 or 2 members are nitrogen and up to 2 members are oxygen or sulfur and at least one member must be either nitrogen, oxygen or sulfur; wherein, optionally, the ring contains zero to one unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from the group consisting of N, O, and S. The carbon atom ring members that form the heterocycle ring may be fully saturated or partially saturated. Unless otherwise noted, benzo-fused heterocycle ring is attached to its pendant group at a carbon atom of the benzene ring.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine.

The term "formyl" refers to the group —C(=O)H.

The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

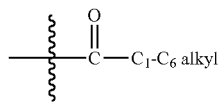

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I) can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "N-Type calcium channel blocker" is intended to encompass a compound that interacts with the N-Type calcium channel to substantially reduce or eliminate its functional activity, thereby decreasing the flow of calcium ions through the channel and the rise of intracellular calcium concentrations.

The term "N-Type calcium channel-modulated" is used to refer to the condition of being affected by the modulation of the N-Type calcium channel, including the condition of being affected by the inhibition of the N-Type calcium channel, such as, for example, pain, the diseases that lead to such pain and treatments that lead to the reduction of such pain.

As used herein, unless otherwise noted, the term "affect" or "affected" (when referring to a disease, syndrome, condition or disorder that is affected by the inhibition of N-Type calcium channel) shall include a reduction in the frequency and/or severity of one or more symptoms or manifestations of said disease, syndrome, condition or disorder and/or include the prevention of the development of one or more symptoms or manifestations of said disease, syndrome, condition or disorder or the development of the disease, condition, syndrome or disorder.

The compounds of Formula (I) are useful in methods for treating, ameliorating and/or preventing a disease, a syndrome, a condition or a disorder that is affected by the inhibition of N-Type calcium channel. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt form thereof. In particular, the compounds of Formula (I) are useful for treating, ameliorating and/or preventing pain as well as diseases, syndromes, conditions or disorders causing such pain. More particularly, the compounds of Formula (I) are useful for treating, ameliorating and/or preventing acute pain, inflammatory pain and/or neuropathic pain, comprising administering to a subject in need thereof a therapeutically effective amount of a compound of Formula (I), as herein defined.

Acute pain, as used herein, refers to pain that comes on quickly, can be of varying severity but is self-limiting and of relatively short duration. Examples of acute pain include, but are not limited to, post-operative pain, post-surgical pain, toothache, burn, sunburn, insect/animal bites and stings, headache and/or any pain associated with acute trauma or injury.

Inflammatory pain refers to pain arising from an inflammatory disease, condition, syndrome or disorder, including but not limited to inflammatory bowel disease, irritable bowel syndrome, visceral pain, migraine, post-operative pain, osteoarthritis, rheumatoid arthritis, back pain, low back pain, joint pain, abdominal pain, chest pain, labor pain, musculoskeletal diseases, skin diseases, toothache, pyresis, burn, sunburn, snake bite, venomous snake bite, spider bite, insect sting, neurogenic or overactive bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache or arachnoiditis.

A further embodiment of the present invention is directed to a method for treating, ameliorating and/or preventing neuropathic pain. Neuropathic pain refers to a disease, syndrome, condition and/or disorder involving damage to the peripheral or central nervous system, including cancer pain, neurological disorders, spine and peripheral nerve surgery, brain tumor, traumatic brain injury (TBI), chemotherapy-induced pain, pain chronification, radicular pain, HIV pain, spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, post-herpetic neuralgia, causalgia, red neuralgia, Sluder's neuralgia, splenopalatine neuralgia, supraorbital neuralgia, trigeminal neuralgia, vulvodynia, or vidian neuralgia.

Embodiments of the present invention include a compound of Formula (I)

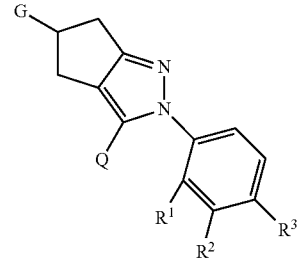

Formula (I)

wherein
a) $R^1$ is selected from the group consisting of $C_{1-4}$alkyl, $C_{1-4}$alkoxy, and trifluoromethoxy;
b) $R^1$ is selected from the group consisting of $C_{1-4}$alkoxy, and trifluoromethoxy;
c) $R^2$ is hydrogen;
d) $R^3$ is hydrogen or chloro;
e) $R^3$ is hydrogen;
f) $R^4$ is selected from the group consisting of $C_{1-4}$alkyl, $C_{1-4}$alkoxy, cyano, chloro, and di($C_{1-4}$alkyl)amino;
g) $R^6$ is chloro;
h) G is selected from the group consisting of $C_{1-6}$alkyl, hydroxy($C_{1-4}$)alkyl, $C_{1-6}$alkoxy, 2-methylprop-1-enyl, cyano, phenoxy, $C_{1-4}$alkoxycarbonyl, $C_{3-6}$cycloalkyl, 4,4-dimethyl-cyclohexyl, $C_{3-6}$cycloalkyl($C_{1-4}$)alkyl, $C_{3-6}$cycloalkyloxy, $C_{1-6}$alkylcarbonyloxy, di($C_{1-4}$alkyl)aminocarbonyloxy, di($C_{1-4}$alkyl)aminocarbonyloxy-$C_{1-4}$alkyl, $C_{1-4}$alkoxycarbonylamino-$C_{1-4}$alkyl, $C_{3-6}$cycloalkyl($C_{1-4}$)alkoxy, $C_{3-6}$cycloalkylcarbonyloxy, di($C_{1-4}$alkyl)aminosulfonyl-amino, di($C_{1-4}$alkyl)aminosulfonyl-(N-methyl)amino, $C_{1-4}$alkylsulfonyl-(N-methyl)amino, $C_{1-4}$alkylsulfonylamino, $C_{1-4}$alkylsulfonylamino-$C_{1-4}$alkyl, $C_{1-4}$alkylcarbonylamino-$C_{1-4}$alkyl, di($C_{1-4}$alkyl)aminocarbonylamino-$C_{1-4}$alkyl, trifluoromethylcarbonylamino, trifluoromethylcarbonylamino-$C_{1-4}$alkyl, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-$C_{1-4}$alkyl, 4-methyl-piperidin-1-yl, (1,2,4)-bicyclo[2.2.1]heptan-2-yloxy, tetrahydro-2H-pyran-4-yl($C_{1-4}$)alkoxy, 1,2,3,4-tetrahydroquinolin-3-yl, aminocarbonyl,
pyridin-3-yl optionally substituted with one to two substituents each independently selected from the group consisting of C$_{1-4}$alkyl, C$_{1-4}$alkoxy, chloro, cyclopropyl, and C$_{1-4}$alkoxycarbonyl;

1H-1,2,3-triazol-1-yl optionally substituted with one to two substituents each independently selected from the group consisting of C$_{1-4}$alkyl, C$_{3-6}$-cycloalkyl, C$_{1-4}$alkoxycarbonyl, C$_{1-4}$alkylcarbonyloxy-C$_{1-4}$ alkyl, and trimethylsilyl;

1H-imidazol-1-yl optionally independently substituted with one to three C$_{1-3}$alkyl substituents;

and a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;

i) G is selected from the group consisting of C$_{1-6}$alkyl, C$_{1-6}$alkoxy, C$_{1-6}$alkoxycarbonyl, C$_{3-6}$cycloalkyloxy, C$_{1-6}$alkylcarbonyloxy, di(C$_{1-4}$alkyl)aminocarbonyloxy, di(C$_{1-4}$alkyl)aminocarbonyloxy-C$_{1-4}$alkyl, C$_{1-4}$alkoxycarbonylamino-C$_{1-4}$alkyl, C$_{3-6}$cycloalkyl(C$_{1-4}$alkoxy, C$_{3-6}$cycloalkylcarbonyloxy, di(C$_{1-4}$alkyl)aminosulfonyl-amino, di(C$_{1-4}$alkyl)aminosulfonyl-(N-methyl)amino, C$_{1-4}$alkylsulfonyl-(N-methyl)amino, C$_{1-4}$alkylsulfonylamino, C$_{1-4}$alkylsulfonylamino-C$_{1-4}$alkyl, C$_{1-4}$alkylcarbonylamino-C$_{1-4}$alkyl, trifluoromethylcarbonylamino, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-C$_{1-4}$alkyl, 4-methyl-piperidin-1-yl, (1,2,4)-bicyclo[2.2.1]heptan-2-yloxy, tetrahydro-2H-pyran-4-yl(C$_{1-4}$)alkoxy, pyridin-3-yl optionally substituted with a substituent independently selected from the group consisting of C$_{1-4}$alkyl, cyclopropyl, and C$_{1-4}$alkoxycarbonyl;

1H-1,2,3-triazol-1-yl optionally substituted with one to two substituents each independently selected from the group consisting of C$_{1-4}$alkyl, C$_{3-6}$-cycloalkyl, C$_{1-4}$alkoxycarbonyl, and trimethylsilyl;

1H-imidazol-1-yl optionally independently substituted with one to three C$_{1-3}$alkyl substituents;

and a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;

and any combination of embodiments a) through i) above, provided that it is understood that combinations in which different embodiments of the same substituent would be combined are excluded;

and enantiomers, diastereomers, solvates and pharmaceutically acceptable salts thereof.

An embodiment of the present invention is directed to a compound of Formula (I)

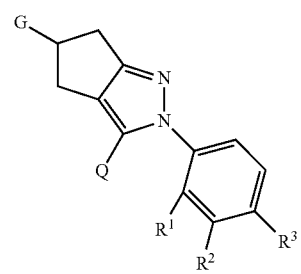

Formula (I)

wherein

R$^1$ is selected from the group consisting of C$_{1-4}$alkyl, C$_{1-4}$alkoxy, and trifluoromethoxy;

R$^2$ is hydrogen; or, R$^2$ may be taken with R$^1$ and the phenyl ring to which R$^1$ and R$^2$ are both attached to form 2,3-dihydrobenzofuran-7-yl;

R$^3$ is hydrogen or chloro;

Q is selected from the group consisting of Q1, Q2, and Q3;

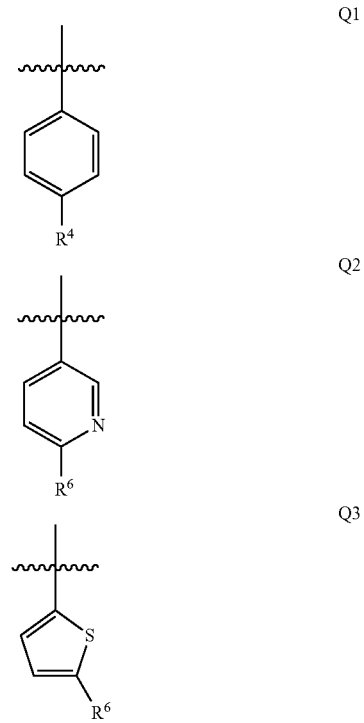

R$^4$ is selected from the group consisting of C$_{1-4}$alkyl, C$_{1-4}$alkoxy, cyano, chloro, and di(C$_{1-4}$alkyl)amino;

R$^5$ and R$^6$ are each independently selected from the group consisting of C$_{1-4}$alkyl, C$_{1-4}$alkoxy, cyano, chloro, and di(C$_{1-4}$alkyl)amino;

G is selected from the group consisting of C$_{1-6}$alkyl, hydroxy(C$_{1-4}$)alkyl, C$_{1-6}$alkoxy, 2-methylprop-1-enyl, cyano, phenoxy, C$_{1-4}$alkoxycarbonyl, C$_{3-6}$cycloalkyl, 4,4-dimethyl-cyclohexyl, C$_{3-6}$cycloalkyl(C$_{1-4}$)alkyl, C$_{3-6}$cycloalkyloxy, C$_{1-6}$alkylcarbonyloxy, di(C$_{1-4}$alkyl)aminocarbonyloxy, di(C$_{1-4}$alkyl)aminocarbonyloxy-C$_{1-4}$alkyl, C$_{1-4}$alkoxycarbonylamino-C$_{1-4}$alkyl, C$_{3-6}$cycloalkyl(C$_{1-4}$) alkoxy, C$_{3-6}$cycloalkylcarbonyloxy, di(C$_{1-4}$alkyl)aminosulfonyl-amino, di(C$_{1-4}$alkyl)aminosulfonyl-(N-methyl)amino, C$_{1-4}$alkylsulfonyl-(N-methyl)amino, C$_{1-4}$alkylsulfonylamino, C₁₋₄alkylsulfonylamino-C₁₋₄alkyl, C₁₋₄alkylcarbonylamino-C₁₋₄alkyl, di(C₁₋₄alkyl)aminocarbonylamino-C₁₋₄alkyl, trifluoromethylcarbonylamino, trifluoromethylcarbonylamino-C₁₋₄alkyl, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-C₁₋₄alkyl, 4-methyl-piperidin-1-yl, (1,2,4)-bicyclo[2.2.1]heptan-2-yloxy, tetrahydro-2H-pyran-4-yl(C₁₋₄alkoxy, 1,2,3,4-tetrahydroquinolin-3-yl, aminocarbonyl, pyridin-3-yl optionally substituted with morpholin-4-yl or one to two substituents each independently selected from the group consisting of C₁₋₄alkyl, C₁₋₄alkoxy, chloro, cyclopropyl, and C₁₋₄alkoxycarbonyl;

1H-1,2,3-triazol-1-yl optionally substituted with one to two substituents each independently selected from the group consisting of C₁₋₄alkyl, C₃₋₆cycloalkyl, C₁₋₄-alkoxycarbonyl, C₁₋₄alkylcarbonyloxy-C₁₋₄alkyl, and trimethylsilyl;

1H-imidazol-1-yl optionally independently substituted with one to three C₁₋₃alkyl substituents;

and a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;

provided that a compound of Formula (I) is other than

N-[3-(4-chlorophenyl)-2-(2-methoxyphenyl)-2,4,5,6-tetrahydrocyclopenta[c]pyrazol-5-yl]-N,N',N'-trimethylsulfamide; or 3-(4-chlorophenyl)-2-(2-methoxyphenyl)-4',4',5',5'-tetramethyl-2,6-dihydro-4H-spiro[cyclopenta[c]pyrazole-5,2'-[1,3]dioxolane];

and enantiomers, diastereomers, solvates and pharmaceutically acceptable salts thereof.

An embodiment of the present invention is directed to a compound of Formula (I)

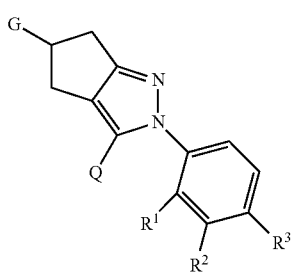

Formula (I)

wherein

R¹ is selected from the group consisting of C₁₋₄alkyl, C₁₋₄alkoxy, and trifluoromethoxy;

R² is hydrogen; or, R² may be taken with R¹ and the phenyl ring to which R¹ and R² are both attached to form 2,3-dihydrobenzofuran-7-yl;

R³ is hydrogen;

Q is selected from the group consisting of Q1, Q2, and Q3;

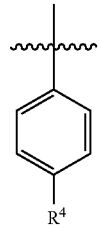

Q1

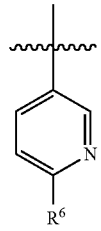

Q2

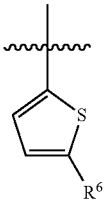

Q3

R⁴ is selected from the group consisting of C₁₋₄alkyl, C₁₋₄alkoxy, cyano, chloro, and di(C₁₋₄alkyl)amino;

R⁵ is selected from the group consisting of C₁₋₄alkyl, C₁₋₄alkoxy, cyano, chloro, and di(C₁₋₄alkyl)amino;

R⁶ is chloro;

G is selected from the group consisting of C₁₋₆alkyl, hydroxy(C₁₋₄)alkyl, C₁₋₆alkoxy, 2-methylprop-1-enyl, cyano, phenoxy, C₁₋₄alkoxycarbonyl, C₃₋₆cycloalkyl, 4,4-dimethyl-cyclohexyl, C₃₋₆cycloalkyl(C₁₋₄)alkyl, C₃₋₆cycloalkyloxy, C₁₋₆alkylcarbonyloxy, di(C₁₋₄alkyl)aminocarbonyloxy, di(C₁₋₄alkyl)aminocarbonyloxy-C₁₋₄alkyl, C₁₋₄alkoxycarbonylamino-C₁₋₄alkyl, C₃₋₆cycloalkyl(C₁₋₄) alkoxy, C₃₋₆cycloalkylcarbonyloxy, di(C₁₋₄alkyl)aminosulfonyl-amino, di(C₁₋₄alkyl)aminosulfonyl-(N-methyl)amino, C₁₋₄alkylsulfonyl-(N-methyl)amino, C₁₋₄alkylsulfonylamino, C₁₋₄alkylsulfonylamino-C₁₋₄alkyl, C₁₋₄alkylcarbonylamino-C₁₋₄alkyl, di(C₁₋₄alkyl)aminocarbonylamino-C₁₋₄alkyl, trifluoromethylcarbonylamino, trifluoromethylcarbonylamino-C₁₋₄alkyl, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-C₁₋₄alkyl, 4-methyl-piperidin-1-yl, (1,2,4)-bicyclo[2.2.1]heptan-2-yloxy, tetrahydro-2H-pyran-4-yl(C₁₋₄)alkoxy, 1,2,3,4-tetrahydroquinolin-3-yl, aminocarbonyl, pyridin-3-yl optionally substituted with one to two substituents each independently selected from the group consisting of C₁₋₄alkyl, C₁₋₄alkoxy, chloro, cyclopropyl, and C₁₋₄alkoxycarbonyl;

1H-1,2,3-triazol-1-yl optionally substituted with one to two substituents each independently selected from the group consisting of C₁₋₄alkyl, C₃₋₆cycloalkyl, C₁₋₄alkoxycarbonyl, C₁₋₄alkylcarbonyloxy-C₁₋₄alkyl, and trimethylsilyl;

1H-imidazol-1-yl optionally independently substituted with one to three C₁₋₃alkyl substituents;

and a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;

provided that a compound of Formula (I) is other than

N-[3-(4-chlorophenyl)-2-(2-methoxyphenyl)-2,4,5,6-tetrahydrocyclopenta[c]pyrazol-5-yl]-N,N',N'-trimethylsulfamide; or 3-(4-chlorophenyl)-2-(2-methoxyphenyl)-4',4',5',5'-tetramethyl-2,6-dihydro-4H-spiro[cyclopenta[c]pyrazole-5,2'-[1,3]dioxolane];

and enantiomers, diastereomers, solvates and pharmaceutically acceptable salts thereof.

An embodiment of the present invention is directed to a compound of Formula (I)

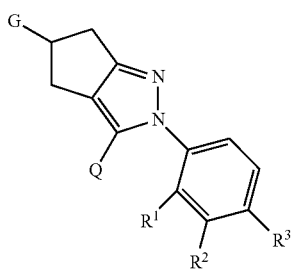

Formula (I)

wherein $R^1$ is selected from the group consisting of $C_{1-4}$alkoxy and trifluoromethoxy;

$R^2$ is hydrogen;

$R^3$ is hydrogen;

Q is selected from the group consisting of Q1, Q2, and Q3;

Q1

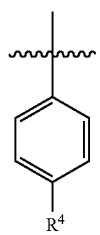

Q2

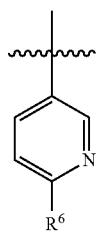

Q3

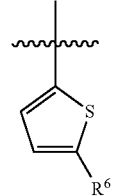

$R^4$ is selected from the group consisting of $C_{1-4}$alkyl, $C_{1-4}$alkoxy, cyano, chloro, and di($C_{1-4}$alkyl)amino;

$R^5$ is selected from the group consisting of $C_{1-4}$alkyl, $C_{1-4}$alkoxy, cyano, chloro, and di($C_{1-4}$alkyl)amino;

$R^6$ is chloro;

G is selected from the group consisting of $C_{1-6}$alkyl, $C_{1-6}$alkoxy, $C_{1-4}$alkoxycarbonyl, $C_{3-6}$cycloalkyloxy, $C_{1-6}$alkylcarbonyloxy, di($C_{1-4}$alkyl)aminocarbonyloxy, di($C_{1-4}$alkyl)aminocarbonyloxy-$C_{1-4}$alkyl, $C_{1-4}$alkoxycarbonylamino-$C_{1-4}$alkyl, $C_{3-6}$cycloalkyl($C_{1-4}$alkoxy, $C_{3-6}$cycloalkylcarbonyloxy, di($C_{1-4}$alkyl)aminosulfonyl-amino, di($C_{1-4}$alkyl)aminosulfonyl-(N-methyl)amino, $C_{1-4}$alkylsulfonyl-(N-methyl)amino, $C_{1-4}$alkylsulfonylamino, $C_{1-4}$alkylsulfonylamino-$C_{1-4}$alkyl, $C_{1-4}$alkylcarbonylamino-$C_{1-4}$alkyl, trifluoromethylcarbonylamino, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-$C_{1-4}$alkyl, 4-methyl-piperidin-1-yl, (1,2,4)-bicyclo[2.2.1]heptan-2-yloxy, tetrahydro-2H-pyran-4-yl($C_{1-4}$alkoxy, pyridin-3-yl optionally substituted with a substituent independently selected from the group consisting of $C_{1-4}$alkyl, cyclopropyl, and $C_{1-4}$alkoxycarbonyl;

1H-1,2,3-triazol-1-yl optionally substituted with one to two substituents each independently selected from the group consisting of $C_{1-4}$alkyl, $C_{3-6}$cycloalkyl, $C_{1-4}$alkoxycarbonyl, and trimethylsilyl;

1H-imidazol-1-yl optionally independently substituted with one to three $C_{1-3}$alkyl substituents;

and a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;

provided that a compound of Formula (I) is other than

N-[3-(4-chlorophenyl)-2-(2-methoxyphenyl)-2,4,5,6-tetrahydrocyclopenta[c]pyrazol-5-yl]-N,N',N'-trimethylsulfamide; or 3-(4-chlorophenyl)-2-(2-methoxyphenyl)-4',4',5',5'-tetramethyl-2,6-dihydro-4H-spiro[cyclopenta[c]pyrazole-5,2'-[1,3]dioxolane];

and enantiomers, diastereomers, solvates and pharmaceutically acceptable salts thereof.

Further embodiments of the present invention are directed to a compound of Formula (I)

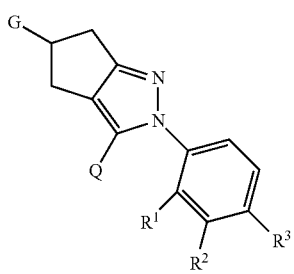

Formula (I)

selected from the group consisting of

2-[3-(4-chlorophenyl)-2-(2-methoxyphenyl)-2,4,5,6-tetrahydrocyclopenta[c]pyrazol-5-yl]ethanol;
2-[3-(4-chlorophenyl)-2-(2-methoxyphenyl)-2,4,5,6-tetrahydrocyclopenta[c]pyrazol-5-yl]ethyl morpholine-4-carboxylate;
2-[3-(4-chlorophenyl)-2-(2-methoxyphenyl)-2,4,5,6-tetrahydrocyclopenta[c]pyrazol-5-yl]ethyl dimethylcarbamate;
3-(4-chlorophenyl)-2-(2-methoxyphenyl)-5-prop-2-en-1-yl-2,4,5,6-tetrahydrocyclopenta[c]pyrazole;
ethyl 3-(4-chlorophenyl)-2-(2-methoxyphenyl)-2,4,5,6-tetrahydrocyclopenta[c]pyrazole-5-carboxylate;
3-(4-chlorophenyl)-2-(2-methoxyphenyl)-2,4,5,6-tetrahydrocyclopenta[c]pyrazole-5-carboxamide;
N-{[2-(2-methoxyphenyl)-3-phenyl-2,4,5,6-tetrahydrocyclopenta[c]pyrazol-5-yl]methyl}methanesulfonamide;
N-{[3-(4-chlorophenyl)-2-(2-methoxyphenyl)-2,4,5,6-tetrahydrocyclopenta[c]pyrazol-5-yl]methyl}methanesulfonamide;
2-(2-methoxyphenyl)-3-phenyl-2,4,5,6-tetrahydrocyclopenta[c]pyrazole-5-carbonitrile;
3-(4-chlorophenyl)-2-(2-methoxyphenyl)-2,4,5,6-tetrahydrocyclopenta[c]pyrazole-5-carbonitrile;
N-{2-[3-(4-chlorophenyl)-2-(2-methoxyphenyl)-2,4,5,6-tetrahydrocyclopenta[c]pyrazol-5-yl]ethyl}methanesulfonamide;
N-{2-[3-(4-chlorophenyl)-2-(2-methoxyphenyl)-2,4,5,6-tetrahydrocyclopenta[c]pyrazol-5-yl]ethyl}acetamide;
tert-butyl{2-[3-(4-chlorophenyl)-2-(2-methoxyphenyl)-2,4,5,6-tetrahydrocyclopenta[c]pyrazol-5-yl]ethyl}carbamate;
ethyl 3-(4-chlorophenyl)-2-(2-ethylphenyl)-2,4,5,6-tetrahydrocyclopenta[c]pyrazole-5-carboxylate;
tert-butyl{[3-(4-chlorophenyl)-2-(2-ethylphenyl)-2,4,5,6-tetrahydrocyclopenta[c]pyrazol-5-yl]methylidene}carbamate;
tert-butyl{[3-(4-chlorophenyl)-2-(2-ethylphenyl)-2,4,5,6-tetrahydrocyclopenta[c]pyrazol-5-yl]methyl}carbamate;
[3-(4-chlorophenyl)-2-(2-ethylphenyl)-2,4,5,6-tetrahydrocyclopenta[c]pyrazol-5-yl]methyl diethylcarbamate;
N-{[3-(4-chlorophenyl)-2-(2-ethylphenyl)-2,4,5,6-tetrahydrocyclopenta[c]pyrazol-5-yl]methyl}methanesulfonamide;
N-{[3-(4-chlorophenyl)-2-(2-ethylphenyl)-2,4,5,6-tetrahydrocyclopenta[c]pyrazol-5-yl]methyl}-2,2,2-trifluoroacetamide;
tert-butyl(2-{3-(4-chlorophenyl)-2-[2-(trifluoromethyl)phenyl]-2,4,5,6-tetrahydrocyclopenta[c]pyrazol-5-yl}ethyl)carbamate;
N-(2-{3-(4-chlorophenyl)-2-[2-(trifluoromethyl)phenyl]-2,4,5,6-tetrahydrocyclopenta[c]pyrazol-5-yl}ethyl)methanesulfonamide;
3-(2-{3-(4-chlorophenyl)-2-[2-(trifluoromethyl)phenyl]-2,4,5,6-tetrahydrocyclopenta[c]pyrazol-5-yl}ethyl)-1,1-dimethylurea;
3-(4-chlorophenyl)-2-[2-(trifluoromethoxy)phenyl]-2,4,5,6-tetrahydrocyclopenta[c]pyrazol-5-yl dimethylcarbamate;
3-(4-chlorophenyl)-2-[2-(trifluoromethoxy)phenyl]-2,4,5,6-tetrahydrocyclopenta[c]pyrazol-5-ylmorpholine-4-carboxylate;
3-(4-chlorophenyl)-2-[2-(trifluoromethoxy)phenyl]-2,4,5,6-tetrahydrocyclopenta[c]pyrazol-5-ol;
3-(4-chlorophenyl)-2-(2-methoxyphenyl)-2,4,5,6-tetrahydrocyclopenta[c]pyrazol-5-ol;
3-(4-chlorophenyl)-2-[2-(trifluoromethoxy)phenyl]-2,6-dihydrocyclopenta[c]pyrazol-5(4H)-one;
3-(4-chlorophenyl)-2-(2-methoxyphenyl)-2,4,5,6-tetrahydrocyclopenta[c]pyrazol-5-yl dimethylcarbamate;
3-(4-chlorophenyl)-2-(2-methoxyphenyl)-2,4,5,6-tetrahydrocyclopenta[c]pyrazol-5-yl morpholine-4-carboxylate;
3-(4-chlorophenyl)-2-(2-ethoxyphenyl)-2,4,5,6-tetrahydrocyclopenta[c]pyrazol-5-yl dimethylcarbamate;
3-(4-chlorophenyl)-2-(2-ethoxyphenyl)-2,4,5,6-tetrahydrocyclopenta[c]pyrazol-5-yl morpholine-4-carboxylate;
N-[3-(4-chlorophenyl)-2-(2-methoxyphenyl)-2,4,5,6-tetrahydrocyclopenta[c]pyrazol-5-yl]methanesulfonamide;
N-[3-(4-chlorophenyl)-2-(2-methoxyphenyl)-2,4,5,6-tetrahydrocyclopenta[c]pyrazol-5-yl]propane-2-sulfonamide;
N'-[3-(4-chlorophenyl)-2-(2-methoxyphenyl)-2,4,5,6-tetrahydrocyclopenta[c]pyrazol-5-yl]-N,N-dimethylsulfamide;
3-(4-chlorophenyl)-2-(2-methoxyphenyl)-2,6-dihydrocyclopenta[c]pyrazol-5(4H)-one;
3-(4-chlorophenyl)-2-(2-ethoxyphenyl)-2,6-dihydrocyclopenta[c]pyrazol-5(4H)-one;
N-[3-(4-chlorophenyl)-2-(2-methoxyphenyl)-2,4,5,6-tetrahydrocyclopenta[c]pyrazol-5-yl]-N-methylmethanesulfonamide;
1-[3-(4-chlorophenyl)-2-(2-ethoxyphenyl)-2,4,5,6-tetrahydrocyclopenta[c]pyrazol-5-yl]pyrrolidine-2,5-dione;
3-(4-chlorophenyl)-2-(2-ethoxyphenyl)-5-(1H-imidazol-1-yl)-2,4,5,6-tetrahydrocyclopenta[c]pyrazole;
1-[3-(4-chlorophenyl)-2-(2-ethoxyphenyl)-2,4,5,6-tetrahydrocyclopenta[c]pyrazol-5-yl]pyrrolidin-2-one;
3-(4-chlorophenyl)-2-(2-ethoxyphenyl)-5-[4-(trimethylsilyl)-1H-1,2,3-triazol-1-yl]-2,4,5,6-tetrahydrocyclopenta[c]pyrazole;
3-(4-chlorophenyl)-2-(2-ethoxyphenyl)-5-(1H-1,2,3-triazol-1-yl)-2,4,5,6-tetrahydrocyclopenta[c]pyrazole;
(5R)-3-(4-chlorophenyl)-2-(2-ethoxyphenyl)-5-(1H-imidazol-1-yl)-2,4,5,6-tetrahydrocyclopenta[c]pyrazole;
N-[(5R)-3-(4-chlorophenyl)-2-(2-ethoxyphenyl)-2,4,5,6-tetrahydrocyclopenta[c]pyrazol-5-yl]propane-2-sulfonamide;
N-[(5R)-3-(4-chlorophenyl)-2-(2-ethoxyphenyl)-2,4,5,6-tetrahydrocyclopenta[c]pyrazol-5-yl]-2,2,2-trifluoroacetamide;
N-[(5R)-3-(4-chlorophenyl)-2-(2-ethoxyphenyl)-2,4,5,6-tetrahydrocyclopenta[c]pyrazol-5-yl]-N,N',N'-trimethylsulfamide;
N'-[3-(4-chlorophenyl)-2-(2-ethoxyphenyl)-2,4,5,6-tetrahydrocyclopenta[c]pyrazol-5-yl]-N,N-dimethylsulfamide;
N-[3-(4-chlorophenyl)-2-(2-ethoxyphenyl)-2,4,5,6-tetrahydrocyclopenta[c]pyrazol-5-yl]-N,N',N'-trimethylsulfamide;
(5R)-3-(4-chlorophenyl)-5-methoxy-2-(2-methoxyphenyl)-2,4,5,6-tetrahydrocyclopenta[c]pyrazole;

N-[(5S)-3-(4-chlorophenyl)-2-(2,3-dihydro-1-benzofuran-7-yl)-2,4,5,6-tetrahydrocyclopenta[c]pyrazol-5-yl]-N,N',N'-trimethylsulfamide;

N-[(5S)-3-(4-chlorophenyl)-2-(2,3-dihydro-1-benzofuran-7-yl)-2,4,5,6-tetrahydrocyclopenta[c]pyrazol-5-yl]-N-methylpropane-2-sulfonamide;

2-(4-Chloro-2-methoxyphenyl)-3-(4-chlorophenyl)-2,6-dihydro-4H-spiro[cyclopenta[c]pyrazole-5,2'-[1,3]dioxane];

(5Z)-3-(4-chlorophenyl)-2-(2-methoxyphenyl)-2,6-dihydrocyclopenta[c]pyrazol-5(4H)-one oxime;

3-(4-chlorophenyl)-2-(2-methoxyphenyl)-2,6-dihydro-4H-spiro[cyclopenta[c]pyrazole-5,2'-[1,3]dioxane];

(5R)-3-(4-chlorophenyl)-2-(2-methoxyphenyl)-2,4,5,6-tetrahydrocyclopenta[c]pyrazol-5-yl 2-ethylbutanoate;

N-[(5R)-2-(2-Methoxyphenyl)-3-(6-methoxypyridin-3-yl)-2,4,5,6-tetrahydrocyclopenta[c]pyrazol-5-yl]-N,N',N'-trimethylsulfamide;

N-{(5R)-2-(2-Methoxyphenyl)-3-[6-(1-methylethoxy)pyridin-3-yl]-2,4,5,6-tetrahydrocyclopenta[c]pyrazol-5-yl}-N,N',N'-trimethylsulfamide;

(5S)-3-(4-chlorophenyl)-2-(2-methoxyphenyl)-5-phenoxy-2,4,5,6-tetrahydrocyclopenta[c]pyrazole;

(5S)-3-(4-chlorophenyl)-2-(2-methoxyphenyl)-5-(pyridin-3-yloxy)-2,4,5,6-tetrahydrocyclopenta[c]pyrazole;

3-(4-chlorophenyl)-2-(2-methoxyphenyl)-5-[6-(1-methylethoxy)pyridin-3-yl]-2,4,5,6-tetrahydrocyclopenta[c]pyrazole;

(5R)-3-(4-chlorophenyl)-2-(2-methoxyphenyl)-5-(pyridin-2-yloxy)-2,4,5,6-tetrahydrocyclopenta[c]pyrazole;

3-(4-chlorophenyl)-2-(2-methoxyphenyl)-5-(6-morpholin-4-ylpyridin-3-yl)-2,4,5,6-tetrahydrocyclopenta[c]pyrazole;

3-(4-chlorophenyl)-2-(2-methoxyphenyl)-5-pyridin-3-yl-2,4,5,6-tetrahydrocyclopenta[c]pyrazole;

3-(4-chlorophenyl)-5-(4,4-dimethylcyclohexyl)-2-(2-methoxyphenyl)-2,4,5,6-tetrahydrocyclopenta[c]pyrazole;

3-[3-(4-chlorophenyl)-2-(2-methoxyphenyl)-2,4,5,6-tetrahydrocyclopenta[c]pyrazol-5-yl]-1,2,3,4-tetrahydroquinoline;

Ethyl 5-[3-(4-chlorophenyl)-2-(2-methoxyphenyl)-2,4,5,6-tetrahydrocyclopenta[c]pyrazol-5-yl]pyridine-3-carboxylate;

(5S)-3-(4-chlorophenyl)-2-(2-methoxyphenyl)-5-(1-methylethoxy)-2,4,5,6-tetrahydrocyclopenta[c]pyrazole;

3-(4-chlorophenyl)-2-(2-methoxyphenyl)-5-morpholin-4-yl-2,4,5,6-tetrahydrocyclopenta[c]pyrazole;

(5S)-3-(4-chlorophenyl)-2-(2-methoxyphenyl)-5-[(trimethylsilyl)oxy]-2,4,5,6-tetrahydrocyclopenta[c]pyrazole;

(5S)-3-(4-chlorophenyl)-2-(2-methoxyphenyl)-2,4,5,6-tetrahydrocyclopenta[c]pyrazol-5-yl 2-ethylbutanoate;

3-(4-chlorophenyl)-2-(2-methoxyphenyl)-5',5'-dimethyl-2,6-dihydro-4H-spiro[cyclopenta[c]pyrazole-5,2'-[1,3]dioxane];

(5S)-3-(4-chlorophenyl)-5-(2-ethylbutoxy)-2-(2-methoxyphenyl)-2,4,5,6-tetrahydrocyclopenta[c]pyrazole;

3-(4-chlorophenyl)-2-(2-methoxyphenyl)-5-(6-methylpyridin-3-yl)-2,4,5,6-tetrahydrocyclopenta[c]pyrazole;

3-(4-chlorophenyl)-5-(6-ethoxypyridin-3-yl)-2-(2-methoxyphenyl)-2,4,5,6-tetrahydrocyclopenta[c]pyrazole;

5-[2-Chloro-6-(1-methylethyl)pyridin-3-yl]-3-(4-chlorophenyl)-2-(2-methoxyphenyl)-2,4,5,6-tetrahydrocyclopenta[c]pyrazole;

(5S)-3-(4-chlorophenyl)-2-(2-methoxyphenyl)-5-(tetrahydro-2H-pyran-2-yloxy)-2,4,5,6-tetrahydrocyclopenta[c]pyrazole 3-(4-chlorophenyl)-5-(6-cyclopropylpyridin-3-yl)-2-(2-methoxyphenyl)-2,4,5,6-tetrahydrocyclopenta[c]pyrazole;

(5S)-3-(4-chlorophenyl)-2-(2-methoxyphenyl)-2,4,5,6-tetrahydrocyclopenta[c]pyrazol-5-yl cyclohexanecarboxylate;

(5S)-3-(4-chlorophenyl)-2-(2-methoxyphenyl)-2,4,5,6-tetrahydrocyclopenta[c]pyrazol-5-yl cyclopentanecarboxylate;

(5S)-3-(4-chlorophenyl)-2-(2-methoxyphenyl)-2,4,5,6-tetrahydrocyclopenta[c]pyrazol-5-yl cyclobutanecarboxylate;

(5S)-3-(4-chlorophenyl)-2-(2-methoxyphenyl)-2,4,5,6-tetrahydrocyclopenta[c]pyrazol-5-yl 2-methylpropanoate;

(5S)-3-(4-chlorophenyl)-5-(cyclohexylmethoxy)-2-(2-methoxyphenyl)-2,4,5,6-tetrahydrocyclopenta[c]pyrazole;

(5S)-3-(4-chlorophenyl)-5-(cyclopentylmethoxy)-2-(2-methoxyphenyl)-2,4,5,6-tetrahydrocyclopenta[c]pyrazole;

(5S)-3-(4-chlorophenyl)-5-(cyclobutylmethoxy)-2-(2-methoxyphenyl)-2,4,5,6-tetrahydrocyclopenta[c]pyrazole;

(5S)-3-(4-chlorophenyl)-2-(2-methoxyphenyl)-5-(2-methylpropoxy)-2,4,5,6-tetrahydrocyclopenta[c]pyrazole;

(5S)-3-(4-chlorophenyl)-2-(2-methoxyphenyl)-2,4,5,6-tetrahydrocyclopenta[c]pyrazol-5-yl tetrahydro-2H-pyran-4-carboxylate;

(5S)-3-(4-chlorophenyl)-2-(2-methoxyphenyl)-5-(tetrahydro-2H-pyran-4-ylmethoxy)-2,4,5,6-tetrahydrocyclopenta[c]pyrazole;

(5S)-3-(4-chlorophenyl)-5-(cyclohexyloxy)-2-(2-methoxyphenyl)-2,4,5,6-tetrahydrocyclopenta[c]pyrazole;

(5S)-5-[(1S,2S,4R)-bicyclo[2.2.1]hept-2-yloxy]-3-(4-chlorophenyl)-2-(2-methoxyphenyl)-2,4,5,6-tetrahydrocyclopenta[c]pyrazole;

(5S)-3-(4-chlorophenyl)-5-(cyclopentyloxy)-2-(2-methoxyphenyl)-2,4,5,6-tetrahydrocyclopenta[c]pyrazole;

4-[2-(2-methoxyphenyl)-5',5'-dimethyl-2,6-dihydro-4H-spiro[cyclopenta[c]pyrazole-5,2'-[1,3]dioxan]-3-yl]benzonitrile;

3-(4-chlorophenyl)-2-(2-methoxyphenyl)-5-(1-methylethyl)-2,4,5,6-tetrahydrocyclopenta[c]pyrazole;

4-[2-(2-methoxyphenyl)-5',5'-dimethyl-2,6-dihydro-4H-spiro[cyclopenta[c]pyrazole-5,2'-[1,3]dioxan]-3-yl]-N,N-dimethylaniline;

3-(6-ethoxypyridin-3-yl)-2-(2-methoxyphenyl)-5',5'-dimethyl-2,6-dihydro-4H-spiro[cyclopenta[c]pyrazole-5,2'-[1,3]dioxane];

2-(2-methoxyphenyl)-5',5'-dimethyl-3-(6-methylpyridin-3-yl)-2,6-dihydro-4H-spiro[cyclopenta[c]pyrazole-5,2'-[1,3]dioxane];

2-(2-methoxyphenyl)-3-(6-methoxypyridin-3-yl)-5',5'-dimethyl-2,6-dihydro-4H-spiro[cyclopenta[c]pyrazole-5,2'-[1,3]dioxane];

5-[2-(2-methoxyphenyl)-5',5'-dimethyl-2,6-dihydro-4H-spiro[cyclopenta[c]pyrazole-5,2'-[1,3]dioxan]-3-yl]-N,N-dimethylpyridin-2-amine;

(4'R,5'R)-3-(4-chlorophenyl)-2-(2-methoxyphenyl)-4',5'-dimethyl-2,6-dihydro-4H-spiro[cyclopenta[c]pyrazole-5,2'-[1,3]dioxolane]; (4'S,5'S)-3-(4-chlorophenyl)-2-(2-methoxyphenyl)-4',5'-dimethyl-2,6-dihydro-4H-spiro[cyclopenta[c]pyrazole-5,2'-[1,3]dioxolane];

(4'R,6'R)-3-(4-chlorophenyl)-2-(2-methoxyphenyl)-4',6'-dimethyl-2,6-dihydro-4H-spiro[cyclopenta[c]pyrazole-5,2'-[1,3]dioxane];

(4'S,6'S)-3-(4-chlorophenyl)-2-(2-methoxyphenyl)-4',6'-dimethyl-2,6-dihydro-4H-spiro[cyclopenta[c]pyrazole-5,2'-[1,3]dioxane];

(4'R,5'S)-3-(4-chlorophenyl)-2-(2-methoxyphenyl)-4',5'-dimethyl-2,6-dihydro-4H-spiro[cyclopenta[c]pyrazole-5,2'-[1,3]dioxolane];

(4'R,5'S)-3-(4-chlorophenyl)-2-(2-methoxyphenyl)-4',5'-dimethyl-2,6-dihydro-4H-spiro[cyclopenta[c]pyrazole-5,2'-[1,3]dioxolane];

3-(4-chlorophenyl)-5-cyclohexyl-2-(2-methoxyphenyl)-2,4,5,6-tetrahydrocyclopenta[c]pyrazole;

4-[2-(2-methoxyphenyl)-5-(2-methylpropyl)-2,4,5,6-tetrahydrocyclopenta[c]pyrazol-3-yl]benzonitrile;

4-[5-(cyclohexylmethyl)-2-(2-methoxyphenyl)-2,4,5,6-tetrahydrocyclopenta[c]pyrazol-3-yl]benzonitrile;

4-[2-(2-methoxyphenyl)-4',4',5',5'-tetramethyl-2,6-dihydro-4H-spiro[cyclopenta[c]pyrazole-5,2'-[1,3]dioxolan]-3-yl]-N,N-dimethylaniline;

3-(6-ethoxypyridin-3-yl)-2-(2-methoxyphenyl)-4',4',5',5'-tetramethyl-2,6-dihydro-4H-spiro[cyclopenta[c]pyrazole-5,2'-[1,3]dioxolane];

2-(2-methoxyphenyl)-4',4',5',5'-tetramethyl-3-(6-methylpyridin-3-yl)-2,6-dihydro-4H-spiro[cyclopenta[c]pyrazole-5,2'-[1,3]dioxolane];

5-[2-(2-methoxyphenyl)-4',4',5',5'-tetramethyl-2,6-dihydro-4H-spiro[cyclopenta[c]pyrazole-5,2'-[1,3]dioxolan]-3-yl]-N,N-dimethylpyridin-2-amine;

4-[2-(2-methoxyphenyl)-4',4',5',5'-tetramethyl-2,6-dihydro-4H-spiro[cyclopenta[c]pyrazole-5,2'-[1,3]dioxolan]-3-yl]benzonitrile;

(3aR,7aS)-3'-(4-chlorophenyl)-2'-(2-methoxyphenyl)-2',3a,4,5,6,6',7,7a-octahydro-4'H-spiro[1,3-benzodioxole-2,5'-cyclopenta[c]pyrazole];

(3aS,6aS)-3'-(4-chlorophenyl)-2'-(2-methoxyphenyl)-2',4,5,6',6a-hexahydro-3aH,4'H-spiro[cyclopenta[d][1,3]dioxole-2,5'-cyclopenta[c]pyrazole];

(3aR,6aS)-3'-(4-chlorophenyl)-2'-(2-methoxyphenyl)-2',4,5,6',6a-hexahydro-3aH,4'H-spiro[cyclopenta[d][1,3]dioxole-2,5'-cyclopenta[c]pyrazole];

(3aR,6aS)-3'-(4-chlorophenyl)-2'-(2-methoxyphenyl)-2',4,5,6',6a-hexahydro-3aH,4'H-spiro[cyclopenta[d][1,3]dioxole-2,5'-cyclopenta[c]pyrazole];

3-(4-chlorophenyl)-5-(2,6-dimethylmorpholin-4-yl)-2-(2-methoxyphenyl)-2,4,5,6-tetrahydrocyclopenta[c]pyrazole;

3-(4-chlorophenyl)-2-(2-methoxyphenyl)-5-(4-methylpiperidin-1-yl)-2,4,5,6-tetrahydrocyclopenta[c]pyrazole;

3-(4-chlorophenyl)-5-(3,3-diethylpyrrolidin-1-yl)-2-(2-methoxyphenyl)-2,4,5,6-tetrahydrocyclopenta[c]pyrazole;

3-(4-chlorophenyl)-5-(3,3-dimethylpyrrolidin-1-yl)-2-(2-methoxyphenyl)-2,4,5,6-tetrahydrocyclopenta[c]pyrazole;

3-(5-chlorothiophen-2-yl)-2-(2-methoxyphenyl)-5',5'-dimethyl-2,6-dihydro-4H-spiro[cyclopenta[c]pyrazole-5,2'-[1,3]dioxane];

3-(5-chlorothiophen-2-yl)-2-(2-methoxyphenyl)-4',4',5',5'-tetramethyl-2,6-dihydro-4H-spiro[cyclopenta[c]pyrazole-5,2'-[1,3]dioxolane];

3-(4-chlorophenyl)-2-(2-methoxyphenyl)-5-pyrrolidin-1-yl-2,4,5,6-tetrahydrocyclopenta[c]pyrazole;

3-(4-chlorophenyl)-5-(3,3-difluoropyrrolidin-1-yl)-2-(2-methoxyphenyl)-2,4,5,6-tetrahydrocyclopenta[c]pyrazole;

4-[(5S)-5-(4-cyclopentyl-1H-1,2,3-triazol-1-yl)-2-(2-methoxyphenyl)-2,4,5,6-tetrahydrocyclopenta[c]pyrazol-3-yl]benzonitrile;

methyl 1-[(5S)-3-(4-cyanophenyl)-2-(2-methoxyphenyl)-2,4,5,6-tetrahydrocyclopenta[c]pyrazol-5-yl]-1H-1,2,3-triazole-4-carboxylate;

4-[(5S)-5-[4-(1-hydroxy-1-methylethyl)-1H-1,2,3-triazol-1-yl]-2-(2-methoxyphenyl)-2,4,5,6-tetrahydrocyclopenta[c]pyrazol-3-yl]benzonitrile;

4-{(5S)-2-(2-methoxyphenyl)-5-[4-(2-methylpropyl)-1H-1,2,3-triazol-1-yl]-2,4,5,6-tetrahydrocyclopenta[c]pyrazol-3-yl}benzonitrile;

{1-[(5S)-3-(4-cyanophenyl)-2-(2-methoxyphenyl)-2,4,5,6-tetrahydrocyclopenta[c]pyrazol-5-yl]-1H-1,2,3-triazol-4-yl}methyl acetate;

4-[(5S)-5-[4-(methoxymethyl)-1H-1,2,3-triazol-1-yl]-2-(2-methoxyphenyl)-2,4,5,6-tetrahydrocyclopenta[c]pyrazol-3-yl]benzonitrile;

4-[(5S)-5-(4-tert-butyl-1H-1,2,3-triazol-1-yl)-2-(2-methoxyphenyl)-2,4,5,6-tetrahydrocyclopenta[c]pyrazol-3-yl]benzonitrile;

4-[(5S)-5-(4,5-dimethyl-1H-imidazol-1-yl)-2-(2-methoxyphenyl)-2,4,5,6-tetrahydrocyclopenta[c]pyrazol-3-yl]benzonitrile;

4-[(5S)-2-(2-methoxyphenyl)-5-(2,4,5-trimethyl-1H-imidazol-1-yl)-2,4,5,6-tetrahydrocyclopenta[c]pyrazol-3-yl]benzonitrile;

4-[(5S)-5-(2-ethyl-4,5-dimethyl-1H-imidazol-1-yl)-2-(2-methoxyphenyl)-2,4,5,6-tetrahydrocyclopenta[c]pyrazol-3-yl]benzonitrile;

4-[(5S)-5-(2-ethyl-1H-imidazol-1-yl)-2-(2-methoxyphenyl)-2,4,5,6-tetrahydrocyclopenta[c]pyrazol-3-yl]benzonitrile;

4-[(5S)-2-(2-methoxyphenyl)-5-(2-methyl-1H-imidazol-1-yl)-2,4,5,6-tetrahydrocyclopenta[c]pyrazol-3-yl]benzonitrile;

4-[(5S)-5-(4,5-diethyl-1H-1,2,3-triazol-1-yl)-2-(2-methoxyphenyl)-2,4,5,6-tetrahydrocyclopenta[c]pyrazol-3-yl]benzonitrile;

4-[(5S)-2-(2-methoxyphenyl)-5-(2,4,5-triethyl-1H-imidazol-1-yl)-2,4,5,6-tetrahydrocyclopenta[c]pyrazol-3-yl]benzonitrile;

4-[(5S)-5-(4,5-diethyl-2-methyl-1H-imidazol-1-yl)-2-(2-methoxyphenyl)-2,4,5,6-tetrahydrocyclopenta[c]pyrazol-3-yl]benzonitrile;

4-[(5S)-5-(4,5-diethyl-1H-imidazol-1-yl)-2-(2-methoxyphenyl)-2,4,5,6-tetrahydrocyclopenta[c]pyrazol-3-yl]benzonitrile;

and pharmaceutically acceptable salt forms thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salts thereof. Suitable pharmaceutically acceptable salts of compounds of Formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as.

$$\%(+) - \text{enantiomer} = \frac{(\text{mass}(+) - \text{enantiomer})}{(\text{mass}(+) - \text{enantiomer}) + (\text{mass}(-) - \text{enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-) - \text{enantiomer} = \frac{(\text{mass}(-) - \text{enantiomer})}{(\text{mass}(+) - \text{enantiomer}) + (\text{mass}(-) - \text{enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein; or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As N-Type calcium channel blockers, the compounds of Formula (I) are useful in methods for treating and/or preventing a disease, a syndrome, a condition or a disorder in a subject, including an animal, a mammal and a human in which the disease, the syndrome, the condition or the disorder is affected by the modulation of the N-Type calcium channel. Such methods comprise, consist of and/or consist essentially of administering to a subject, including an animal, a mammal, and a human in need of such treatment or prevention a therapeutically effective amount of a compound, salt or solvate of Formula (I). In particular, the compounds of Formula (I) are useful for preventing or treating pain, such as inflammatory pain or neuropathic pain, or diseases, syndromes, conditions or disorders causing such pain.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:
- ACN acetonitrile
- AcOH glacial acetic acid
- aq. aqueous
- Bn or Bzl benzyl
- Boc tert-butyloxycarbonyl
- conc. concentrated
- DBU 1,8-diazabicyclo[5.4.0]undec-7-ene
- DCC N,N'-dicyclohexyl-carbodiimide
- DCE 1,2-dichloroethane
- DCM dichloromethane
- DIBALH diisobutylaluminum hydride
- DIPEA or DIEA diisopropyl-ethyl amine
- DMF N,N-dimethylformamide
- DMSO dimethylsulfoxide
- EA ethyl acetate
- EDCI 1-ethyl-3-(3-dimethylaminopropyl) carbodiimide
- EGTA ethylene glycol tetraacetic acid
- ESI electrospray ionization
- EtOAc or EA ethyl acetate
- EtOH ethanol
- h or hr(s) hour or hours
- HEK human embryonic kidney
- HEPES (4-(2-hydroxyethyl)-1-piperazineethane sulfonic acid
- HPLC high performance liquid chromatography
- LAH lithium aluminum hydride
- LDA lithium diisopropylamide
- LHMDS lithium bis(trimethylsilyl)amide
- mCPBA meta-chloroperoxybenzoic acid
- MeOH methanol
- MHz megahertz
- min minute or minutes
- MS mass spectrometry
- Ms methanesulfonyl
- NMM N-methylmorpholine
- NMR nuclear magnetic resonance
- PCC pyridinium chlorochromate
- RP reverse-phase
- RT room temperature
- $R_t$ retention time
- Sec second or seconds
- TBDMS t-butyldimethylsilyl
- TEA or $Et_3N$ triethylamine
- TFA trifluoroacetic acid
- THF tetrahydrofuran
- TIPS triisopropylsilyl
- TLC thin layer chromatography
- TMS tetramethylsilane Scheme A illustrates a route for the synthesis of compounds of Formula (I)-A, -A1, and -A2 wherein Q, $R^1$, $R^2$, and $R^3$ are as defined herein, and G is a functionalized ethyl group.

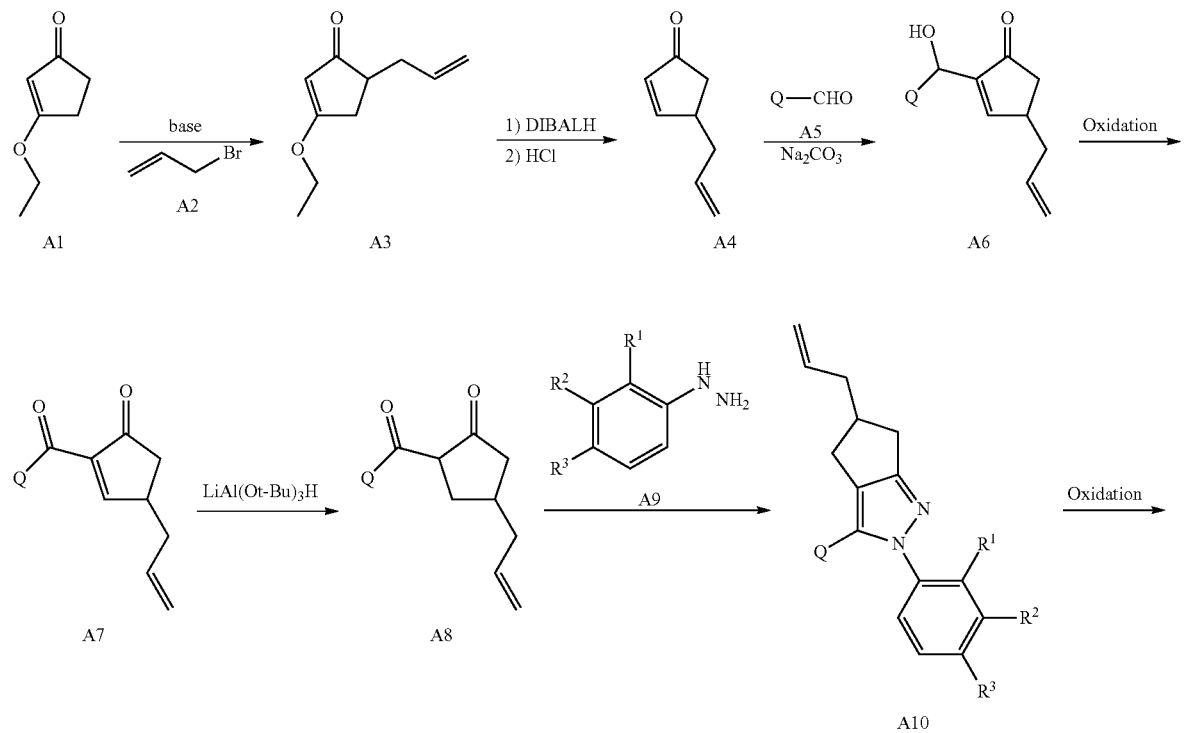

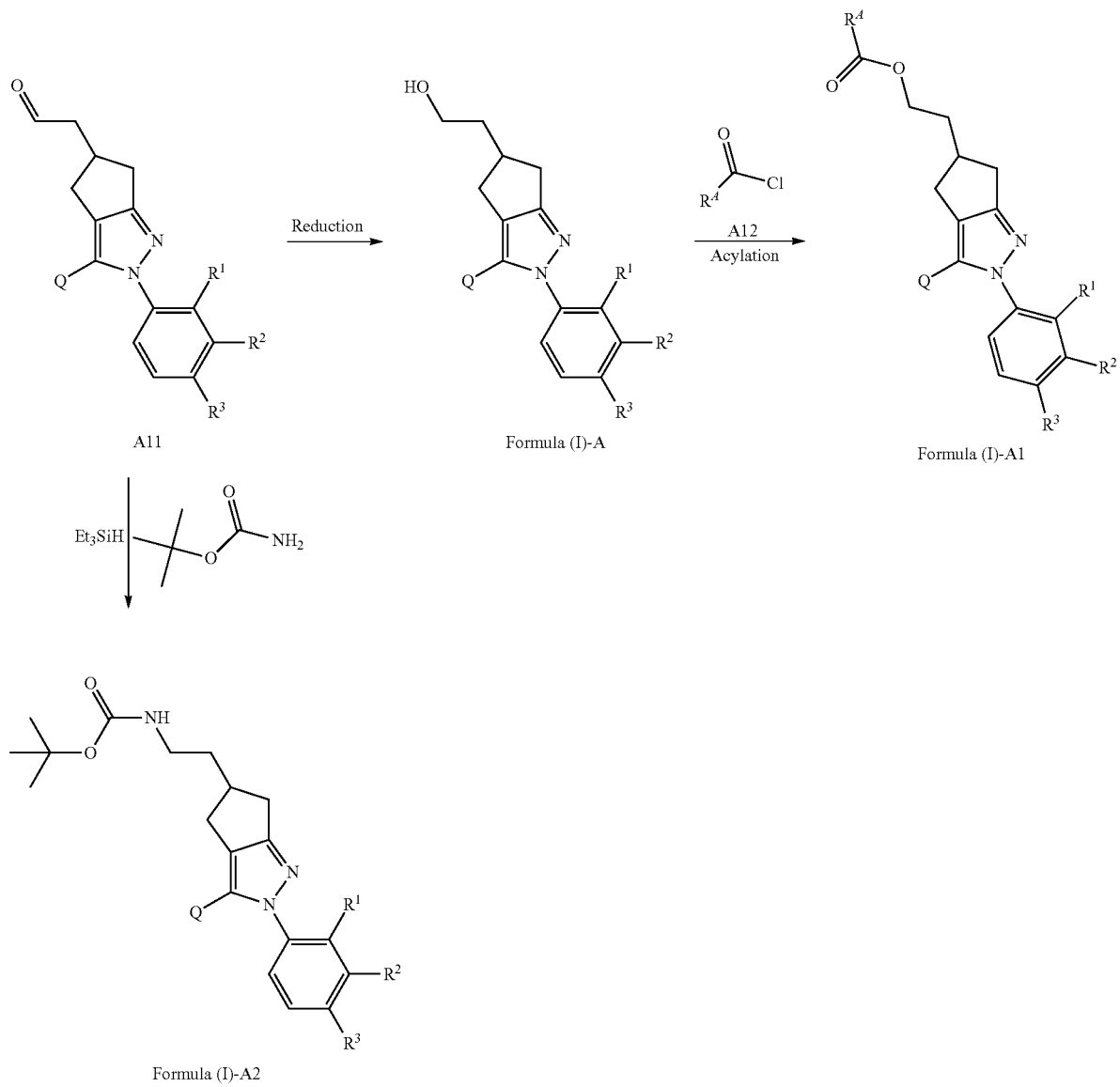

Formula (I)-A2

A compound of formula A1 is either commercially available or may be prepared by methods known in the scientific literature. A compound of formula A1 may be alkylated with an unsaturated alkyl bromide of formula A2, in the presence of a base such as LHMDS, to afford a compound of formula A3. A compound of formula A3 may be undergo a reduction in the presence of a hydride source such as DIBALH or LAH, or the like, to afford a compound of formula A4. Nucleophilic addition to a Q-substituted aldehyde of formula A5 affords the alcohol of formula A6. The alcohol of a compound of formula A6 may be oxidized to the corresponding ketone of formula A7 by the action of an oxidizing agent such as Dess-Martin periodinane, PCC, Swern reagent, or the like. Reduction of the α/β-unsaturation may be achieved in the presence of a hydride source such as lithium tri-t-butoxide aluminum hydride or the like, to afford a compound of formula A8. Cyclization with a hydrazine of formula A9 affords a pyrrolocyclopentyl ring of formula A10. Oxidation of the terminal alkenyl group of formula A10 in the presence of osmium tetraoxide affords the corresponding aldehyde of formula A11. Reduction of the aldehyde by the action of a reducing agent such as sodium borohydride or lithium aluminum hydride, or the like, affords a compound of formula (I)-A. The alcohol of formula (I)-A may be acylated by various conventional methods known to one of skill in the art to afford a compound of formula (I)-A1. For example, a compound of formula (I)-A may be acylated with an acid chloride of formula A12 (wherein $R^4$ is morpholin-4-yl or dimethylamino) to afford a compound of formula (I)-A1. A compound of formula A11 may also be treated with t-butylcarbamate in the presence of a hydride source such as triethylsilane or an acid such as TFA, to afford a carbamate of formula (I)-A2 of the present invention.

Scheme B illustrates a route for the synthesis of compounds of Formula (I)-B, -B1, and -B2, wherein Q, $R^1$, $R^2$, and $R^3$ are as defined herein, and G is a functionalized methylene group.

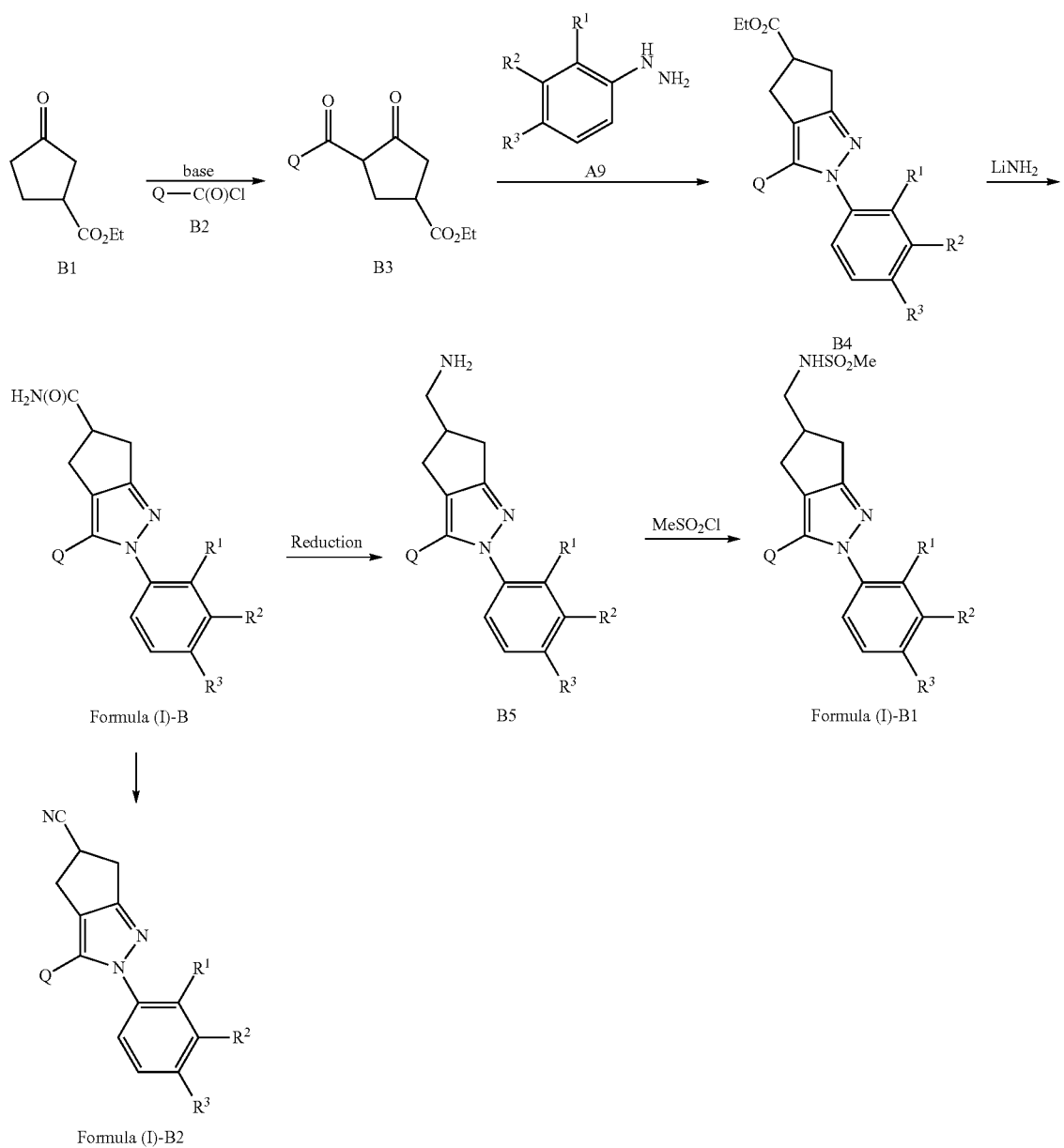

A compound of formula B1 is either commercially available or may be prepared by methods known in the scientific literature. A compound of formula B1 may be treated under basic conditions with an acid chloride of formula B2 to afford a compound of formula B3. Cyclization with a hydrazine of formula A9 affords pyrazolocyclopentyl ring of formula B4. Treatment with lithium amide affords the primary amide of formula (I)-B. Reduction of the amide in the presence of a hydride source such as lithium aluminum hydride or the like, affords a compound of formula B5, which subsequently may be treated with an alkylsulfonyl chloride, such as methanesulfonyl chloride, to afford a compound of formula (I)-B1. Alternatively, a compound of formula (I)-B may be treated with cyanuric chloride to afford the corresponding cyanide of formula (I)-B2.

Scheme C illustrates a route for the synthesis of compounds of Formula (I)-C and -C1, wherein Q, $R^1$, $R^2$, and $R^3$ are as defined herein, and G is an alcohol or carbamate.

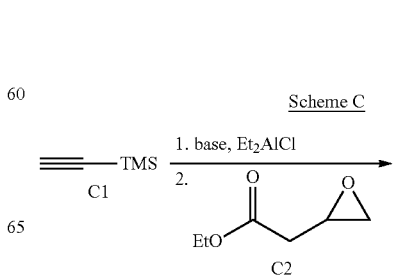

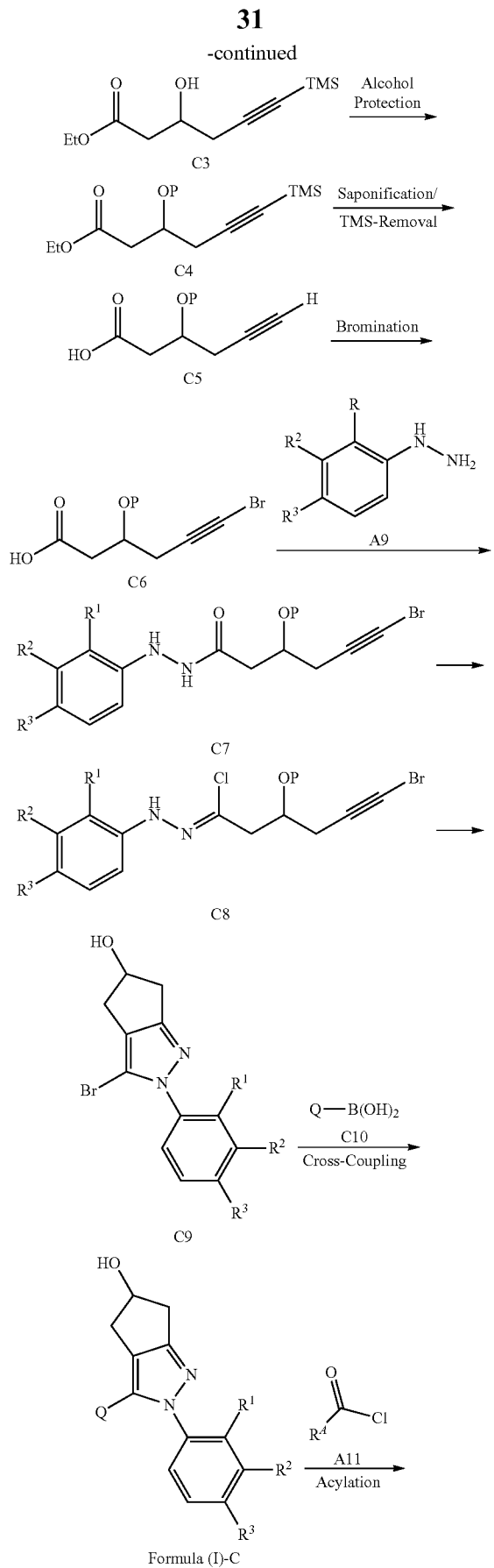

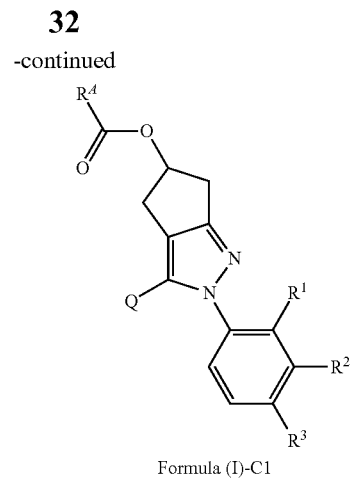

Formula (I)-C1

A compound of formula C1 is either commercially available or may be prepared by methods known in the scientific literature. A compound of formula C1 may be treated with a base such as an organolithium base, in the presence of a Lewis acid such as diethylaluminum chloride or boron trifluoride, followed by the addition of a compound of formula C2 to afford a compound of formula C3. The alcohol functional group may be protected, wherein "P" is a conventional alcohol protecting group such as TIPS, TBDMS, or benzyl, to afford a compound of formula C4. Treatment with hydroxide anion effected the saponification and removal of the TMS group to afford a compound of formula C5. A compound of formula C5 may be brominated in the presence of N-bromosuccinimide and silver nitrate to afford a compound of formula C6. Compound C6 may be treated with NMM in the presence of isobutylchloroformate or other amide-type coupling reagent, such as EDCI, and a compound of formula A9 to afford a compound of formula C7. The addition of carbon tetrachloride and polymer-bound triphenylphosphine to a compound of formula C7 afforded the compound of formula C8, which may be heated in the presence of a tertiary amine base, such as triethylamine or DIEA, to afford the cyclized product of formula C9. A compound of formula C9 may be cross-coupled with a boronic acid of formula C10 in the presence of the a transition metal catalyst, appropriate ligands, and in the presence of an inorganic base such as sodium carbonate to afford a compound of formula (I)-C. Acylation with a compound of formula A11 affords compounds of formula (I)-C1 of the present invention.

Scheme D illustrates a route for the synthesis of compounds of Formula (I)-D, wherein Q, $R^1$, $R^2$, and $R^3$ are as defined herein, and G is a sulfonamide as defined herein.

Scheme D

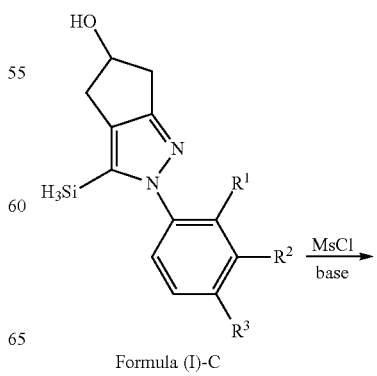

Formula (I)-C

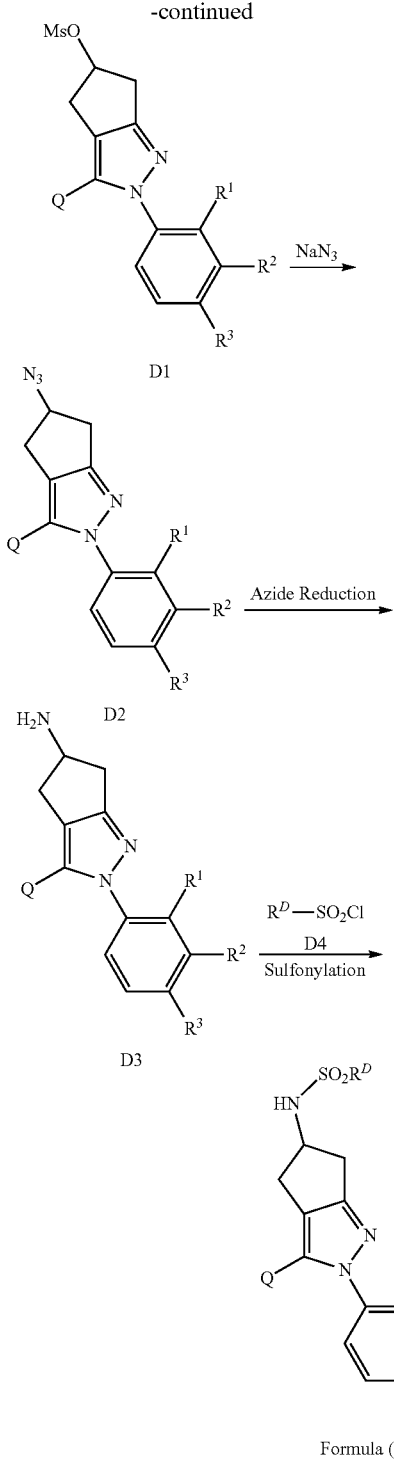

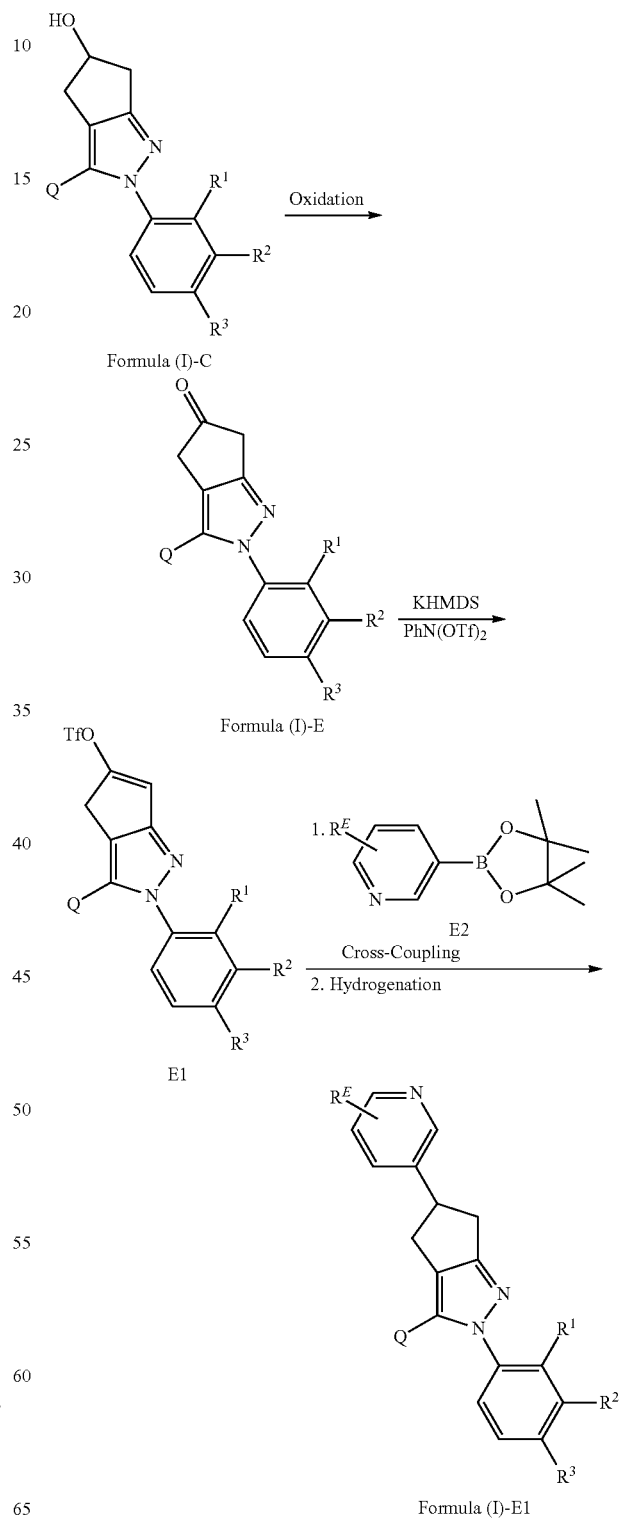

A compound of formula (I)-C may be treated with methanesulfonyl chloride to afford a compound of formula D1. Treatment with sodium azide effects the nucleophilic displacement to the mesylate to afford the corresponding azide of formula D2. Azide reduction may be accomplished by conventional catalytic hydrogenation or by treatment with triphenylphosphine to afford the amine of formula D3. A compound of formula D3 may be acylated with an appropriately substituted sulfonyl chloride (wherein $R^D$ is methyl, isopropyl, or dimethylamino, for example) to afford compounds of formula (I)-D of the present invention.

Scheme E illustrates a route for the synthesis of compounds of Formula (I)-E and -E1, wherein Q, $R^1$, $R^2$, and $R^3$ are as defined herein, and G is 1,2,3,4-tetrahydroquinolin-3-yl, an optionally substituted pyridinyl (wherein $R^E$ is hydrogen, $C_{1-4}$alkyl, $C_{1-4}$alkoxy, chloro, cyclopropyl, morpholin-4-yl, or $C_{1-4}$alkoxycarbonyl), or $C_{3-6}$cycloalkyl as defined herein. For illustrative purposes only, Scheme E shows a cross-coupling with an optionally substituted pyridinylboronic ester.

Scheme E

A compound of formula (I)-C may be oxidized by the action of an oxidizing agent such as Dess-Martin periodinane, PCC, Swern reagent, or the like, to afford the corresponding ketone of formula (I)-E. Treatment with a base such as KHMDS, DBU, LDA, or the like, and N-phenyl-bis(trifluoromethanesulfonimide) or other triflating reagent affords a compound of formula E1. A compound of formula E1 may be cross-coupled with a boronic ester of formula E2 in the presence of a palladium catalyst, appropriate ligands, and an inorganic base, followed by conventional hydrogenation, to afford a compound of formula (I)-E1.

Scheme F illustrates a route for the synthesis of compounds of Formula (I)-F, wherein Q, $R^1$, $R^2$, and $R^3$ are as defined herein, and G is a spirofused heterocyclyl as defined herein.

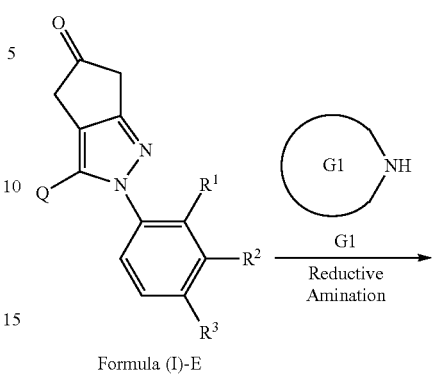

A compound of formula (I)-E may be treated with a compound of formula F1 (wherein the carbon atoms of F1 are optionally substituted with one to four methyl substituents) in the presence of a Lewis acid such as boron trifluoride-etherate to afford a ketal of formula (I)-F.

Scheme G illustrates a route for the synthesis of compounds of Formula (I)-F, wherein Q, $R^1$, $R^2$, and $R^3$ are as defined herein, and G is ring G1, a cyclic amine such as morpholinyl or an optionally substituted piperidinyl or pyrrolidinyl ring.

A compound of formula (I)-E may be treated with a compound of formula G1 (in the presence of a hydride source such as sodium cyanoborohydride, sodium triacetoxyborohydride, or the like, to afford an amine of formula (I)-G.

Scheme H illustrates a route for the synthesis of compounds of Formula (I)-H, wherein Q, $R^1$, $R^2$, and $R^3$ are as defined herein, and G is an alkyl substituent, $R^H$, wherein $R^H$ is an optionally substituted $C_{1-6}$alkyl, $C_{3-6}$cycloalkyl($C_{1-4}$alkyl, or $C_{3-6}$cycloalkyl.

-continued

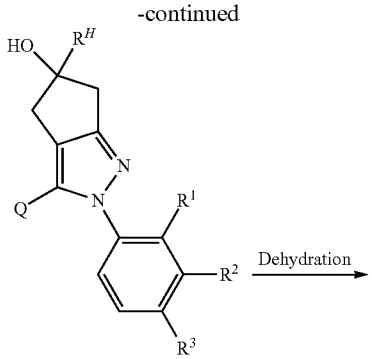

H2

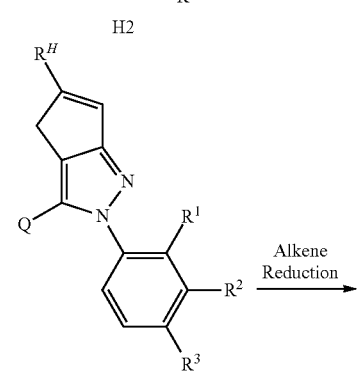

H3

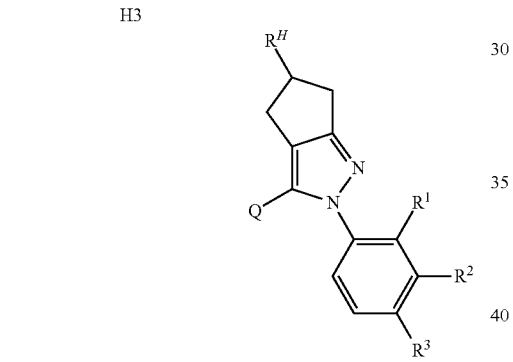

Formula (I)-H

A compound of formula (I)-E may be treated with an alkylmagnesium bromide of formula H1 to form a compound of formula H2. A compound of formula H2 may undergo dehydration in the presence of the Burgess reagent (methyl N-triethylammoniumsulfonyl) carbamate) to afford a compound of formula H3. Reduction of the alkenyl functionality may be achieved by conventional palladium-catalyzed hydrogenation to afford a compound of formula (I)-H.

SPECIFIC EXAMPLES

Example 1

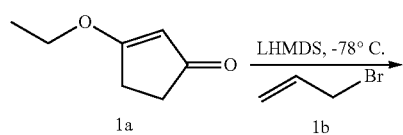

-continued

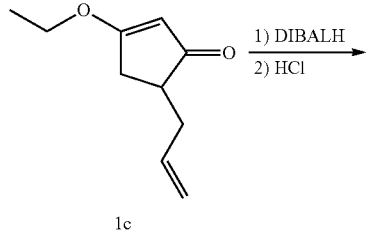

1c

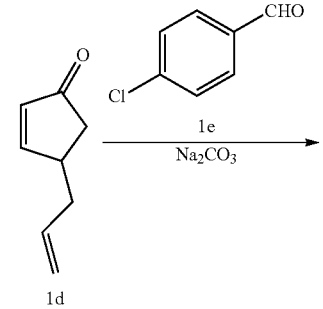

1d

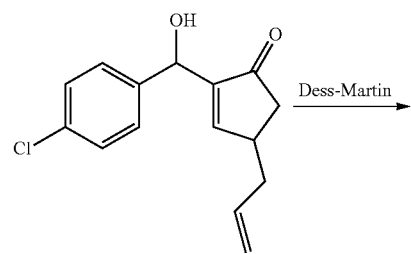

1f

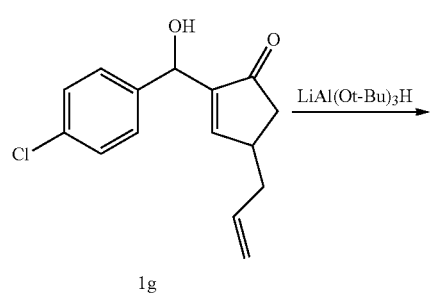

1g

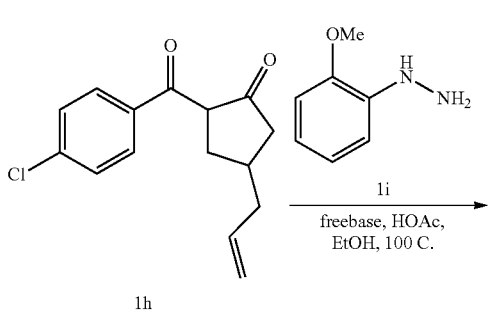

1h

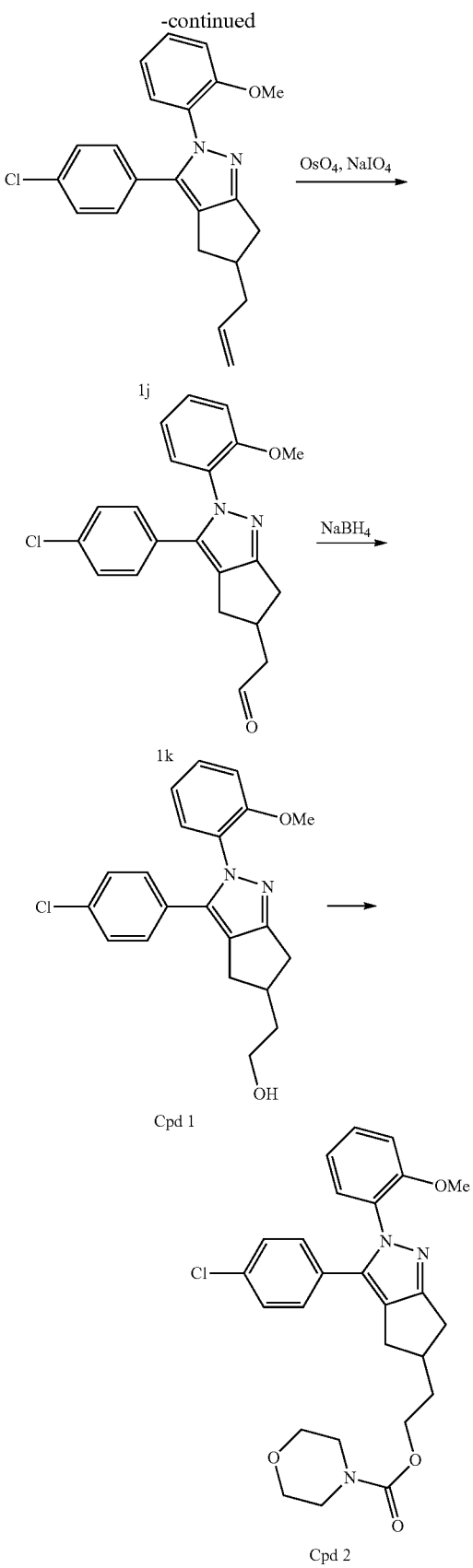

was added a solution of 3-ethoxy-2-cyclopentenone (1a) (4.0 mL, 33.45 mmol, 1 eq) in THF (40 mL) dropwise over 1 hr. After 20 min, a solution of allyl bromide (1b) (3.19 mL, 36.8 mmol, 1.1 eq) in THF (40 mL) was added over 10 min. After 3 hrs at −78° C., water and $NH_4Cl$ were added, the aqueous extracted with ether, the organics combined, dried over $MgSO_4$ and concentrated. Purification by chromatography (80 g), eluting with 15 to 40% EA/hexanes, gave compound 1c (3.05 g, 55%). $^1H$ NMR (CHLOROFORM-d) δ: 5.68-5.82 (m, J=16.9, 10.2, 6.8, 6.8 Hz, 1H), 5.25 (s, 1H), 5.01-5.12 (m, 2H), 4.04 (q, J=7.1 Hz, 2H), 2.65-2.75 (m, 1H), 2.57 (qd, J=6.6, 4.0 Hz, 2H), 2.28-2.39 (m, 1H), 2.11-2.23 (m, 1H), 1.41 (t, J=7.1 Hz, 3H). ESI-MS (m/z): Calcd. for C15H15ClO2: 167.1 (M+1). found: 167.1.

B. To a solution of compound 1c (3.05 g, 18.4 mmol, 1 eq) in THF (30 mL) at 0° C. was added diisobutylaluminum hydride (36.7 mL of a 1 M solution in hexanes, 36.7 mmol, 2 eq) over 1 hr. After 1 hr, 1 N HCl was added dropwise while at 0° C., then the reaction was warmed to rt over 2 hrs. The aqueous layer was extracted with ether, dried over $MgSO_4$ and concentrated to give compound 1d (2.2 g crude). Purification of compound 1d (1.0 g) by chromatography (40 g), eluting with 10 to 40% EA/hexanes, gave purified compound 1d (587 mg, 90%). $^1H$ NMR (CHLOROFORM-d) δ: 7.64 (dd, J=5.7, 2.4 Hz, 1H), 6.18 (dd, J=5.7, 1.9 Hz, 1H), 5.69-5.86 (m, J=17.2, 9.9, 7.0, 7.0 Hz, 1H), 5.05-5.21 (m, 2H), 2.97-3.12 (m, 1H), 2.52 (dd, J=18.8, 6.4 Hz, 1H), 2.16-2.38 (m, J=37.7, 14.1, 6.9, 6.9 Hz, 2H), 2.00-2.12 (m, 1H).

C. To a solution of compound 1d (587 mg, 4.81 mmol, 1 eq) and 4-chlorobenzaldehyde (1e) (541 mg, 3.85 mmol, 0.8 eq) in methanol (25 mL) at rt was added a solution of sodium carbonate (255 mg, 2.41 mmol, 0.5 eq) in water (10 mL). After 1 hr, 1 N HCl was added, and the methanol was evaporated. The aqueous solution was extracted with DCM, and the organic phase was dried over $MgSO_4$, filtered, and concentrated. Purification by chromatography (60 g), eluting with 10 to 25% EA/hexanes, gave compound 1f (721 mg, 71%). $^1H$ NMR (CHLOROFORM-d) δ: 7.28-7.36 (m, 4H), 7.13-7.21 (m, 1H), 5.65-5.79 (m, 1H), 5.53 (s, 1H), 5.03-5.12 (m, 2H), 3.45 (br. s., 1H), 2.89-2.99 (m, 1H), 2.56-2.67 (m, 1H), 2.28 (dt, J=13.6, 7.0 Hz, 1H), 2.10-2.23 (m, 2H). ESI-MS (m/z): Calcd. for C15H15ClO2: 245.1 (M−17). found: 245.0.

D. To a solution of compound 1f (1.18 g, 4.48 mmol, 1 eq) in DCM (40 mL) at 0° C. was added Dess-Martin periodinane (2.09 g, 4.93 mmol, 1.1 eq). After 1 hr, saturated $NaHCO_3$ and saturated sodium thiosulfate were added and the mixture was stirred for 30 min. The reaction mixture was extracted with DCM, dried over $MgSO_4$, filtered, and concentrated. Purification by chromatography (60 g), eluting with 15 to 25% EA/hexanes, gave compound 1g (660 mg, 57%). $^1H$ NMR (CHLOROFORM-d) δ: 7.95 (d, J=2.5 Hz, 1H), 7.72-7.79 (m, 2H), 7.41-7.47 (m, 2H), 5.74-5.89 (m, 1H), 5.12-5.22 (m, 2H), 3.14-3.23 (m, 1H), 2.78 (dd, J=19.2, 6.6 Hz, 1H), 2.28-2.50 (m, 3H). ESI-MS (m/z): Calcd. for C15H13ClO2: 261.1 (M+1). found: 261.0.

E. To a solution of compound 1g (660 mg, 2.53 mmol, 1 eq) in THF (20 mL) at 0° C. was added lithium tri-t-butoxide aluminum hydride (3.8 mL of a 1 M solution in THF, 3.8 mmol, 1.5 eq). After 30 min, 1 N HCl was added, the solution was extracted with ethyl acetate, the organic phase was dried over $MgSO_4$, filtered, and concentrated to give compound 1h, ~80% pure (653 mg, 98%).

A. To a solution of LHMDS (36.8 mL of a 1 M solution in THF, 36.8 mmol, 1.1 eq) in THF (70 mL) at −78° C. under Ar F. To a solution of compound 1h (415 mg, 1.58 mmol, 1 eq) in acetic acid (20 mL) at 80° C. was added 2-methoxyphenylhydrazine (1i) (252 mg, 1.82 mmol, 1.15 eq). After 1 hr, the solution was cooled to rt and concentrated. Purification by chromatography (40 g), eluting with 5 to 30% EA/hexanes, gave compound 1j (2$^{nd}$ major peak, 1$^{st}$ peak was undesired regioisomer, 227 mg, 39%). $^1$H NMR (CHLOROFORM-d) δ: 7.39 (dd, J=7.7, 1.6 Hz, 1H), 7.29-7.36 (m, 1H), 7.16-7.22 (m, 2H), 7.04-7.10 (m, 2H), 7.01 (td, J=7.6, 1.0 Hz, 1H), 6.88 (d, J=8.3 Hz, 1H), 5.81-5.94 (m, J=17.1, 10.2, 6.8, 6.8 Hz, 1H), 5.01-5.15 (m, 2H), 3.49 (s, 3H), 2.90-3.07 (m, 3H), 2.47-2.64 (m, 2H), 2.31-2.45 (m, 2H). ESI-MS (m/z): Calcd. for C22H21ClN2O: 365.1 (M+1). found: 365.3.

G. To a solution of compound 1j (116 mg, 0.32 mmol, 1 eq) in THF (7 mL) at 0° C. was added osmium tetraoxide (0.4 mL of a 2.5% solution in t-butanol, 0.032 mmol, 0.1 eq) followed by a solution of sodium periodate (411 mg, 1.92 mmol, 6 eq) in water (5 mL). After 1 hr, a saturated solution of sodium thiosulfate was added and the mixture was stirred for 30 min. The solution was then extracted with ether, the organic phase was dried over MgSO$_4$, filtered, and concentrated to give compound 1k. $^1$H NMR (CHLOROFORM-d) δ: 9.86 (t, J=1.5 Hz, 1H), 7.31-7.40 (m, 2H), 7.17-7.22 (m, 2H), 7.04-7.09 (m, 2H), 7.01 (td, J=7.6, 1.3 Hz, 1H), 6.88 (dd, J=8.3, 1.3 Hz, 1H), 3.50 (s, 3H), 3.35-3.45 (m, 1H), 3.06-3.18 (m, 2H), 2.81 (ddd, J=7.1, 5.3, 1.5 Hz, 2H), 2.46-2.62 (m, 2H). ESI-MS (m/z): Calcd. for C21H19ClN2O2: 367.1 (M+1). found: 367.1.

H. To a solution of compound 1k in methanol (2 mL) was added sodium borohydride (20 mg, 0.52 mmol, 1.7 eq). After 1 hr, water and NH$_4$Cl were added, the aqueous layer was extracted with ethyl acetate. The organic phase was dried over MgSO$_4$, filtered, and concentrated. Purification by chromatography (24 g), eluting with 40 to 100% EA/hexanes, gave compound 1 (61 mg, 52%). $^1$H NMR (CHLOROFORM-d/MeOH) δ: 7.33-7.41 (m, 2H), 7.19-7.24 (m, 2H), 7.06-7.11 (m, 2H), 7.04 (td, J=7.7, 1.3 Hz, 1H), 6.90-6.96 (m, 1H), 3.71 (t, J=6.8 Hz, 2H), 3.51 (s, 3H), 2.96-3.13 (m, 3H), 2.55 (dd, J=15.2, 7.8 Hz, 2H), 1.91 (q, J=6.8 Hz, 2H). ESI-MS (m/z): Calcd. for C21H21ClN2O2: 369.1 (M+1). found: 369.1.

I. To a solution of compound 1 (17 mg, 0.045 mmol, 1 eq) in THF (2 mL) at rt was added NaHMDS (0.23 mL of 1 M solution in THF, 0.23 mmol, 5 eq). After 30 min, 4-morpholinecarbonyl chloride (0.026 mL, 0.23 mmol, 5 eq) was added and the solution was stirred overnight. The solution was added to a 5 mL diatomaceous earth extraction tube loaded with aqueous ammonium chloride, and DCM was added, collected and concentrated. Purification by chromatography (8 g), eluting with 40 to 100% EA/hexanes, gave compound 2 (9.1 mg, 42%). $^1$H NMR (CHLOROFORM-d) δ: 7.31-7.40 (m, 2H), 7.17-7.22 (m, 2H), 7.04-7.09 (m, 2H), 7.01 (td, J=7.6, 1.3 Hz, 1H), 6.88 (dd, J=8.3, 1.0 Hz, 1H), 4.20-4.27 (m, 2H), 3.66 (br. s., 5H), 3.44-3.51 (m, 7H), 2.94-3.09 (m, 3H), 2.56 (dd, J=16.4, 7.1 Hz, 2H), 1.96-2.04 (m, 2H). ESI-MS (m/z): Calcd. for C26H28ClN3O4: 482.2 (M+1). found: 482.2.

Following the procedure described above for Example 1 and substituting the appropriate reagents, starting materials and purification methods known to those skilled in the art, the following compound was prepared:

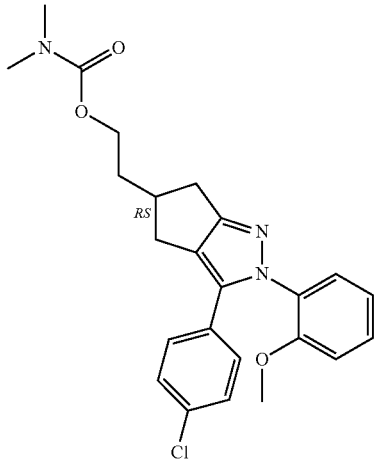

Cpd 3

Cpd 3: $^1$H NMR (CHLOROFORM-d) δ: 7.38 (dd, J=7.7, 1.6 Hz, 1H), 7.34 (td, J=7.9, 1.6 Hz, 1H), 7.17-7.22 (m, 2H), 7.05-7.09 (m, 2H), 7.01 (td, J=7.6, 1.3 Hz, 1H), 6.88 (dd, J=8.2, 1.1 Hz, 1H), 4.20 (t, J=6.6 Hz, 2H), 3.49 (s, 3H), 2.96-3.09 (m, 3H), 2.92 (s, 6H), 2.49-2.64 (m, 2H), 1.93-2.04 (m, 2H). ESI-MS (m/z): Calcd. for C24H26ClN3O3: 440.2 (M+1). found: 440.2.

Example 2

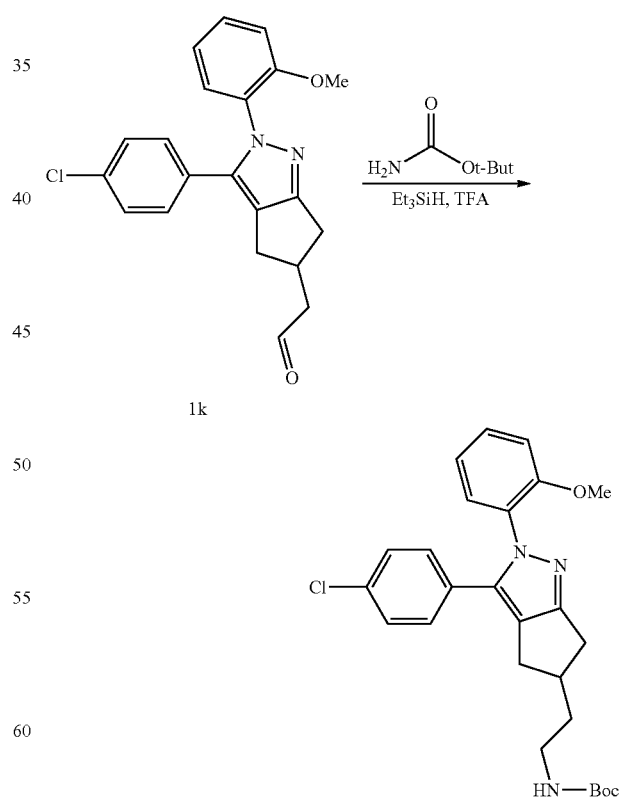

To a solution of compound 1k (23 mg, 0.06 mmol, 1 eq) in acetonitrile (2 mL) was added t-butylcarbamate (37 mg, 0.31 mmol, 4.95 eq), triethylsilane (0.05 mL, 0.32 mmol, 5.1 eq) and trifluoroacetic acid (0.016 mL, 0.21 mmol, 3.3 eq). The solution was heated to 50° C. overnight in a vial. The solution was cooled, ethyl acetate added, and the solution was washed sequentially with NaHCO₃ and brine. The organic phase was dried over MgSO₄, filtered, and concentrated. Purification by chromatography (8 g), eluting with 30 to 50% EA/hexanes, gave compound 13 (19 mg, 65%). ¹H NMR (CHLOROFORM-d) δ: 7.36-7.41 (m, 1H), 7.34 (t, J=8.0 Hz, 1H), 7.19 (d, J=8.6 Hz, 2H), 7.06 (d, J=8.3 Hz, 2H), 7.01 (t, J=7.6 Hz, 1H), 6.88 (d, J=8.3 Hz, 1H), 4.58 (br. s., 1H), 3.49 (s, 3H), 3.24 (d, J=6.1 Hz, 2H), 2.89-3.08 (m, 3H), 2.48-2.61 (m, 2H), 1.77-1.91 (m, 2H), 1.46 (s, 9H). ESI-MS (m/z): Calcd. for C26H30ClN3O3: 468.2 (M+1). found: 468.2.

Following the procedure described above for Example 2, substituting acetamide for t-butylcarbamate, the following compound was prepared:

Cpd 12

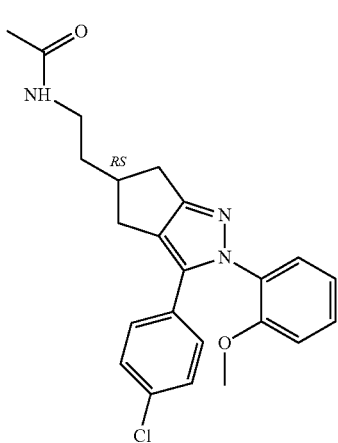

Cpd 12: ¹H NMR (CHLOROFORM-d) δ: 7.32-7.40 (m, 2H), 7.17-7.24 (m, 2H), 7.04-7.11 (m, 2H), 6.97-7.04 (m, 1H), 6.90 (d, J=7.6 Hz, 1H), 5.56 (br. s., 1H), 3.52 (s, 3H), 3.34-3.43 (m, 2H), 2.92-3.13 (m, 3H), 2.47-2.65 (m, 2H), 2.02 (s, 3H), 1.6-1.8 (m, 2H). ESI-MS (m/z): Calcd. for C23H24ClN3O2: 410.2 (M+1). found: 410.2.

Example 3

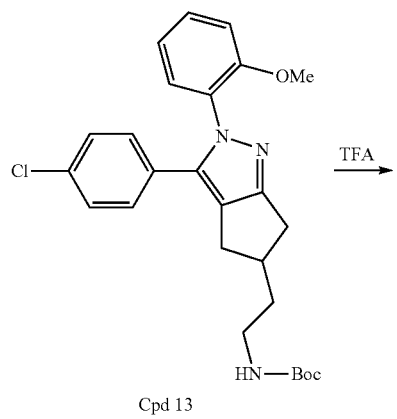

Cpd 13

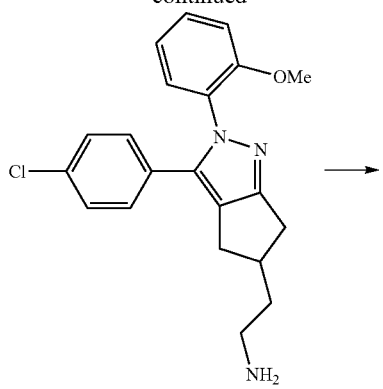

3a

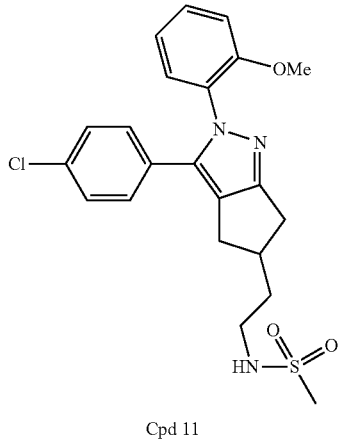

Cpd 11

A. A solution of compound 13 (13 mg, 0.03 mmol, 1 eq) in DCM (5 mL) and trifluoroacetic acid (1 mL) was stirred for 2 hrs and concentrated. DCM was added, the organics washed with NaHCO₃, dried over MgSO₄, filtered, and concentrated to give compound 3a (11 mg, 100%). ¹H NMR (CHLOROFORM-d) δ: 8.11 (br. s., 2H), 7.38 (t, J=7.8 Hz, 1H), 7.28 (d, J=7.6 Hz, 1H), 7.16-7.24 (m, J=8.3 Hz, 2H), 7.01-7.09 (m, J=8.3 Hz, 2H), 6.98 (t, J=7.5 Hz, 1H), 6.90 (d, J=8.3 Hz, 1H), 3.52 (s, 3H), 2.83-3.21 (m, 5H), 2.49 (br. s., 2H), 1.83-2.08 (m, 2H). Calcd. for C21H22ClN3O: 368.2 (M+1). found: 368.2.

B. To a solution of compound 3a (10 mg, 0.027 mmol, 1 eq) in DCM (2 mL) was added triethylamine (0.019 mL, 0.14 mmol, 5 eq) and methanesulfonyl chloride (0.01 mL, 0.14 mmol, 5 eq). After 1 hr, the solution was concentrated. Purification by chromatography (8 g), eluting with 50 to 100% EA/hexanes, gave compound 11 (3 mg, 25%). ¹H NMR (CHLOROFORM-d) δ: 7.30-7.41 (m, 2H), 7.17-7.23 (m, 2H), 7.04-7.10 (m, 2H), 6.97-7.04 (m, 1H), 6.88 (d, J=8.3 Hz, 1H), 4.23-4.33 (m, 1H), 3.49 (s, 3H), 3.26 (q, J=6.7 Hz, 2H), 2.94-3.09 (m, 6H), 2.46-2.62 (m, 2H), 1.93 (q, J=6.7 Hz, 2H). ESI-MS (m/z): Calcd. for C22H24ClN3O3S: 446.1 (M+1). found: 446.1.

Following the procedure described above for Example 3 and substituting the appropriate reagents, starting materials and purification methods known to those skilled in the art, the following compounds were prepared:

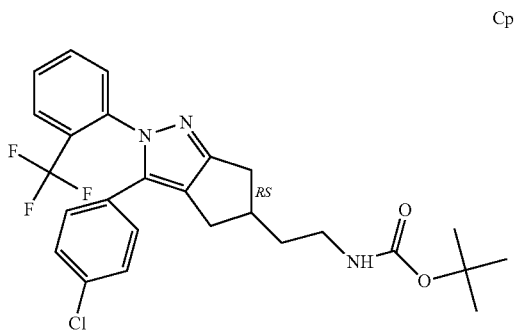
Cpd 20
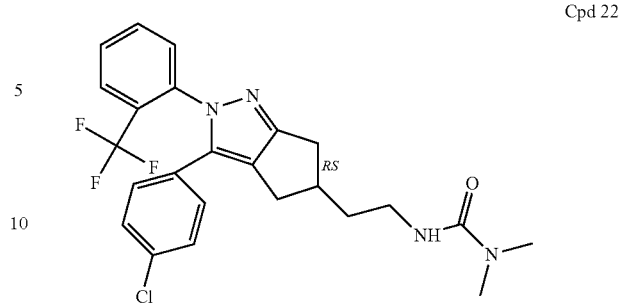
Cpd 22
Cpd 20: ¹H NMR (CHLOROFORM-d) δ: 7.75-7.81 (m, 1H), 7.49-7.57 (m, 2H), 7.16-7.25 (m, 3H), 6.97-7.03 (m, 2H), 4.58 (br. s., 1H), 3.24 (br. s., 2H), 2.90-3.08 (m, 3H), 2.55 (dd, J=14.7, 7.1 Hz, 2H), 1.84 (q, J=6.8 Hz, 2H), 1.46 (s, 9H). ESI-MS (m/z): Calcd. for C26H27ClF3N3O2: 506.2 (M+1). found: 506.2.
Cpd 22: ¹H NMR (CHLOROFORM-d) δ: 7.75-7.82 (m, 1H), 7.49-7.57 (m, 2H), 7.15-7.25 (m, 3H), 6.96-7.03 (m, 2H), 4.42 (br. s., 1H), 3.31-3.41 (m, 2H), 2.93-3.09 (m, 3H), 2.92 (s, 6H), 2.49-2.62 (m, 2H), 1.82-1.93 (m, 2H). ESI-MS (m/z): Calcd. for C24H24ClF3N4O: 477.2 (M+1). found: 477.2.
Example 4
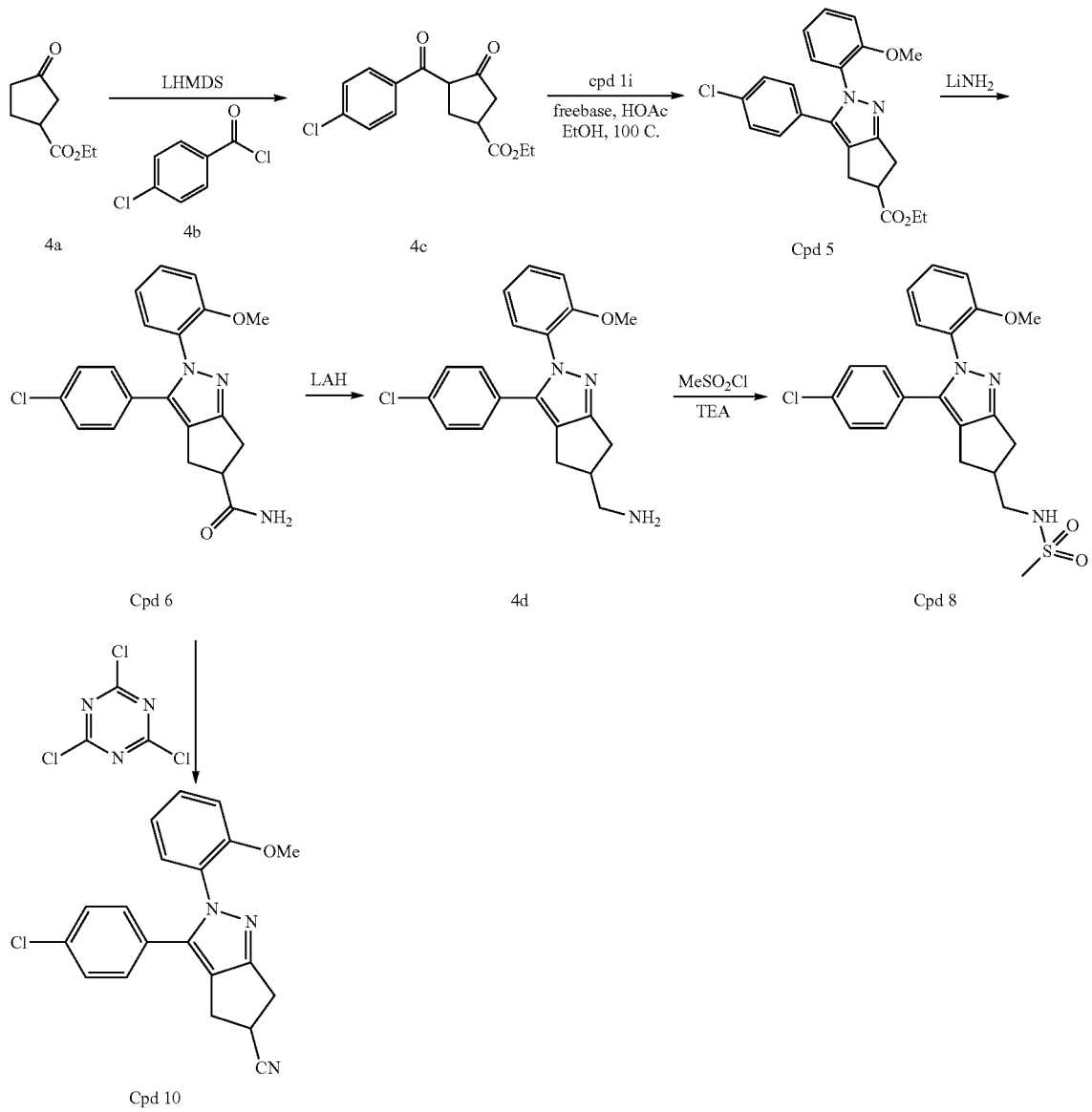

A. To a solution of LHMDS (15.8 mL of a 1 M solution in THF, 15.8 mmol, 1.6 eq) in THF (15 mL) at −78° C. under Ar was added ethyl 3-oxocyclopentanecarboxylate (4a) (1.55 g, 9.9 mmol, 1 eq) in THF (15 mL) dropwise over 30 min. After 30 additional minutes, a solution of 4-chlorobenzoyl chloride (4b) (1.25 mL, 9.9 mmol, 1 eq) in THF (10 mL) was added. After 1 hr, water and NH$_4$Cl were added and the reaction mixture was stirred overnight. The aqueous layer was extracted with ether, the organics combined, dried over MgSO$_4$, filtered, and concentrated. Purification by chromatography (80 g), eluting with 10 to 40% EA/hexanes, gave compound 4c (83 mg, 3%). $^1$H NMR (tautomeric mix, MeOH-d4) δ: 7.67-7.74 (m, 2H), 7.43-7.52 (m, 2H), 4.15-4.28 (m, 2H), 3.06-3.24 (m, 3H), 2.48-2.94 (m, 2H), 1.25-1.35 (m, 3H). Calcd. for C15H15ClO4: 295.1 (M+1). found: 294.9.

B. To a solution of compound 4c (83 mg, 0.28 mmol, 1 eq) in acetic acid (3 mL) at 80° C. was added 2-methoxyphenylhydrazine free base (11) (43 mg, 0.31 mmol, 1.1 eq). After 30 min, the solution was concentrated. Purification by chromatography (8 g), eluting with 10 to 25% EA/hexanes, gave compound 5 (62 mg, 56%). $^1$H NMR (CHLOROFORM-d) δ: 7.31-7.40 (m, 2H), 7.17-7.23 (m, 2H), 7.05-7.10 (m, 2H), 7.01 (td, J=7.7, 1.3 Hz, 1H), 6.88 (dd, J=8.3, 1.0 Hz, 1H), 4.22 (q, J=7.1 Hz, 2H), 3.72-3.82 (m, 1H), 3.50 (s, 3H), 3.07-3.22 (m, 4H), 1.31 (t, J=7.2 Hz, 3H). ESI-MS (m/z): Calcd. for C22H21ClN2O3: 397.1 (M+1). found: 397.1.

C. To lithium amide (45 mg, 1.95 mmol, 13 eq) in a vial was added a solution of compound 5 (60 mg, 0.15 mmol, 1 eq) in THF (2 mL) and the suspension was heated to 65° C. overnight. Methanol, water and 1 N HCl were added and the reaction mixture was extracted with ethyl acetate. The organics were combined, dried over MgSO$_4$, filtered, and concentrated. Purification by chromatography (8 g), eluting with 2 to 5% methanol/DCM, gave compound 6 (23 mg, 42%). $^1$H NMR (CHLOROFORM-d) δ: 7.31-7.40 (m, 2H), 7.17-7.23 (m, 2H), 7.04-7.09 (m, 2H), 7.01 (td, J=7.7, 1.3 Hz, 1H), 6.88 (dd, J=8.3, 1.0 Hz, 1H), 5.66 (br. s., 2H), 3.61-3.74 (m, 1H), 3.50 (s, 3H), 3.02-3.23 (m, 4H). ESI-MS (m/z): Calcd. for C20H18ClN3O2: 368.1 (M+1). found: 368.1.

D. To a solution of compound 6 (22 mg, 0.06 mmol, 1 eq) in THF at rt was added LAH (0.18 mL of a 1 M solution in THF, 0.18 mmol, 3 eq). After 1 hr, additional LAH (0.18 mL) was added. After 3 hrs, added saturated sodium potassium tartrate, stirred 30 min, and added water. The reaction mixture was extracted with ether, dried over MgSO$_4$, filtered, and concentrated. Purification by chromatography (8 g), eluting with 2 to 10% methanol/DCM and NH$_3$ (1%) gave compound 4d as a mixture of the desired product and loss of Cl (5 mg, 24%).

E. To a solution of compound 4d (5 mg, 0.014 mmol, 1 eq) in DCM (2 mL) was added triethylamine (0.01 mL, 0.07 mmol, 5 eq) and methanesulfonyl chloride (0.006 mL, 0.07 mmol, 5 eq). After stirring overnight, the solution was concentrated. Purification by HPLC, eluting with 20 to 80 to 100% acetonitrile/water, gave compound 8 (1 mg, 17%). $^1$H NMR (CHLOROFORM-d) δ: 7.40 (dd, J=15.9, 1.8 Hz, 1H), 7.32 (dd, J=7.8, 1.5 Hz, 1H), 7.21-7.25 (m, 2H), 7.05-7.10 (m, 2H), 7.01 (td, J=7.6, 1.1 Hz, 1H), 6.89-6.94 (m, 1H), 4.46 (br. s., 1H), 3.55 (s, 3H), 3.32-3.40 (m, 2H), 3.02-3.26 (m, 2H), 3.01 (s, 3H), 2.71 (ddd, J=15.4, 9.6, 5.6 Hz, 2H). ESI-MS (m/z): Calcd. for C21H22ClN3O3S: 432.1 (M+1). found: 432.1.

F. To a solution of compound 6 (7 mg, 0.02 mmol, 1 eq) in DMF (2 mL) was added cyanuric chloride (11 mg, 0.06 mmol, 3 eq). After 1 hr, added water was added and the reaction mixture was extracted with DCM. The organic phase was dried over MgSO$_4$, filtered, and concentrated. Purification by HPLC, eluting with 20 to 80 to 100% acetonitrile/water, gave compound 10 (2 mg, 29%). $^1$H NMR (CHLOROFORM-d) δ: 7.36-7.42 (m, 1H), 7.34 (dd, J=7.7, 1.6 Hz, 1H), 7.21-7.26 (m, 2H), 6.99-7.08 (m, 3H), 6.91 (dd, J=8.3, 1.0 Hz, 1H), 3.75 (quin, J=7.9 Hz, 1H), 3.54 (s, 3H), 3.34-3.43 (m, 1H), 3.15-3.34 (m, 3H). ESI-MS (m/z): Calcd. for C20H16ClN3O: 350.1 (M+1). found: 350.1.

Following the procedure described above for Example 4 and substituting the appropriate reagents, starting materials and purification methods known to those skilled in the art, the following compounds were prepared:

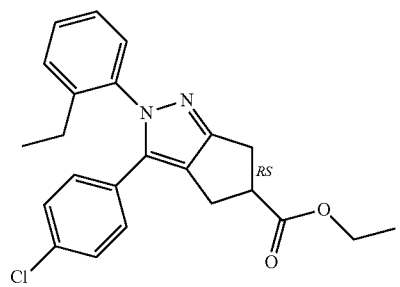

Cpd 14

Cpd 14: $^1$H NMR (CHLOROFORM-d) δ: 7.32-7.39 (m, 1H), 7.30 (d, J=6.8 Hz, 1H), 7.15-7.25 (m, 4H), 6.99-7.04 (m, 2H), 4.23 (q, J=7.2 Hz, 2H), 3.79 (quin, J=8.4 Hz, 1H), 3.11-3.25 (m, 4H), 2.36 (q, J=7.7 Hz, 2H), 1.32 (t, J=7.1 Hz, 3H), 1.00 (t, J=7.6 Hz, 3H). ESI-MS (m/z): Calcd. for C23H23ClN2O2: 395.2 (M+1). found: 395.2.

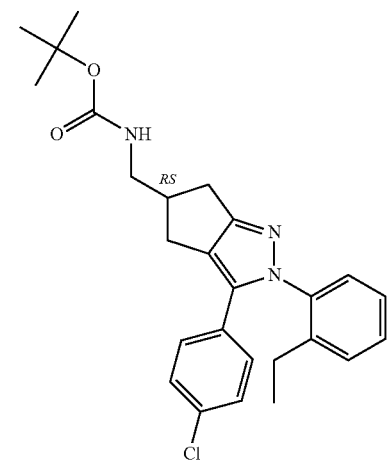

Cpd 16

Cpd 16: $^1$H NMR (CHLOROFORM-d) δ: 7.50-7.88 (m, 1H), 7.39-7.48 (m, 1H), 7.27-7.36 (m, 3H), 7.18-7.25 (m, 2H), 7.00-7.07 (m, 2H), 2.96-3.46 (m, 5H), 2.56-2.78 (m, 2H), 2.27 (br. s., 2H), 1.38-1.55 (m, 9H), 0.98 (t, J=7.6 Hz, 3H). ESI-MS (m/z): Calcd. for C26H30ClN3O2: 452.2 (M+1). found: 452.2.

Cpd 17

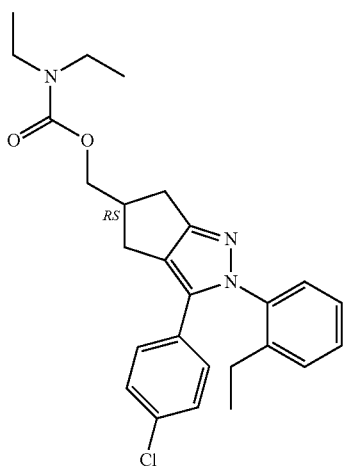

Cpd 17: ¹H NMR (CHLOROFORM-d) δ: 7.32-7.39 (m, 1H), 7.30 (d, J=6.6 Hz, 1H), 7.15-7.25 (m, 4H), 6.98-7.04 (m, 2H), 4.17-4.29 (m, 2H), 3.15-3.39 (m, 5H), 3.02 (ddd, J=15.7, 8.5, 2.1 Hz, 2H), 2.69 (ddd, J=15.6, 13.8, 6.2 Hz, 2H), 2.36 (q, J=7.6 Hz, 2H), 1.12 (br. s., 6H), 1.00 (t, J=7.6 Hz, 3H). ESI-MS (m/z): Calcd. for C26H30ClN3O2: 452.2 (M+1). found: 452.2.

Cpd 18

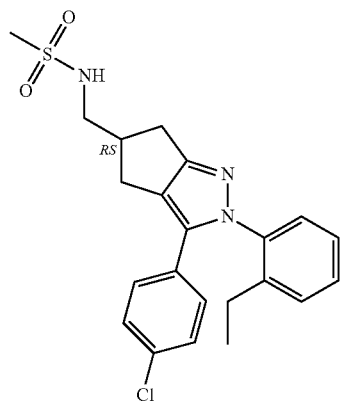

Cpd 18: ¹H NMR (CHLOROFORM-d) δ: 7.36 (td, J=7.3, 1.8 Hz, 1H), 7.30 (d, J=6.6 Hz, 1H), 7.16-7.25 (m, 4H), 6.97-7.04 (m, 2H), 4.49 (t, J=6.3 Hz, 1H), 3.36 (t, J=6.7 Hz, 2H), 3.12-3.24 (m, 1H), 3.02-3.11 (m, 2H), 3.00 (s, 3H), 2.65 (ddd, J=22.4, 15.8, 6.1 Hz, 2H), 2.35 (q, J=7.6 Hz, 2H), 1.00 (t, J=7.6 Hz, 3H). ESI-MS (m/z): Calcd. for C22H24ClN3O2S: 430.1 (M+1). found: 430.1.

Cpd 19

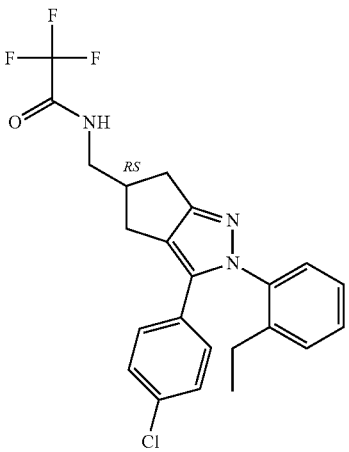

Cpd 19: ¹H NMR (CHLOROFORM-d) δ: 7.33-7.40 (m, 1H), 7.28-7.33 (m, 1H), 7.14-7.25 (m, 4H), 6.96-7.04 (m, 2H), 6.69 (br. s., 1H), 3.57 (tq, J=13.1, 6.7 Hz, 2H), 3.14-3.26 (m, 1H), 3.05 (ddd, J=15.5, 8.1, 2.9 Hz, 2H), 2.61 (ddd, J=15.3, 9.2, 5.8 Hz, 2H), 2.35 (q, J=7.6 Hz, 2H), 1.00 (t, J=7.6 Hz, 3H). ESI-MS (m/z): Calcd. for C23H21ClF3N3O: 448.1 (M+1). found: 448.1.

Example 5

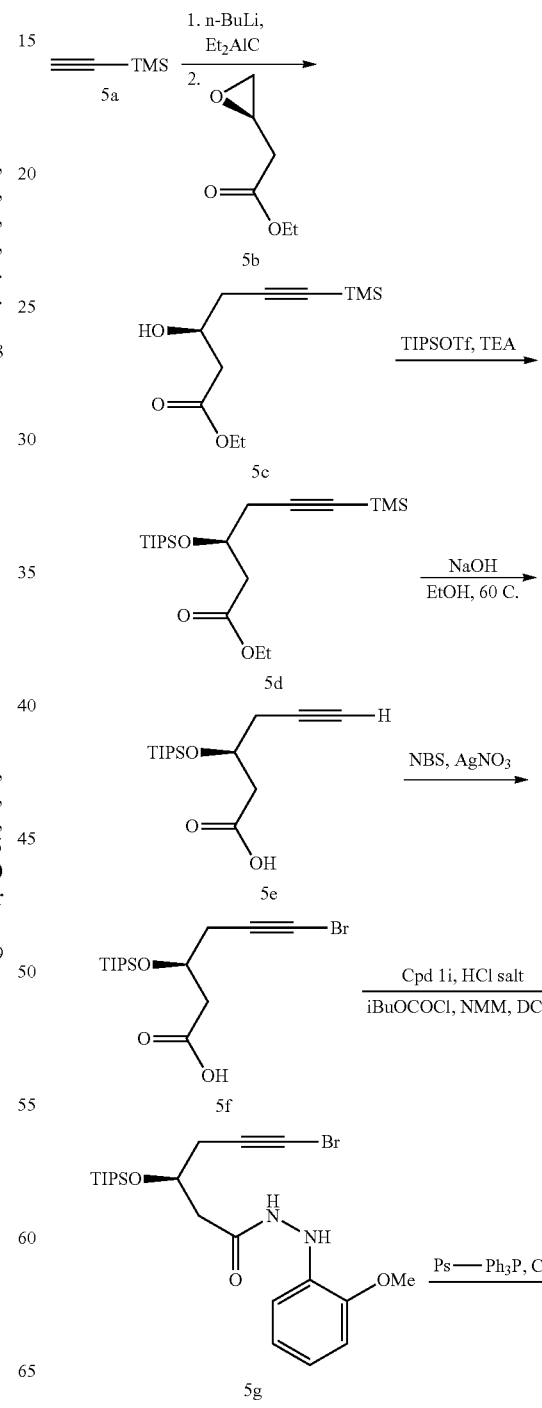

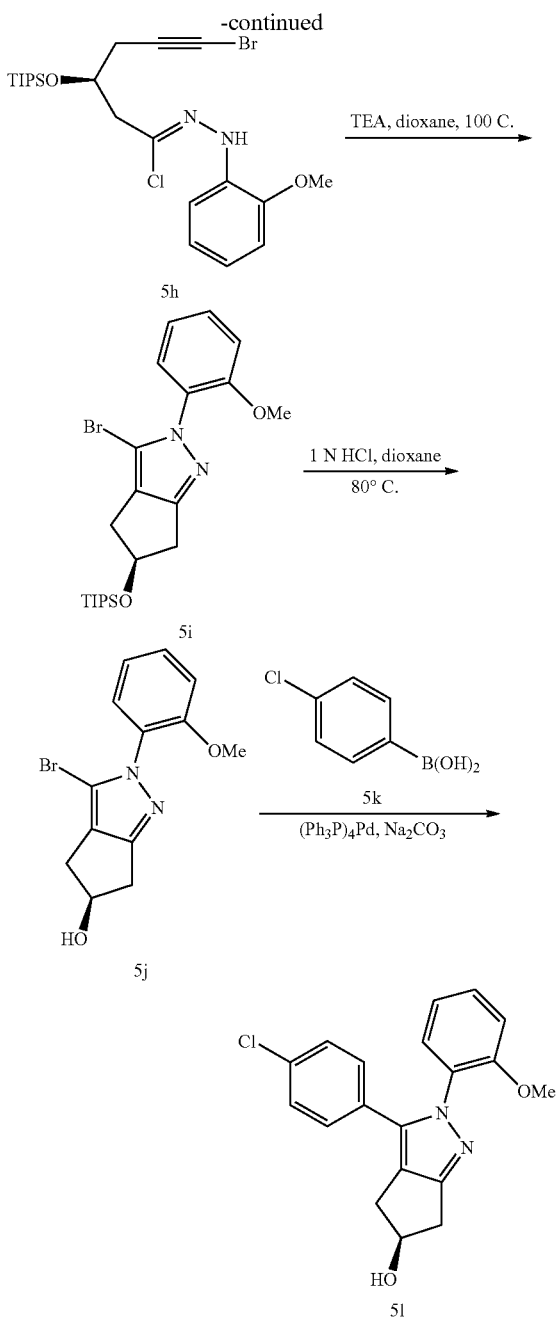

A. To a solution of trimethylsilyl acetylene (5a) (1.41 mL, 10.14 mmol, 1.1 eq) in toluene (24 mL) at −45° C. under Ar was added n-BuLi (4.06 mL of a 2.5 M solution in hexanes, 10.14 mmol, 1.1 eq). A suspension formed, and after 10 min, the mixture was warmed to 0° C. After 10 min, diethylaluminum chloride (10.14 mL of a 1 M solution in hexanes, 10.14 mmol, 1.1 eq) was added. After 1 hr, (R)-ethyloxiranyl acetate (5b) (1.0 mL, 9.22 mmol, 1 eq) in toluene (10 mL) was added and the mixture stirred at 0° C. for 1 hr. To the suspension at 0° C. was added dropwise 3 mL saturated NH$_4$Cl, followed by the dropwise addition of 4 mL 1 N HCl to precipitate the aluminum salts. After stirring overnight, the suspension was filtered through diatomaceous earth, with ethyl acetate washings. The filtrate was washed with brine, dried over MgSO$_4$, filtered, and concentrated. Purification by column chromatography (40 g), eluting with 10 to 20% EA/hexanes, gave compound 5c (1.28 g, 61%). $^1$H NMR (CHLOROFORM-d) δ: 4.11-4.24 (m, 3H), 3.03 (d, J=4.5 Hz, 1H), 2.63-2.72 (m, 1H), 2.41-2.59 (m, 3H), 1.29 (t, J=7.2 Hz, 3H), 0.16 (s, 9H).

B. To a solution of compound 5c (1.28 g, 5.58 mmol, 1 eq) in DCM (20 mL) at 0° C. was added diisopropylethylamine (1.36 mL, 7.82 mmol, 1.4 eq) followed by triisopropylsilyl trifluoromethanesulfonate (1.81 mL, 6.7 mmol, 1.2 eq). Upon addition of water, the reaction mixture was extracted with DCM, dried over MgSO$_4$, filtered, and concentrated to compound 5d. To a solution of compound 5d in ethanol (20 mL) was added 1 N NaOH (10 mL) and the reaction heated to 50° C. overnight, followed by additional heating at 80° C. for 4 hr. The reaction mixture was made acidic by the addition of 1N HCl. The ethanol was removed, the aqueous mixture was extracted with DCM, the organics combined, dried over MgSO$_4$, filtered, and concentrated. Purification by column chromatography (80 g), eluting with 0 to 40% EA/hexanes, gave compound 5e (1.51 g, 95%). $^1$H NMR (CHLOROFORM-d) δ: 4.37-4.45 (m, 1H), 2.83 (dd, J=15.4, 5.3 Hz, 1H), 2.68 (dd, J=15.5, 5.9 Hz, 1H), 2.51-2.56 (m, 2H), 2.03-2.05 (m, 1H), 1.03-1.10 (m, 21H).

C. To a solution of compound 5e (1100 mg, 3.87 mmol, 1 eq) in acetone (20 mL) at rt was added silver nitrate (66 mg, 0.39 mmol, 0.1 eq) followed by N-bromosuccinimide (757 mg, 4.25 mmol, 1.1 eq). After 3 hrs, water and 1N HCl were sequentially added to the solution. The resultant precipitate was dissolved in DCM, washed with water, and the organic phase was dried, filtered, and concentrated to compound 5f (1.53 g, ~90% pure, 98% yield). $^1$H NMR (CHLOROFORM-d) δ: 4.39 (t, J=5.9 Hz, 1H), 2.59-2.84 (m, 3H), 2.54 (d, J=6.1 Hz, 1H), 0.96-1.15 (m, 21H).

D. To a solution of compound 5f (1.53 g, 3.79 mmol, 1 eq) in DCM (20 mL) at rt under Ar was added N-methylmorpholine (0.44 mL, 3.98 mmol, 1.05 eq) followed by isobutylchloroformate (0.52 mL, 3.98 mmol, 1.05 eq). After 20 min, a solution of compound 1i-HCl (794 mg, 4.55 mmol, 1.2 eq) and N-methylmorpholine (0.50 mL, 4.55 mmol, 1.2 eq) in DCM (10 mL) was added and the solution stirred for 60 min. Water and 1 N HCl were sequentially added, the reaction mixture was extracted with DCM, the organics combined, washed with NaHCO$_3$ and brine, dried over MgSO$_4$, filtered, and concentrated. Purification by column chromatography (80 g), eluting with 10 to 20 to 25% EA/hexanes, gave compound 5g (1.42 g, 78%). ESI-MS (m/z): Calcd. for C22H35BrN2O3Si: 483.2 (M+1). found: 483.0.

E. In a 1-L 3-neck round bottom flask equipped with an overhead stirrer, heating mantel, septa, and temperature probe was added (S)-6-bromo-N'-(2-methoxyphenyl)-3-(triisopropylsilyloxy)hexanes-5-ynehydrazide (5g) (26.27 g, 54.3 mmol, 1 eq), acetonitrile (550 mL) and carbon tetrachloride (21.0 mL, 217 mmol, 4 eq). One portion of polymer-bound triphenylphosphine (3 mmol/g P, 73.6 g, 221 mmol, 4 eq) was added at room temperature and the suspension was stirred for 1 h. The color of the polymer remained brown (unchanged) and no reaction was detected by TLC (30% EtOAc in heptane). The reaction was heated to 50° C. for 30 min, then the reaction was allowed to cool to room temperature for 1 h, filtered through silica gel (150 g) and washed with acetonitrile (600 mL), whereby a whitish substance came through the filter pad. After filtration and evaporation there was collected an orange oil that was still cloudy; EtOAc (100 mL) was added, dried with Na$_2$SO$_4$, filtered and evaporated to provide compound 5h (21 g) as an orange oil in 75% yield. The crude product was carried on to the next reaction without further purification. $^1$H NMR (CHLOROFORM-d) δ: 8.07 (s, 1H), 7.32 (d, J=7.6 Hz, 1H), 6.92 (dt, J=8.2, 4.2 Hz, 1H), 6.84 (d, J=3.7 Hz, 2H), 4.39 (quin, J=5.8 Hz, 1H), 3.89 (s, 3H), 2.85-

3.00 (m, 2H), 2.46-2.60 (m, 2H), 1.01-1.12 (m, 21H). ESI-MS (m/z): Calcd. for C22H34BrClN2O2Si: 464.1 (M-36). found: 464.3.

F. Compound 5h (385 mg, 0.77 mmol, 1 eq) and triethylamine (0.43 mL, 3.07 mmol, 4 eq) in dioxane (10 mL) were heated at 90° C. for 20 hrs. Water was added to the reaction mixture, and the mixture was extracted with DCM, dried over MgSO4, filtered, and concentrated. Purification by column chromatography (40 g), eluting with 5 to 10% EA/hexanes, gave compound 5i (300 mg, 65%). ¹H NMR (CHLOROFORM-d) δ: 7.42 (td, J=8.0, 1.8 Hz, 1H), 7.28-7.34 (m, 1H), 6.99-7.06 (m, 2H), 5.05 (t, J=6.2 Hz, 1H), 3.82 (s, 3H), 3.18 (dd, J=15.7, 7.3 Hz, 1H), 3.04 (dd, J=15.0, 7.2 Hz, 1H), 2.83 (dd, J=15.8, 6.2 Hz, 1H), 2.66 (dd, J=15.0, 5.9 Hz, 1H), 1.05-1.18 (m, 21H). ESI-MS (m/z): Calcd. for C22H33BrN2O2Si: 465.2 (M+1). found: 465.2.

F. To a solution of compound 5i (197 mg, 0.42 mmol, 1 eq) in dioxane (5 mL) was added 1 N HCl (1 mL), and the reaction was heated to 80° C. for 3 hrs. The solution was extracted with DCM, dried over MgSO4, filtered, and concentrated to give compound 5j (124 mg, 95%). ¹H NMR (CHLOROFORM-d) δ: 7.43 (t, J=7.9 Hz, 1H), 7.32 (d, J=7.3 Hz, 1H), 7.00-7.08 (m, 2H), 4.94-5.04 (m, 1H), 3.83 (s, 3H), 3.21 (dd, J=16.3, 6.5 Hz, 1H), 3.08 (dd, J=15.6, 6.4 Hz, 1H), 2.82 (dd, J=16.4, 3.9 Hz, 1H), 2.66 (dd, J=15.7, 3.7 Hz, 1H), 1.97 (d, J=6.1 Hz, 1H). ESI-MS (m/z): Calcd. for C13H13BrN2O2: 309.2 (M+1). found: 309.0.

G. To a solution of 4-chlorophenylboronic acid (5k) (76 mg, 0.49 mmol, 1.5 eq) in dimethoxyethane (1 mL) was added 2 M Na2CO3 (0.1 mL), compound 5j (100 mg, 0.32 mmol, 1 eq), and (Ph3P)4Pd (19 mg, 0.016 mmol, 0.05 eq). The solution was degassed by bubbling Argon through the solution, then heated to 85° C. for 3 days. Water and brine were added to the reaction mixture which was then extracted with ethyl acetate. The combined organic phases were dried over MgSO4, filtered, and concentrated. Purification by column chromatography (12 g), eluting with 50 to 100% EA/hexanes, gave compound 5l (80 mg, 71%). ¹H NMR (CHLOROFORM-d) δ: 7.39 (dd, J=7.7, 1.6 Hz, 1H), 7.31-7.37 (m, 1H), 7.17-7.25 (m, J=8.3 Hz, 2H), 7.05-7.11 (m, J=8.3 Hz, 2H), 7.02 (td, J=7.6, 1.1 Hz, 1H), 6.88 (d, J=8.1 Hz, 1H), 4.97-5.11 (m, 1H), 3.49 (s, 3H), 3.14-3.29 (m, 2H), 2.70-2.90 (m, 2H), 2.08 (d, J=5.3 Hz, 1H). ESI-MS (m/z): Calcd. for C19H17ClN2O2: 341.1 (M+1). found: 341.2.

Example 6

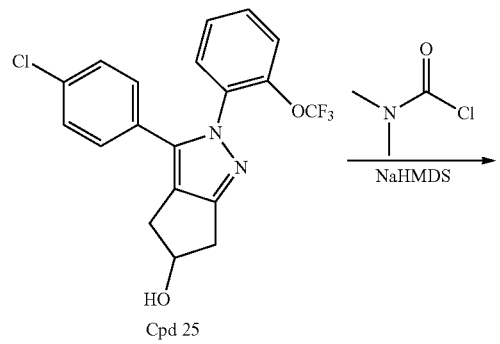

Cpd 25

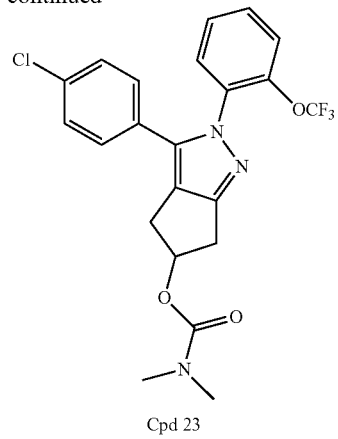

Cpd 23

A. Compound 25 was prepared according to the procedures described in Example 5, substituting (2-(trifluoromethoxy)phenyl)hydrazine for compound 1i in Step D.

B. To a solution of compound 25 (22 mg, 0.056 mmol, 1 eq) in THF (1.5 mL) was added NaHMDS (0.28 mL of a 1 M solution in THF, 0.28 mmol, 5 eq) followed by dimethylcarbamoyl chloride (0.026 mL, 0.28 mmol, 5 eq). After 2 hrs, saturated NH4Cl was added and the solution was poured onto a 5 mL extraction tube filled with diatomaceous earth, washed through with DCM, dried, filtered, and concentrated. Purification by chromatography (8 g), eluting with 20 to 40% EA/hexanes, gave compound 23 (14.9 mg, 57%). ¹H NMR (CHLOROFORM-d) δ: 7.52-7.58 (m, 1H), 7.33-7.46 (m, 2H), 7.19-7.28 (m, 3H), 7.01-7.08 (m, 2H), 5.77 (tt, J=7.2, 3.6 Hz, 1H), 3.25-3.37 (m, 2H), 2.83-3.01 (m, 8H). ESI-MS (m/z): Calcd. for C22H19ClF3N3O3: 466.1 (M+1). found: 466.1.

Following the procedure described above for Example 6 and substituting the appropriate reagents, starting materials and purification methods known to those skilled in the art, the following compounds were prepared:

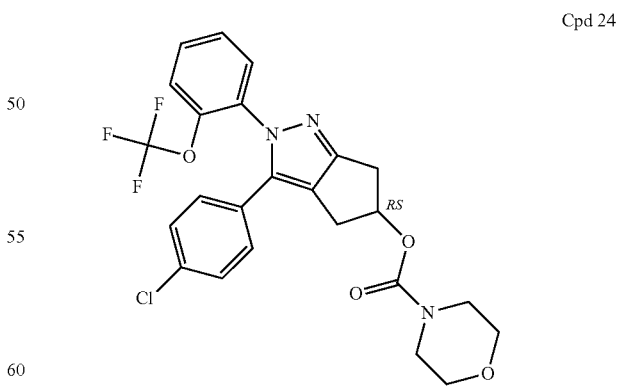

Cpd 24

Cpd 24: ¹H NMR (CHLOROFORM-d) δ: 7.55 (dd, J=7.5, 1.9 Hz, 1H), 7.34-7.46 (m, 2H), 7.20-7.29 (m, 3H), 7.00-7.07 (m, 2H), 5.80 (tt, J=7.0, 3.7 Hz, 1H), 3.40-3.76 (m, 8H), 3.33 (dd, J=16.7, 7.1 Hz, 2H), 2.84-3.00 (m, 2H). ESI-MS (m/z): Calcd. for C24H21ClF3N3O4: 508.1 (M+1). found: 508.1.

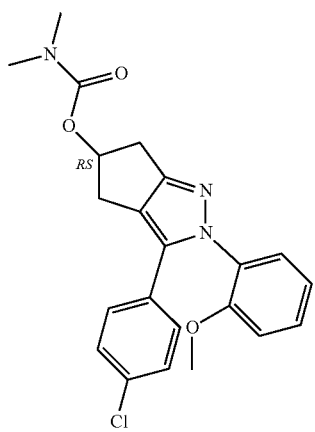

Cpd 28

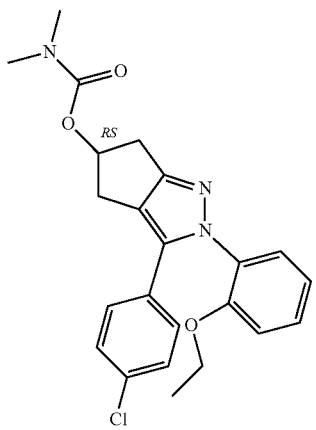

Cpd 30

Cpd 28: ¹H NMR (CHLOROFORM-d) δ: 7.39 (dd, J=7.7, 1.6 Hz, 1H), 7.35 (td, J=8.0, 1.8 Hz, 1H), 7.17-7.22 (m, 2H), 7.05-7.10 (m, 2H), 7.02 (td, J=7.6, 1.3 Hz, 1H), 6.89 (dd, J=8.3, 1.0 Hz, 1H), 5.73-5.80 (m, 1H), 3.50 (s, 3H), 3.29-3.39 (m, 2H), 2.84-3.00 (m, 8H). ESI-MS (m/z): Calcd. for C22H22ClN3O3: 412.1 (M+1). found: 412.1.

Cpd 30: ¹H NMR (CHLOROFORM-d) δ: 7.49 (dd, J=7.8, 1.8 Hz, 1H), 7.32 (td, J=8.0, 1.8 Hz, 1H), 7.16-7.23 (m, 2H), 7.06-7.13 (m, 2H), 7.04 (td, J=7.6, 1.1 Hz, 1H), 6.80-6.86 (m, 1H), 5.72-5.81 (m, 1H), 3.71 (br. s., 2H), 3.33 (dd, J=16.5, 7.2 Hz, 2H), 2.80-3.02 (m, 8H), 0.98 (t, J=6.9 Hz, 3H). ESI-MS (m/z): Calcd. for C23H24ClN3O3: 426.2 (M+1). found: 426.2.

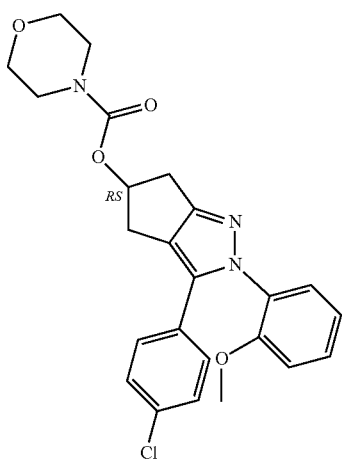

Cpd 29

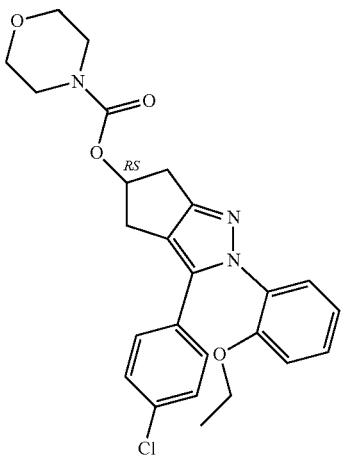

Cpd 31

Cpd 29: ¹H NMR (CHLOROFORM-d) δ: 7.32-7.42 (m, 2H), 7.17-7.23 (m, 2H), 7.05-7.10 (m, 2H), 7.02 (td, J=7.7, 1.3 Hz, 1H), 6.90 (dd, J=8.3, 1.0 Hz, 1H), 5.80 (dt, J=7.3, 3.6 Hz, 1H), 3.66 (br. s., 4H), 3.50 (s, 7H), 3.29-3.40 (m, 2H), 2.85-3.01 (m, 2H). ESI-MS (m/z): Calcd. for C24H24ClN3O4: 454.2 (M+1). found: 454.2.

Cpd 31: ¹H NMR (CHLOROFORM-d) δ: 7.49 (dd, J=7.8, 1.5 Hz, 1H), 7.33 (td, J=7.9, 1.6 Hz, 1H), 7.16-7.23 (m, 2H), 7.06-7.11 (m, 2H), 7.04 (td, J=7.6, 1.1 Hz, 1H), 6.80-6.87 (m, 1H), 5.80 (tt, J=7.1, 3.8 Hz, 1H), 3.57-3.91 (m, 6H), 3.49 (br. s., 4H), 3.27-3.42 (m, 2H), 2.81-3.02 (m, 2H), 0.98 (t, J=7.1 Hz, 3H). ESI-MS (m/z): Calcd. for C25H26ClN3O4: 468.2 (M+1). found: 468.2.

Example 7

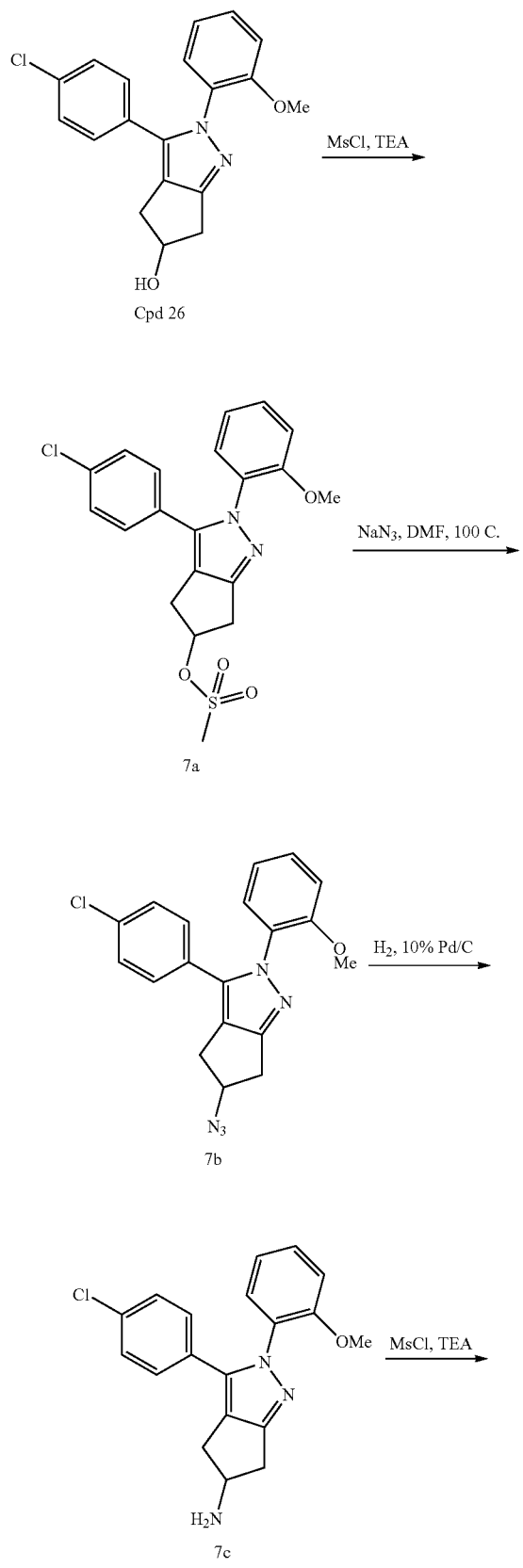

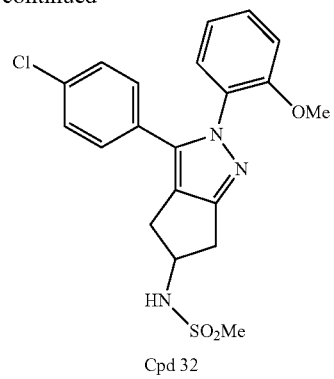

Cpd 32

A. Compound 26 was prepared according to the procedures described in Example 5, substituting the appropriate racemic starting materials.

B. To compound 26 (200 mg, 0.53 mmol, 1 eq) in DCM (5 mL) at rt was added triethylamine (0.15 mL, 1.06 mmol, 2 eq) followed by methanesulfonyl chloride (0.062 mL, 0.79 mmol, 1.5 eq). After stirring for 2 hrs, DCM was added. The organic phase was washed with water, dried over $MgSO_4$, filtered, and concentrated. Purification by column chromatography (24 g), eluting with 30 to 60% EA/hexanes, gave compound 7a (230 mg, 99%). $^1$H NMR (CHLOROFORM-d) δ: 7.32-7.41 (m, 2H), 7.19-7.24 (m, 2H), 6.99-7.09 (m, 3H), 6.89 (d, J=8.3 Hz, 1H), 5.73-5.83 (m, 1H), 3.50 (s, 3H), 3.38 (ddd, J=16.5, 6.8, 3.8 Hz, 2H), 3.15 (dt, J=16.5, 4.4 Hz, 2H), 3.08 (s, 3H). ESI-MS (m/z): Calcd. for C20H19ClN2O4S: 419.1 (M+1). found: 419.1.

C. To compound 7a (220 mg, 0.53 mmol, 1 eq) in DMF (5 mL) at rt was added sodium azide (52 mg, 0.79 mmol, 1.5 eq) and the solution was warmed to 100° C. After 1 hr the reaction was cooled, water was added, and the aqueous phase was extracted with DCM. The combined organic phases were dried over $MgSO_4$, filtered, and concentrated to compound 7b (184 mg, 95%). $^1$H NMR (CHLOROFORM-d) δ: 7.31-7.42 (m, 2H), 7.22 (d, J=8.6 Hz, 2H), 6.99-7.10 (m, 3H), 6.88 (d, J=7.8 Hz, 1H), 4.61-4.73 (m, 1H), 3.50 (s, 3H), 3.16-3.30 (m, 2H), 2.83-2.98 (m, 2H). ESI-MS (m/z): Calcd. for C19H16ClN5O: 366.1 (M+1). found: 366.1.

D. To a solution of compound 7b (184 mg, 0.50 mmol) in ethyl acetate (10 mL) and ethanol (5 mL) was added 10% Pd/C (50 mg), under a hydrogen gas atmosphere. After 16 hrs, the suspension was filtered through diatomaceous earth, washed with EA, dried and concentrated to compound 7c (164 mg, 96%). $^1$H NMR (CHLOROFORM-d) δ: 7.38 (dd, J=7.8, 1.8 Hz, 1H), 7.31-7.37 (m, 1H), 7.17-7.23 (m, 2H), 7.05-7.10 (m, 2H), 6.97-7.04 (m, 1H), 6.88 (d, J=8.3 Hz, 1H), 4.23 (quin, J=6.4 Hz, 1H), 3.49 (s, 3H), 3.19 (td, J=15.9, 7.1 Hz, 2H), 2.51-2.67 (m, 2H). ESI-MS (m/z): Calcd. for C19H18ClN3O: 340.1 (M+1). found: 340.1.

E. To a solution of compound 7c (29 mg, 0.084 mmol, 1 eq) in DCM (1 mL) was added triethylamine (0.035 mL, 0.25 mmol, 3 eq) and methanesulfonyl chloride (0.013 mL, 0.17 mmol, 2 eq). After 2 hrs, saturated $NaHCO_3$ was added, the reaction mixture was poured onto a 5 mL extraction tube filled with diatomaceous earth, washed through with DCM, and concentrated. Purification by chromatography (8 g), eluting with 40 to 100% EA/hexanes, gave compound 32 (33 mg, 94%). $^1$H NMR (CHLOROFORM-d) δ: 7.32-7.40 (m, 2H), 7.18-7.24 (m, 2H), 6.98-7.08 (m, 3H), 6.88 (d, J=8.3 Hz, 1H), 5.04 (d, J=9.1 Hz, 1H), 4.59-4.72 (m, 1H), 3.50 (s, 3H), 3.27-3.39 (m, 2H), 3.04 (s, 3H), 2.74-2.87 (m, 2H). ESI-MS (m/z): Calcd. for C20H20C1N3O3S: 418.1 (M+1). found: 418.1.

Following the procedure described above for Example 7 and substituting the appropriate reagents, starting materials and purification methods known to those skilled in the art, the following compounds were prepared:

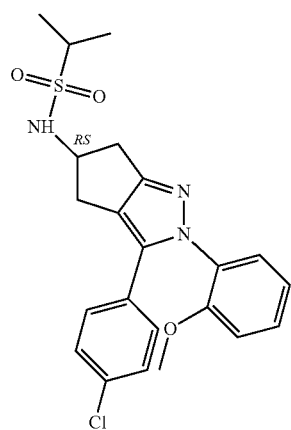

Cpd 33

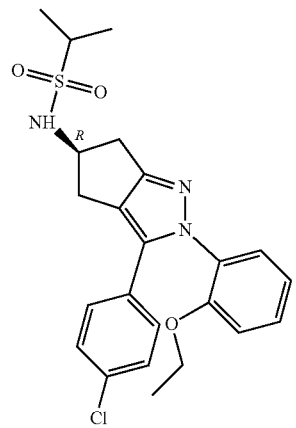

Cpd 44

Cpd 33: ¹H NMR (CHLOROFORM-d) δ: 7.32-7.40 (m, 2H), 7.18-7.24 (m, 2H), 6.99-7.08 (m, 3H), 6.89 (d, J=8.3 Hz, 1H), 4.58-4.70 (m, 1H), 4.52 (d, J=9.9 Hz, 1H), 3.50 (s, 3H), 3.28-3.39 (m, 2H), 3.22 (quin, J=6.9 Hz, 1H), 2.76-2.86 (m, 2H), 1.42 (dd, J=6.8, 1.3 Hz, 6H). ESI-MS (m/z): Calcd. for C22H24ClN3O3S: 446.1 (M+1). found: 446.1.

Cpd 44: ¹H NMR (CHLOROFORM-d) δ: 7.39 (dd, J=7.7, 1.6 Hz, 1H), 7.23-7.29 (m, 1H), 7.11-7.16 (m, 2H), 6.93-7.03 (m, 3H), 6.77 (d, J=7.3 Hz, 1H), 4.50-4.64 (m, 1H), 4.39 (d, J=9.3 Hz, 1H), 3.64 (br. s., 2H), 3.27 (dd, J=15.9, 7.8 Hz, 2H), 3.15 (quin, J=6.8 Hz, 1H), 2.66-2.82 (m, 2H), 1.36 (dd, J=6.8, 1.3 Hz, 6H), 0.92 (t, J=6.9 Hz, 3H). ESI-MS (m/z): Calcd. for C23H26ClN3O3S: 460.1 (M+1). found: 460.1.

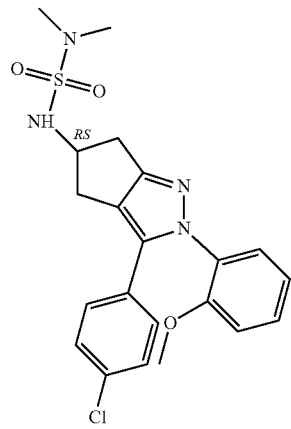

Cpd 34

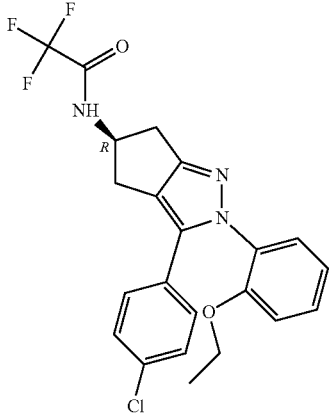

Cpd 45

Cpd 34: ¹H NMR (CHLOROFORM-d) δ: 7.31-7.39 (m, 2H), 7.18-7.24 (m, 2H), 6.99-7.08 (m, 3H), 6.88 (d, J=8.3 Hz, 1H), 4.81 (d, J=9.3 Hz, 1H), 4.48-4.61 (m, 1H), 3.49 (s, 3H), 3.30 (dd, J=15.9, 7.8 Hz, 2H), 2.75-2.87 (m, 8H). ESI-MS (m/z): Calcd. for C21H23ClN4O3S: 447.1 (M+1). found: 447.1.

Cpd 45: ¹H NMR (CHLOROFORM-d) δ: 7.41 (dd, J=7.7, 1.6 Hz, 1H), 7.24-7.31 (m, 1H), 7.12-7.17 (m, 2H), 6.94-7.03 (m, 3H), 6.78 (d, J=7.6 Hz, 1H), 6.61 (br. s., 1H), 5.07 (d, J=7.6 Hz, 1H), 3.66 (br. s., 2H), 3.23-3.43 (m, 2H), 2.65-2.80 (m, 2H), 0.92 (t, J=7.1 Hz, 3H). ESI-MS (m/z): Calcd. for C22H19ClF3N3O2: 450.1 (M+1). found: 450.1.

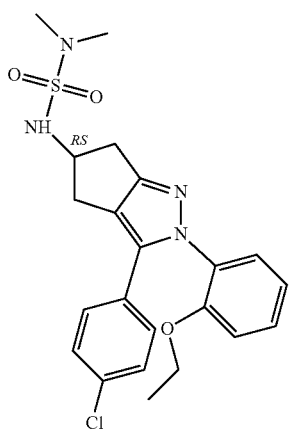

Cpd 47

Cpd 47: ¹H NMR (CHLOROFORM-d) δ: 7.46 (dd, J=7.7, 1.6 Hz, 1H), 7.33 (td, J=7.8, 1.8 Hz, 1H), 7.18-7.23 (m, 2H), 7.00-7.10 (m, 3H), 6.84 (dd, J=8.3, 1.0 Hz, 1H), 4.53 (br. s., 2H), 3.55-3.88 (m, 2H), 3.26-3.38 (m, 2H), 2.76-2.88 (m, 8H), 0.99 (t, J=6.9 Hz, 3H). ESI-MS (m/z): Calcd. for C22H25ClN4O3S: 461.1 (M+1). found: 461.1.

Example 8

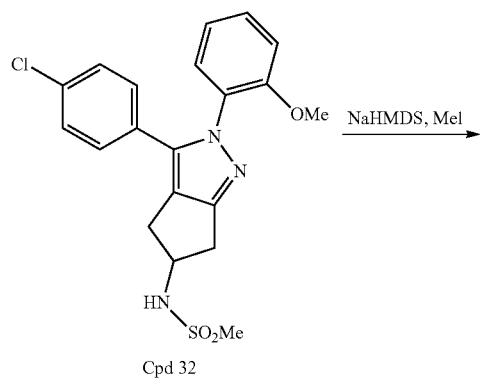

To a solution of compound 32 (21 mg, 0.05 mmol, 1 eq) in THF (2 mL) was added NaHMDS (0.3 mL of a 1 M solution in THF, 0.3 mmol, 6 eq) followed by iodomethane (0.019 mL, 0.3 mmol, 6 eq). After stirring overnight, NH₄Cl was added, the solution was poured onto a 5 mL extraction tube filled with diatomaceous earth, washed through with DCM, and concentrated. Purification by chromatography (8 g), eluting with 35 to 70% EA/hexanes, gave compound 37 (8.2 mg, 38%). ¹H NMR (CHLOROFORM-d) δ: 7.31-7.42 (m, 2H), 7.19-7.24 (m, 2H), 6.99-7.10 (m, 3H), 6.89 (d, J=8.3 Hz, 1H), 5.21-5.31 (m, 1H), 3.50 (s, 3H), 3.15 (dd, J=16.0, 8.7 Hz, 2H), 2.84-3.02 (m, 8H). ESI-MS (m/z): Calcd. for C21H22ClN3O3S: 432.1 (M+1). found: 432.1.

Following the procedure described above for Example 8 and substituting the appropriate reagents, starting materials and purification methods known to those skilled in the art, the following compounds were prepared:

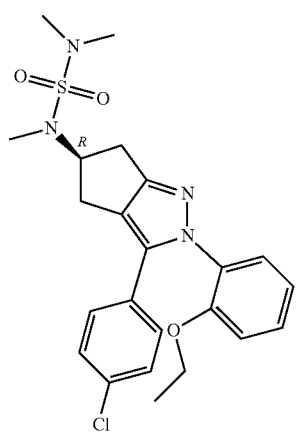

Cpd 46

Cpd 46: ¹H NMR (CHLOROFORM-d) δ: 7.48 (dd, J=7.8, 1.5 Hz, 1H), 7.30-7.37 (m, 1H), 7.17-7.24 (m, 2H), 7.07-7.12 (m, J=8.6 Hz, 2H), 7.04 (td, J=7.6, 1.0 Hz, 1H), 6.84 (d, J=7.6 Hz, 1H), 5.13 (br. s., 1H), 3.71 (br. s., 2H), 3.07-3.22 (m, 2H), 2.90-3.04 (m, 2H), 2.84 (s, 9H), 0.99 (t, J=6.9 Hz, 3H). ESI-MS (m/z): Calcd. for C23H27ClN4O3S: 475.2 (M+1). found: 475.2.

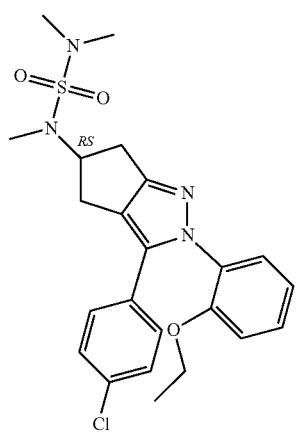

Cpd 48

Cpd 48: ¹H NMR (CHLOROFORM-d) δ: 7.47 (dd, J=7.7, 1.6 Hz, 1H), 7.29-7.36 (m, 1H), 7.18-7.24 (m, 2H), 7.06-7.11 (m, 2H), 7.04 (td, J=7.7, 1.3 Hz, 1H), 6.83 (dd, J=8.3, 1.0 Hz, 1H), 5.06-5.18 (m, 1H), 3.70 (br. s., 2H), 3.08-3.21 (m, 2H), 2.90-3.03 (m, 2H), 2.84 (s, 9H), 0.99 (t, J=6.9 Hz, 3H). ESI-MS (m/z): Calcd. for C23H27ClN4O3S: 475.2 (M+1). found: 475.2.

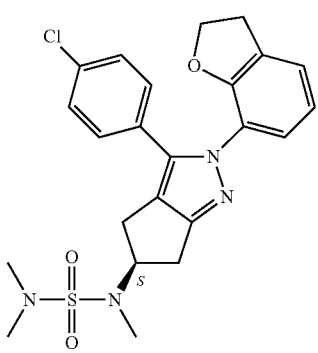

Cpd 50

Cpd 50: ¹H NMR (CHLOROFORM-d) δ: 7.21-7.26 (m, 2H), 7.18 (dd, J=7.3, 1.0 Hz, 1H), 7.09-7.15 (m, 2H), 6.99-7.05 (m, 1H), 6.81-6.87 (m, 1H), 5.05-5.16 (m, 1H), 4.43 (t, J=8.7 Hz, 2H), 3.21 (t, J=8.7 Hz, 2H), 3.13 (ddd, J=15.9, 11.2, 8.5 Hz, 2H), 2.89-3.01 (m, 2H), 2.80-2.85 (m, 9H). ESI-MS (m/z): Calcd. for C23H25ClN4O3S: 473.1 (M+1). found: 473.1.

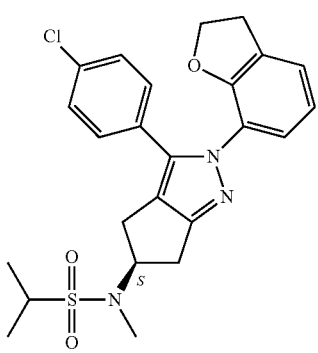

Cpd 51

Cpd 51: ¹H NMR (CHLOROFORM-d) δ: 7.22-7.26 (m, 2H), 7.16-7.21 (m, 1H), 7.09-7.15 (m, 2H), 7.02 (d, J=7.8 Hz, 1H), 6.84 (t, J=7.7 Hz, 1H), 5.11-5.23 (m, 1H), 4.43 (t, J=8.7 Hz, 2H), 3.07-3.28 (m, 5H), 2.90-3.05 (m, 5H), 1.39 (d, J=6.8 Hz, 6H). ESI-MS (m/z): Calcd. for C24H26ClN3O3S: 472.1 (M+1). found: 472.1.

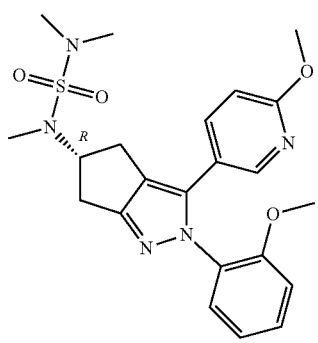

Cpd 57

Cpd 57: ¹H NMR (CHLOROFORM-d) δ: 8.03 (d, J=2.3 Hz, 1H), 7.32-7.41 (m, 2H), 7.24-7.32 (m, 1H), 7.02 (td, J=7.6, 1.1 Hz, 1H), 6.91 (d, J=8.6 Hz, 1H), 6.61 (d, J=8.8 Hz, 1H), 5.13 (t, J=7.7 Hz, 1H), 3.90 (s, 3H), 3.56 (s, 3H), 3.14 (dt, J=16.0, 7.9 Hz, 2H), 2.89-3.04 (m, 2H), 2.85 (s, 3H), 2.83 (s, 6H). ESI-MS (m/z): Calcd. for C22H27N5O4S: 458.2 (M+1). found: 458.2.

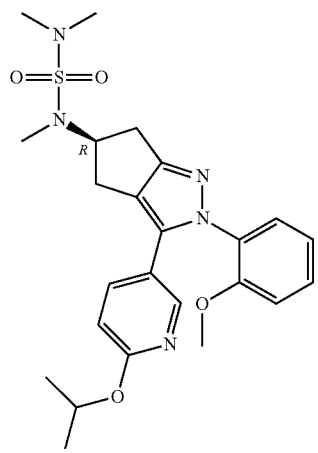

Cpd 58

Cpd 58: ¹H NMR (CHLOROFORM-d) δ: 8.01 (d, J=2.5 Hz, 1H), 7.31-7.39 (m, 2H), 7.22-7.26 (m, 1H), 7.01 (td, J=7.6, 1.1 Hz, 1H), 6.91 (dd, J=8.8, 1.0 Hz, 1H), 6.53 (d, J=8.6 Hz, 1H), 5.24 (quin, J=6.2 Hz, 1H), 5.12 (t, J=7.8 Hz, 1H), 3.56 (s, 3H), 3.07-3.19 (m, 2H), 2.87-3.03 (m, 2H), 2.85 (s, 3H), 2.83 (s, 6H), 1.31 (d, J=6.1 Hz, 6H). ESI-MS (m/z): Calcd. for C24H31N5O4S: 486.2 (M+1). found: 486.2.

Example 9

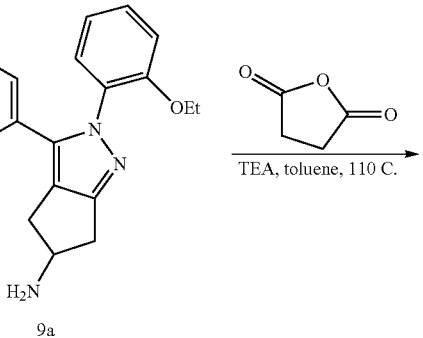

9a

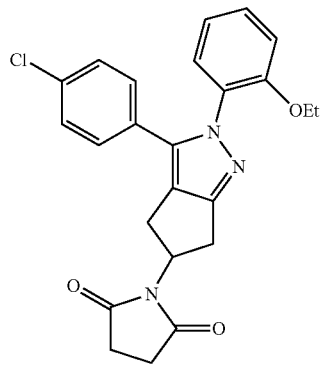

Cpd 38

A. Compound 9a was prepared according to the procedures described in Examples 5 and 7, substituting the appropriate reagents, starting materials and purification methods known to those skilled in the art.

B. To a solution of compound 9a (21 mg, 0.06 mmol, 1 eq) in toluene (1 mL) was added triethylamine (0.05 mL, 0.36 mmol, 6 eq) and succinic anhydride (7 mg, 0.066 mmol, 1.1 eq) and the reaction mixture was stirred for 3 days at 110° C. The solution was concentrated. Purification by chromatography (8 g), eluting with 40 to 100% EA/hexanes, gave compound 38 (19.3 mg, 74%). $^1$H NMR (CHLOROFORM-d) δ: 7.49 (dd, J=7.8, 1.8 Hz, 1H), 7.32 (td, J=8.0, 1.8 Hz, 1H), 7.15-7.23 (m, 2H), 7.07 (d, J=8.6 Hz, 2H), 7.03 (td, J=7.6, 1.3 Hz, 1H), 6.83 (dd, J=8.3, 1.0 Hz, 1H), 5.27-5.44 (m, 1H), 3.71 (br. s., 2H), 3.43 (dd, J=14.8, 9.5 Hz, 2H), 3.06 (dd, J=15.2, 9.1 Hz, 2H), 2.75 (s, 4H), 1.01 (t, J=6.9 Hz, 3H). ESI-MS (m/z): Calcd. for C24H22ClN3O3: 436.1 (M+1). found: 436.1.

Example 10

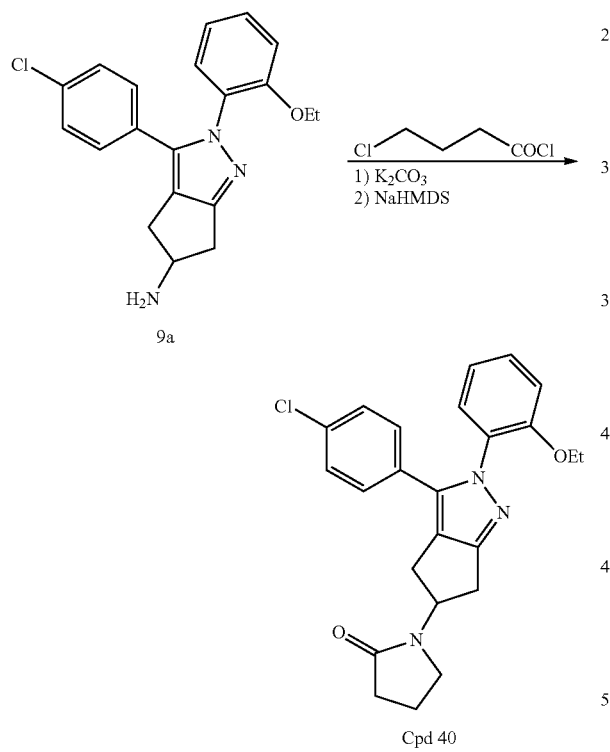

Cpd 40

To a solution of compound 9a (21 mg, 0.06 mmol, 1 eq) in chloroform (1 mL) was added 4-chlorobutyryl chloride (0.014 mL, 0.12 mmol, 2 eq) and 20% aqueous potassium carbonate (1 mL). After 3 hrs, the reaction mixture was poured onto a 5 mL extraction tube filled with diatomaceous earth, washed through with DCM, and concentrated. To a solution of this intermediate in THF (2 mL) in a vial was added NaHMDS (0.3 mL of a 1 M solution in THF, 0.3 mmol, 5 eq), and the solution was warmed to 65° C. After 4 hrs, NH4Cl was added, the solution was poured onto a 5 mL extraction tube filled with diatomaceous earth, washed through with DCM, and concentrated. Purification by chromatography (8 g), eluting with EA gave compound 40 (3.2 mg, 13%). $^1$H NMR (CHLOROFORM-d) δ: 7.49 (dd, J=7.8, 1.8 Hz, 1H), 7.30-7.36 (m, 1H), 7.18-7.23 (m, 2H), 7.06-7.11 (m, 2H), 7.04 (td, J=7.7, 1.3 Hz, 1H), 6.80-6.86 (m, 1H), 5.40-5.52 (m, 1H), 3.71 (br. s., 2H), 3.26-3.47 (m, 2H), 3.05-3.22 (m, 2H), 2.85 (dd, J=16.0, 6.2 Hz, 2H), 2.38-2.47 (m, 2H), 1.98-2.10 (m, 2H), 0.99 (t, J=6.9 Hz, 3H). ESI-MS (m/z): Calcd. for C24H24ClN3O2: 422.2 (M+1). found: 422.2.

Example 11

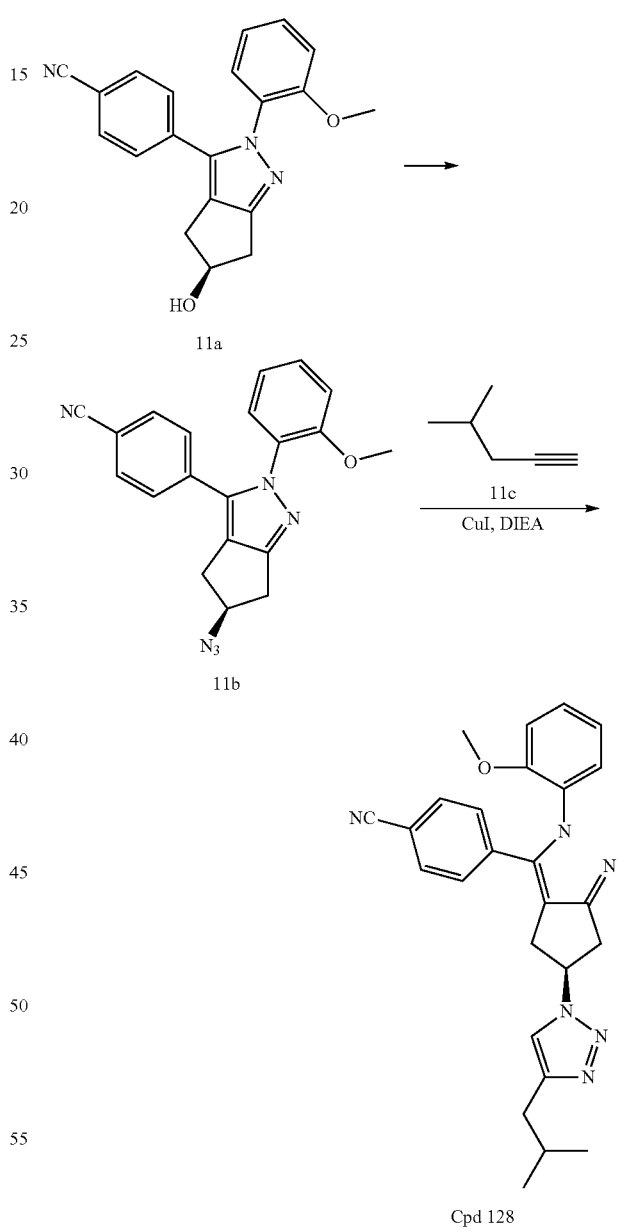

Cpd 128

A. Compound 11a was prepared according to the procedures described in Example 5, substituting (S)-ethyloxiranyl acetate for (R)-ethyloxiranyl acetate (5b) in Step A, and substituting 4-cyanophenylboronic acid for cpd 5k in Step G.

B. Compound 11b was prepared according to the procedures described in Example 7, Steps B and C, substituting compound 11a for Cpd 26.

C. To a solution of compound 11b (25 mg, 0.07 mmol, 1 eq) in THF (1 mL) was added 4-methyl-1-pentyne (11e) (0.011 mL, 0.11 mmol, 1.5 eq), CuI (7 mg, 0.035 mmol, 0.5 eq) and diisopropylethylamine (0.06 mL, 0.35 mmol, 5 eq) and the suspension was stirred overnight at rt. DCM was added, the solution decanted and concentrated. Purification by column chromatography (8 g) in 40 to 80% EA/hexanes gave compound 128. ¹H NMR (CHLOROFORM-d) δ: 7.54 (d, J=8.3 Hz, 2H), 7.45 (dd, J=7.7, 1.6 Hz, 1H), 7.38-7.43 (m, 1H), 7.36 (s, 1H), 7.25 (d, J=8.3 Hz, 2H), 7.08 (t, J=7.7 Hz, 1H), 6.91 (d, J=8.3 Hz, 1H), 5.77-5.88 (m, 1H), 3.59 (dt, J=16.3, 8.3 Hz, 2H), 3.49 (s, 3H), 3.32 (dd, J=16.3, 6.2 Hz, 2H), 2.60 (d, J=7.1 Hz, 2H), 1.91-2.03 (m, 1H), 0.95 (d, J=6.6 Hz, 6H). ESI-MS (m/z): Calcd. for C26H26N6O: 439.2 (M+1). found: 439.2.

Following the procedure described above for Example 11 and substituting the appropriate reagents, starting materials and purification methods known to those skilled in the art, the following compounds were prepared:

Cpd 41

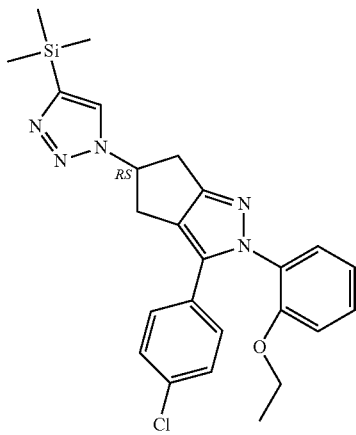

Cpd 41: ¹H NMR (CHLOROFORM-d) δ: 7.60 (s, 1H), 7.51 (dd, J=7.7, 1.6 Hz, 1H), 7.36 (td, J=7.9, 1.6 Hz, 1H), 7.18-7.24 (m, 2H), 7.02-7.12 (m, 3H), 6.86 (d, J=7.6 Hz, 1H), 5.91 (t, J=6.7 Hz, 1H), 3.44-3.90 (m, 4H), 3.30 (dd, J=16.2, 6.1 Hz, 2H), 1.02 (t, J=6.9 Hz, 3H), 0.32 (s, 9H). ESI-MS (m/z): Calcd. for C25H28ClN5OSi: 478.2 (M+1). found: 478.2.

Cpd 42

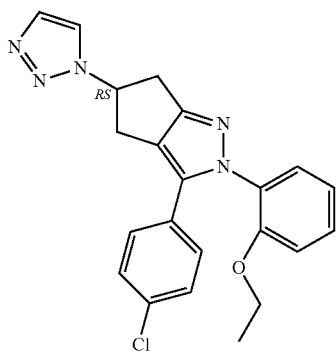

Cpd 42: ¹H NMR (CHLOROFORM-d) δ: 7.73 (s, 1H), 7.64 (s, 1H), 7.51 (dd, J=7.7, 1.6 Hz, 1H), 7.32-7.40 (m, 1H), 7.18-7.25 (m, 2H), 7.02-7.12 (m, 3H), 6.86 (d, J=8.3 Hz, 1H), 5.84-5.98 (m, 1H), 3.43-3.92 (m, 4H), 3.29 (dd, J=16.0, 5.4 Hz, 2H), 1.02 (t, J=6.9 Hz, 3H). ESI-MS (m/z): Calcd. for C22H20ClN5O: 406.1 (M+1). found: 406.1.

Cpd 124

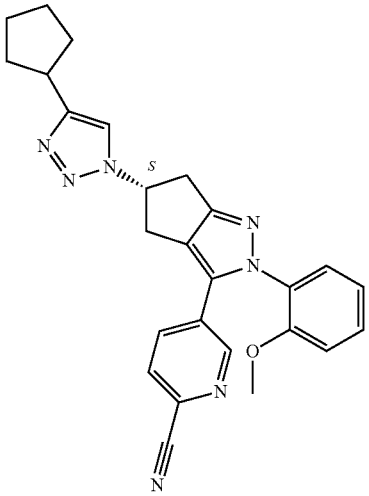

Cpd 124: ¹H NMR (CHLOROFORM-d) δ: 7.54 (d, J=8.3 Hz, 2H), 7.45 (d, J=7.6 Hz, 1H), 7.38-7.44 (m, 1H), 7.35 (s, 1H), 7.25 (d, J=8.3 Hz, 2H), 7.08 (t, J=7.6 Hz, 1H), 6.91 (d, J=8.1 Hz, 1H), 5.82 (quin, J=7.1 Hz, 1H), 3.58 (dt, J=16.2, 8.2 Hz, 2H), 3.49 (s, 3H), 3.32 (dd, J=16.2, 6.3 Hz, 2H), 3.19 (quin, J=8.0 Hz, 1H), 2.05-2.18 (m, 2H), 1.60-1.84 (m, 6H). ESI-MS (m/z): Calcd. for C27H26N6O: 451.2 (M+1). found: 451.2.

Cpd 125

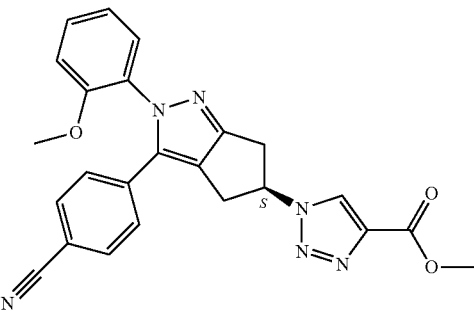

Cpd 125: ¹H NMR (CHLOROFORM-d) δ: 8.18 (s, 1H), 7.55 (d, J=8.3 Hz, 2H), 7.47 (d, J=7.6 Hz, 1H), 7.38-7.45 (m, 1H), 7.24 (d, J=8.3 Hz, 2H), 7.09 (t, J=7.6 Hz, 1H), 6.92 (d, J=8.3 Hz, 1H), 5.86-5.97 (m, 1H), 3.96 (s, 3H), 3.57-3.72 (m, 2H), 3.50 (s, 3H), 3.21-3.37 (m, 2H). ESI-MS (m/z): Calcd. for C24H20N6O3: 441.2 (M+1). found: 441.2.

Cpd 128

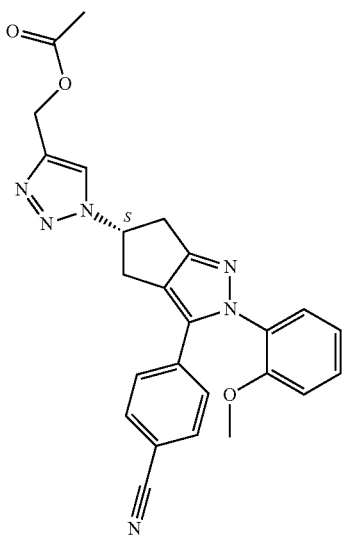

Cpd 136

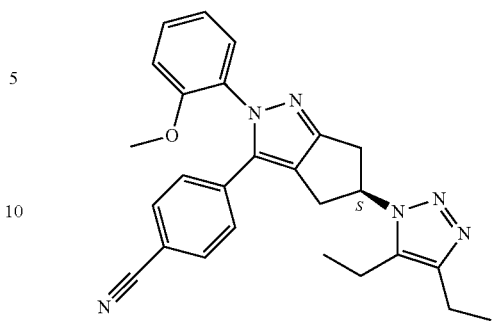

Cpd 136: ¹H NMR (CHLOROFORM-d) δ: 7.53 (d, J=8.6 Hz, 2H), 7.44 (dd, J=7.7, 1.6 Hz, 1H), 7.40 (td, J=7.8, 1.7 Hz, 1H), 7.22-7.26 (m, 2H), 7.07 (td, J=7.6, 1.1 Hz, 1H), 6.90 (d, J=8.3 Hz, 1H), 5.50 (t, J=8.2 Hz, 1H), 3.54-3.72 (m, 2H), 3.50 (s, 3H), 3.34-3.49 (m, 2H), 2.70 (dq, J=10.5, 7.7 Hz, 4H), 1.31 (t, J=7.6 Hz, 3H), 1.23 (t, J=7.7 Hz, 3H). ESI-MS (m/z): Calcd. for C26H26N6O: 439.2 (M+1). found: 439.2.

Example 12

Cpd 128: ¹H NMR (CHLOROFORM-d) δ: 7.71 (s, 1H), 7.51-7.57 (m, 2H), 7.46 (dd, J=7.8, 1.7 Hz, 1H), 7.38-7.44 (m, 1H), 7.22-7.27 (m, 2H), 7.04-7.11 (m, 1H), 6.88-6.94 (m, 1H), 5.77-5.89 (m, 1H), 5.22 (s, 2H), 3.54-3.67 (m, 2H), 3.49 (s, 3H), 3.27-3.39 (m, 2H), 2.08 (s, 3H). ESI-MS (m/z): Calcd. for C25H22N6O3: 455.2 (M+1). found: 455.2.

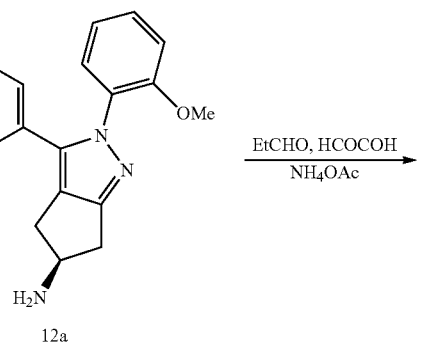

12a

Cpd 130

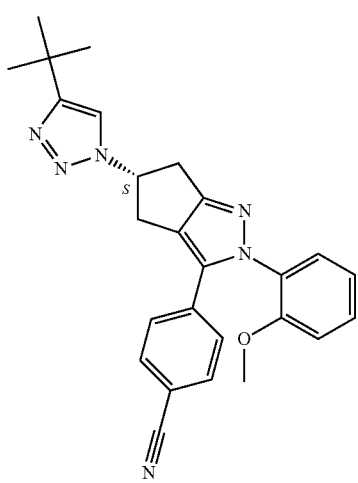

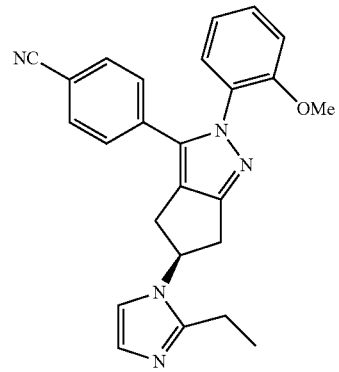

Cpd 134

Cpd 130: ¹H NMR (CHLOROFORM-d) δ: 7.51-7.56 (m, 2H), 7.45 (dd, J=7.7, 1.6 Hz, 1H), 7.41 (td, J=7.9, 1.7 Hz, 1H), 7.35 (s, 1H), 7.25 (d, J=8.6 Hz, 2H), 7.08 (td, J=7.6, 1.1 Hz, 1H), 6.89-6.94 (m, 1H), 5.76-5.87 (m, 1H), 3.58 (dt, J=16.5, 8.4 Hz, 2H), 3.49 (s, 3H), 3.28-3.39 (m, 2H), 1.36 (s, 9H). ESI-MS (m/z): Calcd. for C26H26N6O: 439.2 (M+1). found: 439.2.

A. Compound 12a was prepared according to Example 7, Step D, substituting compound 11b for compound 7b.

B. A solution of compound 12a (25 mg, 0.07 mmol, 1 eq), ammonium acetate (22 mg, 0.29 mmol, 4 eq), propionaldehyde (0.021 mL, 0.29 mmol, 1 eq) and glyoxal (0.033 mL of a 40% solution in water, 0.29 mL, 1 eq) in methanol (1 mL) were heated to 80° C. overnight in a vial. The solution was concentrated. Purification by HPLC eluting with 5 to 60% ACN/H₂O gave compound 134 (16.3 mg, 51%). ¹H NMR (CHLOROFORM-d) δ: 7.54 (d, J=8.3 Hz, 2H), 7.45 (dd, J=7.8, 1.7 Hz, 1H), 7.41 (td, J=7.9, 1.6 Hz, 1H), 7.24 (d, J=8.3 Hz, 2H), 7.08 (t, J=7.6 Hz, 1H), 7.01 (s, 1H), 6.98 (s, 1H), 6.91 (d, J=8.1 Hz, 1H), 5.32-5.43 (m, 1H), 3.38-3.52 (m, 5H), 3.01-3.18 (m, 2H), 2.83 (q, J=7.6 Hz, 2H), 1.93-2.39 (m, 2H), 1.39 (t, J=7.6 Hz, 2H). ESI-MS (m/z): Calcd. for C25H23N5O: 410.2 (M+1). found: 410.2.

Following the procedure described above for Example 12 and substituting the appropriate reagents, starting materials and purification methods known to those skilled in the art, the following compounds were prepared:

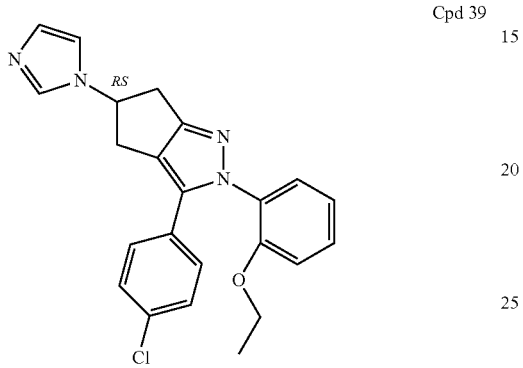

Cpd 39

Cpd 39: ¹H NMR (CHLOROFORM-d) δ: 7.63 (s, 1H), 7.50 (dd, J=7.7, 1.6 Hz, 1H), 7.32-7.39 (m, 1H), 7.18-7.25 (m, 2H), 7.00-7.12 (m, 5H), 6.82-6.88 (m, 1H), 5.35 (quin, J=6.6 Hz, 1H), 3.76 (br. s., 2H), 3.50 (dd, J=16.2, 8.1 Hz, 2H), 3.15 (dd, J=15.9, 5.8 Hz, 2H), 1.02 (t, J=7.1 Hz, 3H). ESI-MS (m/z): Calcd. for C23H21ClN4O: 405.1 (M+1). found: 405.1.

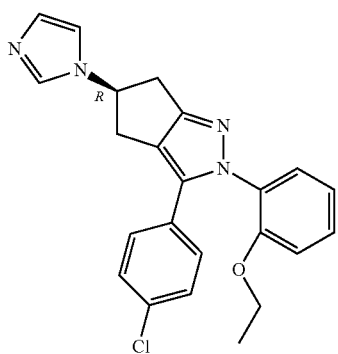

Cpd 43

Cpd 43: ¹H NMR (CHLOROFORM-d) δ: 7.66 (s, 1H), 7.50 (dd, J=7.8, 1.5 Hz, 1H), 7.31-7.40 (m, 1H), 7.18-7.25 (m, 2H), 7.00-7.14 (m, 5H), 6.86 (d, J=8.3 Hz, 1H), 5.28-5.43 (m, 1H), 3.74 (br. s., 2H), 3.37-3.57 (m, 2H), 3.00-3.23 (m, 2H), 1.03 (t, J=6.9 Hz, 3H). ESI-MS (m/z): Calcd. for C23H21ClN4O: 405.1 (M+1). found: 405.1.

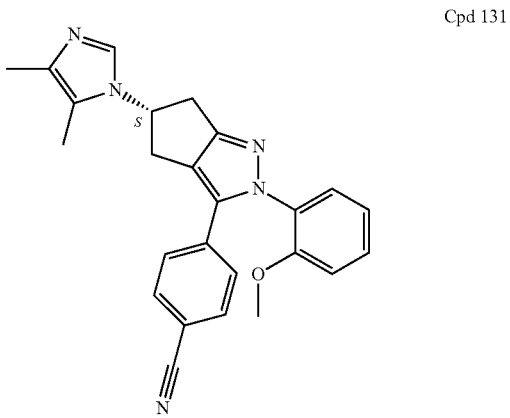

Cpd 131

Cpd 131: ¹H NMR (CHLOROFORM-d) δ: 7.53 (d, J=8.3 Hz, 3H), 7.45 (d, J=7.6 Hz, 1H), 7.40 (t, J=8.0 Hz, 1H), 7.23 (d, J=8.3 Hz, 2H), 7.07 (t, J=7.6 Hz, 1H), 6.90 (d, J=8.3 Hz, 1H), 5.20 (quin, J=6.8 Hz, 1H), 3.36-3.54 (m, 5H), 3.01-3.22 (m, 2H), 2.21 (s, 3H), 2.17 (s, 3H). ESI-MS (m/z): Calcd. for C25H23N5O: 410.2 (M+1). found: 410.2.

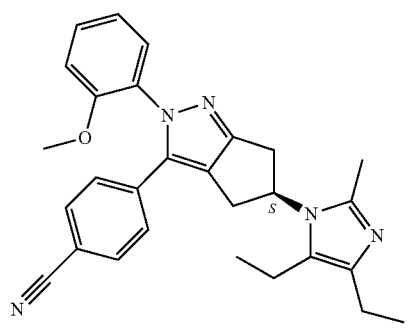

Cpd 138

Cpd 138: ¹H NMR (CHLOROFORM-d) δ: 7.54 (d, J=8.1 Hz, 2H), 7.46 (d, J=7.8 Hz, 1H), 7.41 (t, J=8.0 Hz, 1H), 7.20-7.26 (m, 2H), 7.08 (t, J=7.6 Hz, 1H), 6.92 (d, J=8.3 Hz, 1H), 5.39 (m, J=8.3 Hz, 1H), 3.34-3.52 (m, 5H), 3.15-3.32 (m, 2H), 2.60 (q, J=7.4 Hz, 2H), 2.51 (q, J=7.4 Hz, 2H), 2.45 (s, 3H), 1.22 (t, J=7.6 Hz, 3H), 1.16 (t, J=7.5 Hz, 3H). ESI-MS (m/z): Calcd. for C28H29N5O: 452.2 (M+1). found: 452.2.

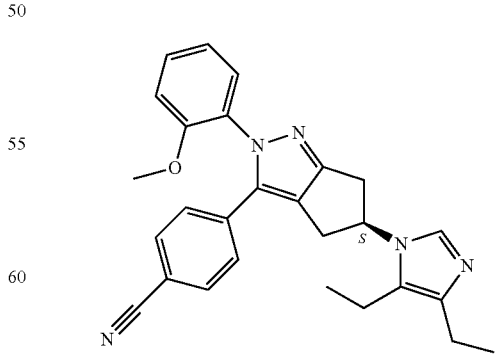

Cpd 139

Cpd 139: ¹H NMR (CHLOROFORM-d) δ: 7.58 (s, 1H), 7.50-7.56 (m, J=8.3 Hz, 2H), 7.45 (dd, J=7.7, 1.6 Hz, 1H), 7.37-7.43 (m, 1H), 7.20-7.26 (m, J=8.3 Hz, 2H), 7.08 (td,

J=7.6, 1.1 Hz, 1H), 6.91 (d, J=7.6 Hz, 1H), 5.16-5.27 (m, 1H), 3.40-3.55 (m, 5H), 3.03-3.22 (m, 2H), 2.64 (q, J=7.5 Hz, 2H), 2.55 (q, J=7.6 Hz, 2H), 1.24 (t, J=7.6 Hz, 3H), 1.19 (t, J=7.6 Hz, 3H). ESI-MS (m/z): Calcd. for C27H27N5O: 438.2 (M+1). found: 438.2.

Example 13

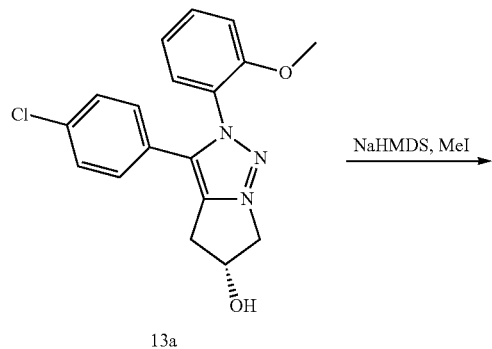

13a

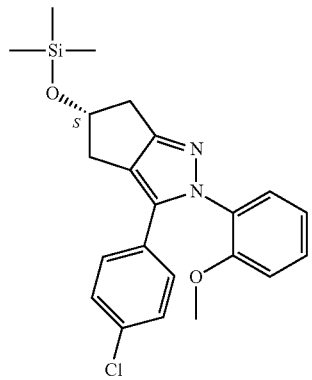

Cpd 69

Cpd 69: ¹H NMR (CHLOROFORM-d) δ: 7.30-7.42 (m, 2H), 7.18-7.24 (m, 2H), 7.05-7.11 (m, 2H), 6.98-7.04 (m, 1H), 6.88 (d, J=8.3 Hz, 1H), 4.98 (t, J=6.4 Hz, 1H), 3.49 (s, 3H), 3.14 (td, J=15.1, 6.9 Hz, 2H), 2.72-2.87 (m, 2H), 0.19 (s, 9H). ESI-MS (m/z): Calcd. for C22H25ClN2O2Si: 413.1 (M+1). found: 413.1.

Example 14

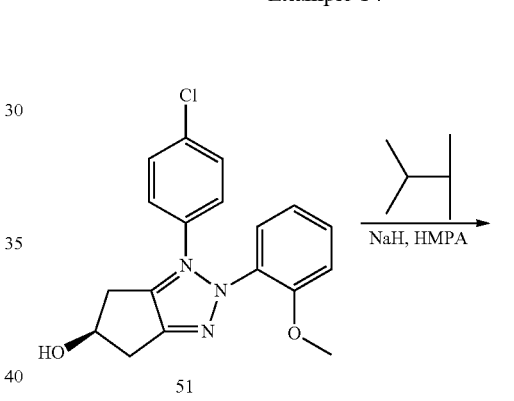

A. Compound 13a was prepared according to the procedures described in Example 5, substituting (S)-ethyloxiranyl acetate for (R)-ethyloxiranyl acetate (5b) in Step A.

B. To a solution of compound 13a (10 mg, 0.026 mmol, 1 eq) in THF (1 mL) and DMF (0.5 mL) at rt was added NaHMDS (0.13 mL of a 1 M solution in THF, 0.13 mmol, 5 eq) followed by iodomethane (0.016 mL, 0.26 mmol, 10 eq). After 1 hr, water was added, the solution was poured onto a 5 mL extraction tube filled with diatomaceous earth, then DCM was added, and the organic phases concentrated. Purification by column chromatography (8 g), eluting with 25 to 50% EA/hexanes, gave compound 49 (7.2 mg, 73%). ¹H NMR (CHLOROFORM-d) δ: 7.30-7.41 (m, 2H), 7.18-7.23 (m, 2H), 7.04-7.10 (m, 2H), 7.01 (td, J=7.6, 1.0 Hz, 1H), 6.87 (d, J=8.3 Hz, 1H), 4.54-4.64 (m, 1H), 3.48 (s, 3H), 3.43 (s, 3H), 3.11-3.23 (m, 2H), 2.78-2.94 (m, 2H). ESI-MS (m/z): Calcd. for C20H19ClN2O2: 355.1 (M+1). found: 355.1.

Following the procedure described above for Example 13 and substituting the appropriate reagents, starting materials and purification methods known to those skilled in the art, the following compound was prepared:

To a solution of compound 51 (50 mg, 0.15 mmol, 1 eq) in HMPA (2 mL) was added sodium hydride (18 mg of a 60% dispersion in oil, 0.44 mmol, 3 eq). The solution bubbled and turned purplish and after 30 min, 2-iodopropane (0.029 mL, 0.29 mmol, 2 eq) was added and the solution stirred overnight at rt. Additional sodium hydride (20 mg) and 2-iodopropane (0.029 mL) were added, and the reaction was heated again to 50° C. overnight. 15-crown-5 (10 mg) was added, and the reaction was heated to 50° C. for 2 days. A solution of NH₄Cl was added, the reaction mixture was extracted with DCM, the organic phases combined, dried over MgSO₄, filtered, and concentrated. Purification by column chromatography (8 g), eluting with 25 to 50% EA/hexanes, gave compound 67 (3.4 mg, 6%). ¹H NMR (CHLOROFORM-d) δ: 7.38 (dd, J=7.7, 1.6 Hz, 1H), 7.30-7.36 (m, 1H), 7.16-7.23 (m, 2H), 7.04-7.10 (m, 2H), 6.97-7.04 (m, 1H), 6.84-6.90 (m, 1H), 4.72-4.82 (m, 1H), 3.77 (dt, J=12.3, 6.1 Hz, 1H), 3.49 (s, 3H), 3.10-3.23 (m, 2H), 2.74-2.90 (m, 2H), 1.22 (dd, J=6.1, 1.3 Hz, 6H). ESI-MS (m/z): Calcd. for C22H23ClN2O2: 383.2 (M+1). found: 383.2.

Example 15

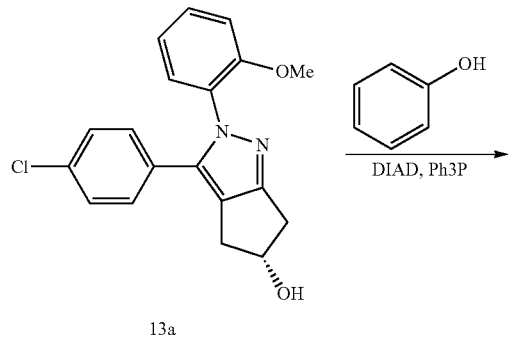

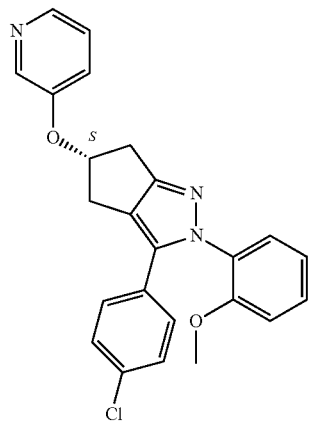

Cpd 59: ¹H NMR (CHLOROFORM-d) δ: 8.36 (t, J=1.8 Hz, 1H), 8.25 (t, J=3.0 Hz, 1H), 7.41 (dd, J=7.7, 1.6 Hz, 1H), 7.32-7.38 (m, 1H), 7.23-7.26 (m, 2H), 7.17-7.23 (m, 2H), 7.05-7.11 (m, 2H), 7.03 (td, J=7.6, 1.3 Hz, 1H), 6.89 (dd, J=8.3, 1.0 Hz, 1H), 5.54 (tt, J=6.9, 3.5 Hz, 1H), 3.51 (s, 3H), 3.34-3.46 (m, 2H), 2.99-3.16 (m, 2H). ESI-MS (m/z): Calcd. for C24H20ClN3O2: 418.1 (M+1). found: 418.1.

Example 16

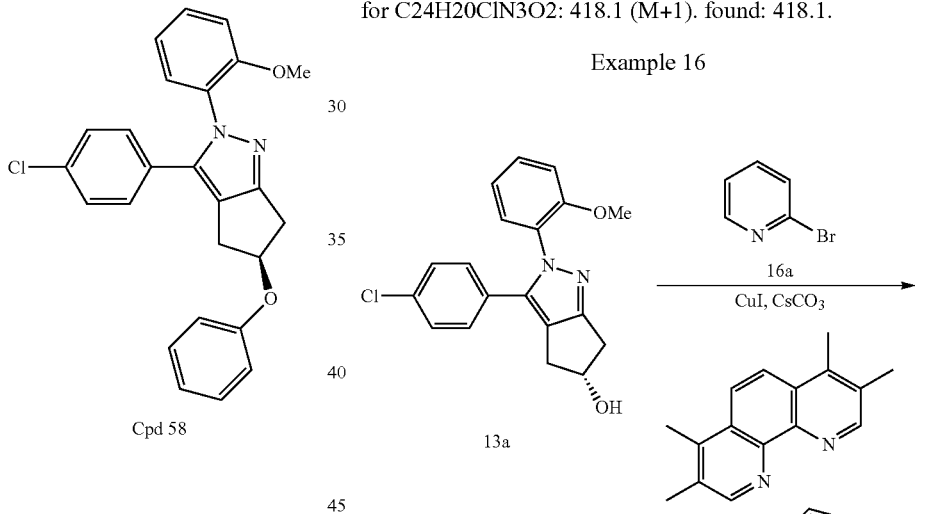

To a solution of compound 13a (25 mg, 0.07 mmol, 1 eq) in THF (2 mL) was added phenol (9 mg, 0.09 mmol, 1.25 eq), DIAD (0.018 mL, 0.09 mmol, 1.25 eq) and triphenylphosphine (24 mg, 0.09 mmol, 1.25 eq) and the solution was heated to 50° C. overnight. The solution was concentrated. Purification by column chromatography (8 g), eluting with 20 to 40% EA/hexanes, gave Cpd 58. Further purification by HPLC eluting with 10 to 100% ACN/H₂O gave Cpd 58 (12.8 mg, 41%). ¹H NMR (CHLOROFORM-d) δ: 7.40 (dd, J=7.8, 1.8 Hz, 1H), 7.28-7.38 (m, 3H), 7.17-7.23 (m, 2H), 7.05-7.11 (m, 2H), 7.00-7.05 (m, 1H), 6.92-7.00 (m, 3H), 6.89 (d, J=7.3 Hz, 1H), 5.51 (tt, J=6.9, 3.6 Hz, 1H), 3.50 (s, 3H), 3.31-3.44 (m, 2H), 2.98-3.14 (m, 2H). ESI-MS (m/z): Calcd. for C25H21ClN2O2: 417.1 (M+1). found: 417.1.

Following the procedure described above for Example 15 and substituting the appropriate reagents, starting materials and purification methods known to those skilled in the art, the following compound was prepared:

To a solution of compound 13a (15 mg, 0.044 mmol, 1 eq) in toluene (2 mL) was added 2-bromopyridine (16a) (14 mg, 0.09 mmol, 2 eq), 3,4,7,8-tetramethyl-1,10-phenanthroline (1 mg, 0.004 mmol, 0.1 eq) cesium carbonate (22 mg, 0.066 mmol, 1.5 eq) and CuI (1 mg, 0.004 mmol, 0.1 eq) and the suspension heated to 110° C. for 3 hrs, then to 140° C. overnight. The reaction was filtered through a short silica column with EA and concentrated. Purification by column chromatography (12 g), eluting with 30 to 100% EA/hexanes, gave compound 61 (3 mg, 15%). ¹H NMR (CHLOROFORM-d) δ: 8.19 (dd, J=5.1, 1.3 Hz, 1H), 7.58 (ddd, J=8.5, 6.9, 2.0 Hz, 1H), 7.41 (dd, J=7.7, 1.6 Hz, 1H), 7.31-7.38 (m, 1H), 7.16-7.23 (m, 2H), 7.06-7.12 (m, 2H), 6.98-7.06 (m, 1H), 6.84-6.93 (m, 2H), 6.75 (d, J=8.3 Hz, 1H), 6.13 (dt, J=6.9, 3.3 Hz, 1H), 3.50 (s, 3H), 3.37-3.48 (m, 2H), 2.91-3.11 (m, 2H). ESI-MS (m/z): Calcd. for C24H20ClN3O2: 418.1 (M+1). found: 418.1.

Example 17

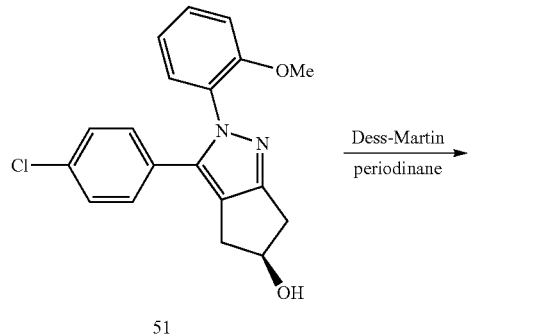

51

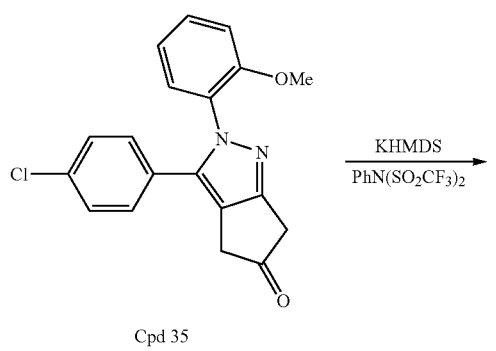

Cpd 35

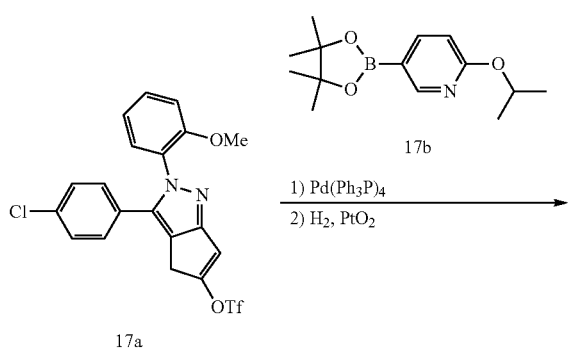

17a

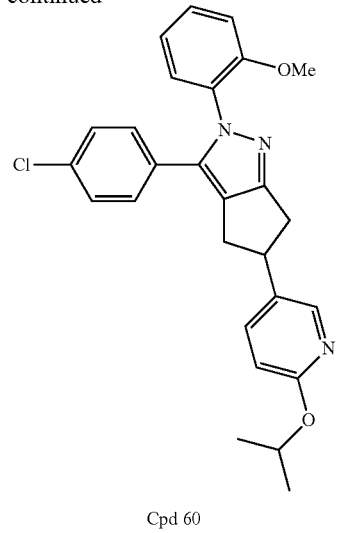

Cpd 60

A. To a solution of compound 51 (670 mg, 1.97 mmol, 1 eq) in DCM (60 mL) at 0° C. was added Dess-Martin periodinane (917 mg, 2.16 mmol, 1.1 eq) and the reaction was stirred for 1.5 hrs. Saturated NaHCO₃ and sodium thiosulfate were added and the reaction mixture was stirred 30 min. At that time, the aqueous phase was extracted with DCM, the organic phases combined, dried over MgSO₄, filtered, and concentrated. Purification by column chromatography (40 g), eluting with 25 to 50% EA/hexanes, gave compound 35 (579 mg, 87%). ¹H NMR (CHLOROFORM-d) δ: 7.35-7.44 (m, 2H), 7.21-7.26 (m, 3H), 7.07-7.12 (m, 2H), 7.05 (td, J=7.6, 1.1 Hz, 1H), 6.88-6.94 (m, 1H), 3.47-3.58 (m, 7H). ESI-MS (m/z): Calcd. for C19H15ClN2O2: 339.1 (M+1). found: 339.0.

B. To a solution of compound 35 (271 mg, 0.8 mmol, 1 eq) in THF (17 mL) at −78° C. under Ar$_{(g)}$ was added KHMDS (1.92 mL of a 0.5 M solution in toluene, 0.96 mmol, 1.2 eq). After 30 min, N-phenyl-bis(trifluoromethanesulfonimide) (343 mg, 0.96 mmol, 1.2 eq) was added in THF (3 mL), and the reaction mixture was warmed to rt over 2 hrs. Methanol was added and the solution concentrated. Purification by column chromatography (24 g), eluting with 15 to 30% EA/hexanes, gave compound 17a (131 mg, 35%, 60:40 mix of isomers). ESI-MS (m/z): Calcd. for C20H14ClF3N2O4S: 471.1 (M+1). found: 471.1.

C. To a solution of compound 17a (15 mg, 0.032 mmol, 1 eq) in DME (1.6 mL) was added Pd(Ph₃P)₄ (4 mg, 0.0032 mmol, 0.1 eq), 2 M sodium carbonate (0.25 mL) and 2-isopropoxy-5-(4,4,5,5-tetramethyl-1,3,2-dioxaborolan-2-yl)pyridine (17b) (17 mL, 0.064 mmol, 2 eq). The solution was degassed by bubbling Ar$_{(g)}$, then heated to 80° C. for 30 min. The solution was poured onto a 5 mL extraction tube filled with diatomaceous earth, DCM was added and the organic phase concentrated. The residue was dissolved in ethyl acetate (5 mL) and methanol (3 mL), PtO₂ (5 mg) was added, and the reaction mixture was placed under a hydrogen gas atmosphere overnight. The catalyst was filtered through diatomaceous earth, and the filtrate concentrated. Purification by column chromatography (8 g), eluting with 20 to 40% EA/hexanes, gave impure compound 60 (—Cl present). Further purification by HPLC, eluting with 10 to 70% ACN/H₂O gave compound 60 (2.6 mg, 17%) in the desired purity. ¹H NMR (CHLOROFORM-d) δ: 8.11 (d, J=2.5 Hz, 1H), 7.57 (dd, J=8.5, 2.7 Hz, 1H), 7.42 (dd, J=7.7, 1.6 Hz, 1H), 7.32-7.39 (m, 1H), 7.17-7.23 (m, 2H), 7.06-7.12 (m, 2H), 7.00-

7.06 (m, 1H), 6.86-6.93 (m, 1H), 6.67 (d, J=8.6 Hz, 1H), 5.28 (quin, J=6.2 Hz, 1H), 3.99-4.12 (m, 1H), 3.51 (s, 3H), 3.26 (td, J=16.2, 8.5 Hz, 2H), 2.83-3.01 (m, 2H), 1.35 (d, J=6.3 Hz, 6H). ESI-MS (m/z): Calcd. for C27H26ClN3O2: 460.2 (M+1). found: 460.2.

Following the procedure described above for Example 17 and substituting the appropriate reagents, starting materials and purification methods known to those skilled in the art, the following compounds were prepared:

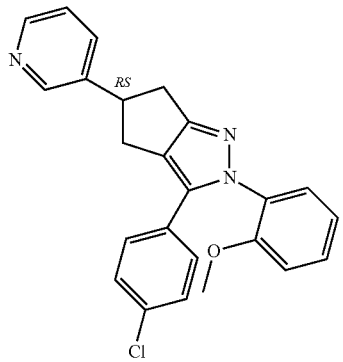

Cpd 63

Cpd 63: ¹H NMR (CHLOROFORM-d) δ: 8.63 (d, J=2.0 Hz, 1H), 8.51 (dd, J=4.8, 1.5 Hz, 1H), 7.69 (d, J=8.1 Hz, 1H), 7.42 (dd, J=7.7, 1.6 Hz, 1H), 7.32-7.40 (m, 1H), 7.27-7.31 (m, 1H), 7.17-7.24 (m, J=8.6 Hz, 2H), 7.07-7.12 (m, J=8.6 Hz, 2H), 7.00-7.07 (m, 1H), 6.90 (d, J=8.3 Hz, 1H), 4.06-4.19 (m, 1H), 3.52 (s, 3H), 3.33 (td, J=15.3, 8.5 Hz, 2H), 2.89-3.08 (m, 2H). ESI-MS (m/z): Calcd. for C24H20ClN3O: 402.1 (M+1). found: 402.1.

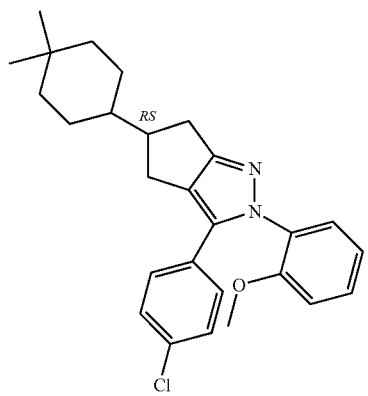

Cpd 64

Cpd 64: ¹H NMR (CHLOROFORM-d) δ: 7.38 (dd, J=7.8, 1.8 Hz, 1H), 7.30-7.36 (m, 1H), 7.17-7.22 (m, 2H), 7.05-7.11 (m, 2H), 7.01 (td, J=7.6, 1.3 Hz, 1H), 6.88 (d, J=8.3 Hz, 1H), 3.49 (s, 3H), 2.84-2.98 (m, 2H), 2.63-2.75 (m, 2H), 2.49-2.62 (m, 2H), 1.62-1.73 (m, 2H), 1.42 (d, J=6.6 Hz, 2H), 1.17-1.30 (m, 5H), 0.91 (d, J=4.8 Hz, 6H). ESI-MS (m/z): Calcd. for C27H31ClN2O: 435.2 (M+1). found: 435.2.

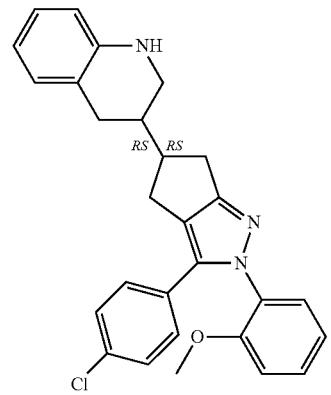

Cpd 65

Cpd 65: ¹H NMR (CHLOROFORM-d) δ: 7.30-7.41 (m, 2H), 7.18-7.23 (m, 2H), 7.06-7.11 (m, 2H), 6.94-7.04 (m, 3H), 6.88 (dd, J=8.3, 1.0 Hz, 1H), 6.64 (td, J=7.4, 1.1 Hz, 1H), 6.50 (d, J=8.1 Hz, 1H), 3.40-3.51 (m, 4H), 2.61-3.10 (m, 8H), 2.17 (s, 1H). ESI-MS (m/z): Calcd. for C28H26ClN3O: 456.2 (M+1). found: 456.2.

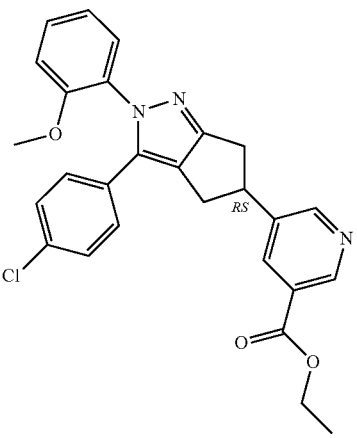

Cpd 66

Cpd 66: ¹H NMR (CHLOROFORM-d) δ: 9.12 (d, J=2.0 Hz, 1H), 8.78 (d, J=2.3 Hz, 1H), 8.30 (t, J=2.0 Hz, 1H), 7.43 (dd, J=7.7, 1.6 Hz, 1H), 7.32-7.40 (m, 1H), 7.17-7.24 (m, 2H), 7.07-7.14 (m, 2H), 7.04 (td, J=7.6, 1.3 Hz, 1H), 6.90 (dd, J=8.3, 1.0 Hz, 1H), 4.43 (q, J=7.2 Hz, 2H), 4.20 (t, J=8.3 Hz, 1H), 3.53 (s, 3H), 3.28-3.43 (m, 2H), 3.04 (dd, J=15.5, 8.5 Hz, 2H), 1.37-1.47 (m, 3H). ESI-MS (m/z): Calcd. for C27H24ClN3O3: 474.2 (M+1). found: 474.2.

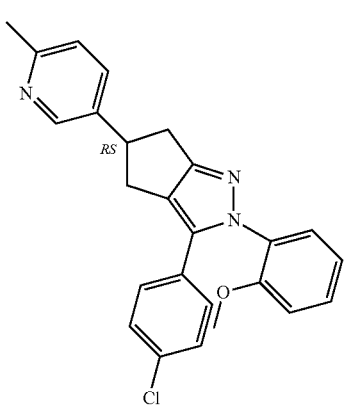

Cpd 73

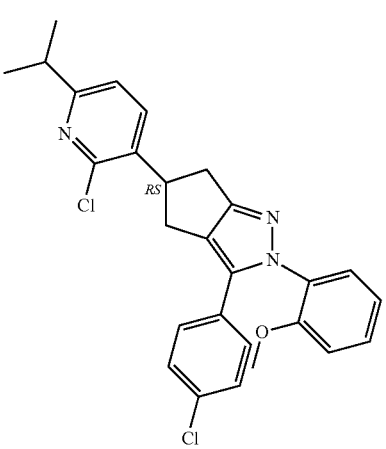

Cpd 75

Cpd 73: ¹H NMR (CHLOROFORM-d) δ: 8.46-8.55 (m, 1H), 7.58 (dd, J=8.0, 2.1 Hz, 1H), 7.42 (dd, J=7.7, 1.6 Hz, 1H), 7.32-7.40 (m, 1H), 7.18-7.25 (m, 2H), 7.06-7.17 (m, 3H), 6.99-7.06 (m, 1H), 6.90 (d, J=8.1 Hz, 1H), 4.10 (quin, J=8.3 Hz, 1H), 3.52 (s, 3H), 3.30 (td, J=15.5, 8.5 Hz, 2H), 2.85-3.05 (m, 2H), 2.55 (s, 3H). ESI-MS (m/z): Calcd. for C25H22ClN3O: 416.2 (M+1). found: 416.2.

Cpd 75: ¹H NMR (CHLOROFORM-d) δ: 7.67 (d, J=7.8 Hz, 1H), 7.42 (dd, J=7.8, 1.5 Hz, 1H), 7.33-7.39 (m, 1H), 7.20 (d, J=8.6 Hz, 2H), 7.06-7.13 (m, 3H), 7.00-7.06 (m, 1H), 6.90 (d, J=8.1 Hz, 1H), 4.50 (quin, J=7.8 Hz, 1H), 3.52 (s, 3H), 3.34 (dd, J=15.9, 8.6 Hz, 2H), 2.80-3.12 (m, 3H), 1.29 (d, J=7.1 Hz, 6H). ESI-MS (m/z): Calcd. for C27H25Cl2N3O: 478.1 (M+1). found: 478.1.

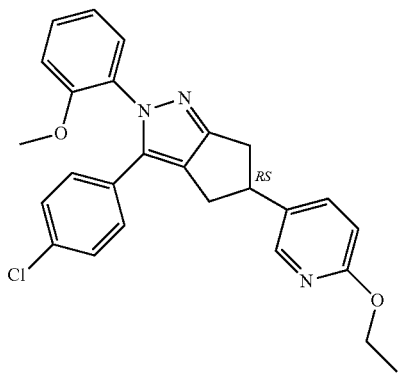

Cpd 74

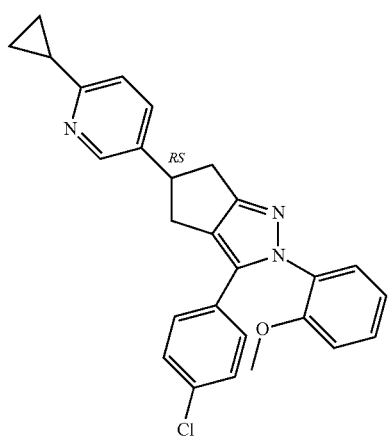

Cpd 77

Cpd 74: ¹H NMR (CHLOROFORM-d) δ: 8.12 (d, J=2.5 Hz, 1H), 7.59 (dd, J=8.6, 2.5 Hz, 1H), 7.42 (dd, J=7.7, 1.6 Hz, 1H), 7.36 (td, J=8.0, 1.8 Hz, 1H), 7.17-7.24 (m, 2H), 7.06-7.12 (m, 2H), 7.03 (td, J=7.6, 1.1 Hz, 1H), 6.85-6.93 (m, 1H), 6.72 (d, J=8.6 Hz, 1H), 4.35 (q, J=7.1 Hz, 2H), 4.06 (quin, J=8.3 Hz, 1H), 3.51 (s, 3H), 3.27 (td, J=16.3, 8.3 Hz, 2H), 2.83-3.01 (m, 2H), 1.40 (t, J=7.1 Hz, 3H). ESI-MS (m/z): Calcd. for C26H24ClN3O2: 446.2 (M+1). found: 446.2.

Cpd 77: ¹H NMR (CHLOROFORM-d) δ: 8.44 (d, J=2.0 Hz, 1H), 7.54 (dd, J=8.0, 2.1 Hz, 1H), 7.41 (dd, J=7.7, 1.6 Hz, 1H), 7.35 (td, J=8.0, 1.8 Hz, 1H), 7.17-7.23 (m, 2H), 7.06-7.13 (m, 3H), 7.03 (td, J=7.6, 1.1 Hz, 1H), 6.86-6.92 (m, 1H), 4.07 (quin, J=8.3 Hz, 1H), 3.51 (s, 3H), 3.19-3.35 (m, 2H), 2.82-3.03 (m, 2H), 1.98-2.08 (m, 1H), 0.94-1.04 (m, 4H). ESI-MS (m/z): Calcd. for C27H24ClN3O: 442.2 (M+1). found: 442.2.

Example 18

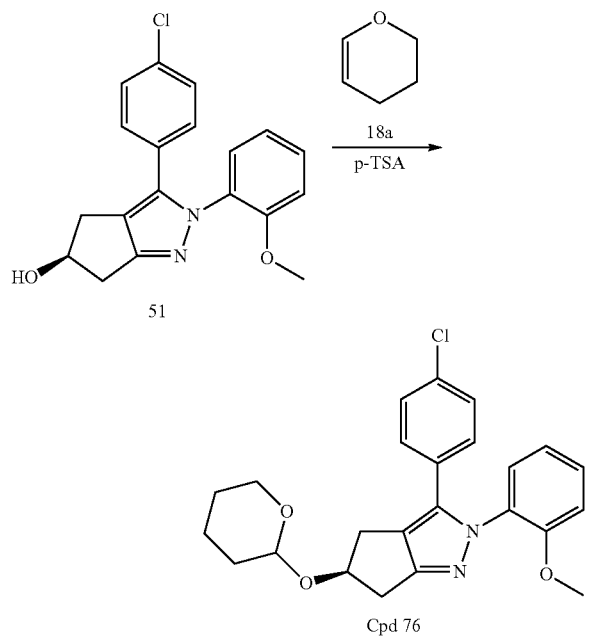

To a suspension of compound 5l (25 mg, 0.07 mmol, 1 eq) in dichloroethane (2 mL) was added 3,4-dihydro-2H-pyran (18a) (33 mg, 0.37 mmol, 5 eq) and p-toluenesulfonic acid (13 mg, 0.07 mmol, 1 eq) and the reaction mixture stirred at rt for 2 hrs. MP-carbonate was added, stirred 20 min, filtered and concentrated. Purification by column chromatography (8 g), eluting with 20 to 40% EA/hexanes, gave compound 76 (16.4 mg, 50%). $^1$H NMR (CHLOROFORM-d) δ: 7.30-7.42 (m, 2H), 7.16-7.23 (m, 2H), 7.04-7.11 (m, 2H), 7.01 (t, J=7.7 Hz, 1H), 6.84-6.91 (m, 1H), 4.96-5.07 (m, 1H), 4.74-4.82 (m, 1H), 3.94 (ddd, J=11.1, 7.6, 3.3 Hz, 1H), 3.52-3.61 (m, 1H), 3.49 (d, J=2.8 Hz, 3H), 3.11-3.31 (m, 2H), 2.74-3.04 (m, 2H), 1.69-1.95 (m, 2H), 1.46-1.65 (m, 4H). ESI-MS (m/z): Calcd. for C24H25ClN2O3: 425.2 (M+1). found: 425.2.

Example 19

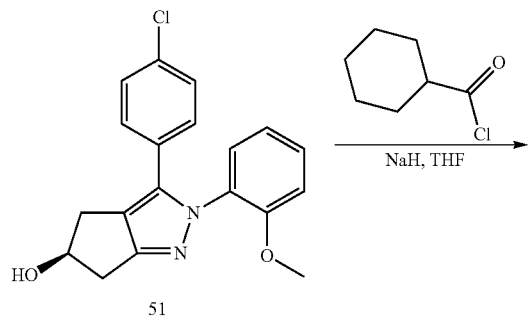

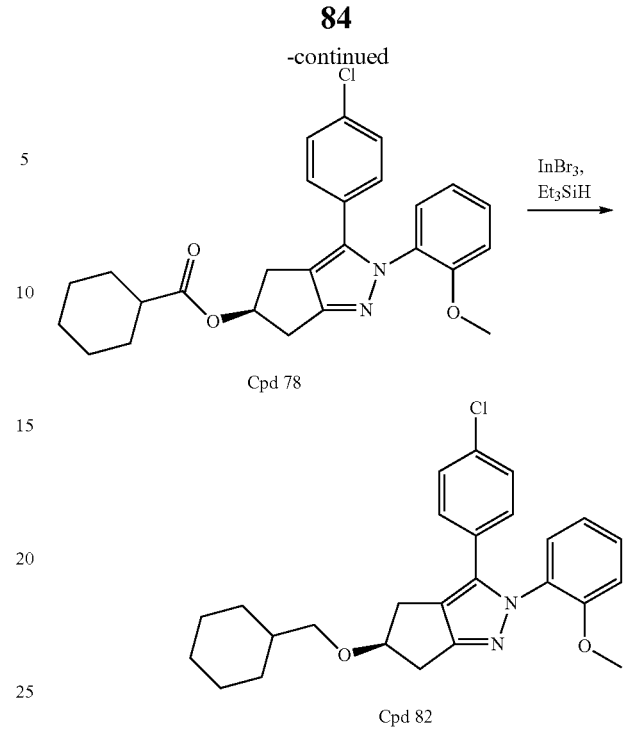

A. To a solution of compound 5l (40 mg, 0.12 mmol, 1 eq) in THF (2 mL) was added sodium hydride (23 mg of 60% dispersion in oil, 0.59 mmol, 5 eq). After 30 min, cyclohexanecarbonyl chloride (0.08 mL, 0.59 mmol, 5 eq) was added and the solution was stirred overnight at rt. Saturated NH$_4$Cl was added and the solution was poured onto a 5 mL extraction tube filled with diatomaceous earth. The extraction tube filled with diatomaceous earth was washed with DCM and the filtrate was concentrated. Purification by column chromatography (8 g), eluting with 20 to 40% EA/hexanes, gave compound 78 (30 mg, 56%) $^1$H NMR (CHLOROFORM-d) δ: 7.39 (dd, J=7.8, 1.5 Hz, 1H), 7.32-7.38 (m, 1H), 7.17-7.24 (m, 2H), 7.04-7.09 (m, 2H), 7.02 (td, J=7.6, 1.1 Hz, 1H), 6.89 (dd, J=8.3, 1.0 Hz, 1H), 5.82 (tt, J=7.3, 3.9 Hz, 1H), 3.50 (s, 3H), 3.27-3.39 (m, 2H), 2.75-2.94 (m, 2H), 2.32 (tt, J=11.2, 3.7 Hz, 1H), 1.92 (d, J=12.9 Hz, 2H), 1.71-1.80 (m, 2H), 1.61-1.68 (m, 1H), 1.40-1.52 (m, 2H), 1.22-1.35 (m, 3H). ESI-MS (m/z): Calcd. for C26H27ClN2O3: 451.2 (M+1). found: 451.2.

B. To a solution of compound 78 (21 mg, 0.047 mmol, 1 eq) in chloroform (1 mL) at rt was added triethylsilane (0.3 mL, 1.86 mmol, 40 eq) followed by indium bromide (330 mg, 0.93 mmol, 20 eq). The suspension was placed under an Argon atmosphere in a vial and stirred overnight at 65° C. Water was added and the mixture was stirred until the orange color disappeared. The reaction mixture was poured onto a 5 mL extraction tube filled with diatomaceous earth, the tube was flushed with DCM, and the filtrate was concentrated. Purification by column chromatography (8 g), eluting with 10 to 20% EA/hexanes, gave compound 82 (4.8 mg, 23%). $^1$H NMR (CHLOROFORM-d) δ: 7.29-7.43 (m, 2H), 7.16-7.23 (m, J=8.6 Hz, 2H), 7.04-7.10 (m, J=8.6 Hz, 2H), 7.01 (t, J=7.6 Hz, 1H), 6.87 (d, J=8.1 Hz, 1H), 4.59-4.70 (m, 1H), 3.49 (s, 3H), 3.27-3.37 (m, 2H), 3.10-3.22 (m, 2H), 2.84 (ddd, J=21.6, 15.9, 5.2 Hz, 2H), 1.59-1.84 (m, 6H), 1.17-1.33 (m, 3H), 0.89-1.01 (m, 2H). ESI-MS (m/z): Calcd. for C26H29ClN2O2: 437.2 (M+1). found: 437.2.

Following the procedure described above for Example 19 and substituting the appropriate reagents, starting materials and purification methods known to those skilled in the art, the following compounds were prepared:

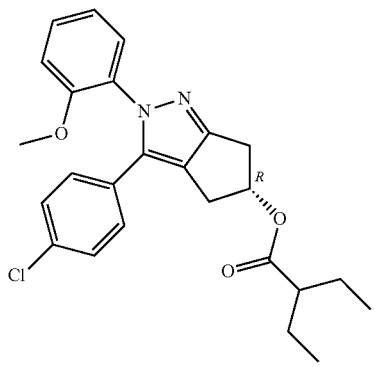

Cpd 55

Cpd 55: ¹H NMR (CHLOROFORM-d) δ: 7.39 (dd, J=7.7, 1.6 Hz, 1H), 7.32-7.38 (m, 1H), 7.17-7.24 (m, 2H), 7.05-7.10 (m, 2H), 6.98-7.05 (m, 1H), 6.89 (dd, J=8.3, 1.0 Hz, 1H), 5.87 (tt, J=7.5, 3.9 Hz, 1H), 3.50 (s, 3H), 3.29-3.41 (m, 2H), 2.78-2.96 (m, 2H), 2.23 (tt, J=8.6, 5.5 Hz, 1H), 1.46-1.73 (m, 4H), 0.91 (td, J=7.5, 1.0 Hz, 6H). ESI-MS (m/z): Calcd. for C25H27ClN2O3: 439.2 (M+1). found: 439.2.

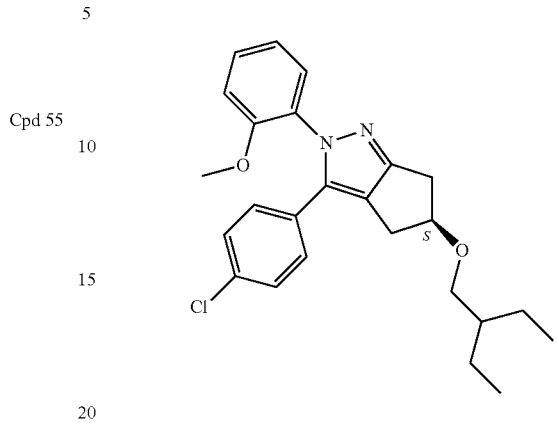

Cpd 72

Cpd 72: ¹H NMR (CHLOROFORM-d) δ: 7.30-7.41 (m, 2H), 7.16-7.22 (m, 2H), 7.04-7.10 (m, 2H), 7.01 (td, J=7.7, 1.3 Hz, 1H), 6.88 (dd, J=8.3, 1.0 Hz, 1H), 4.61-4.70 (m, 1H), 3.49 (s, 3H), 3.36-3.45 (m, 2H), 3.11-3.23 (m, 2H), 2.77-2.91 (m, 2H), 1.29-1.54 (m, 5H), 0.90 (t, J=7.5 Hz, 6H). ESI-MS (m/z): Calcd. for C25H29ClN2O2: 425.2 (M+1). found: 425.2.

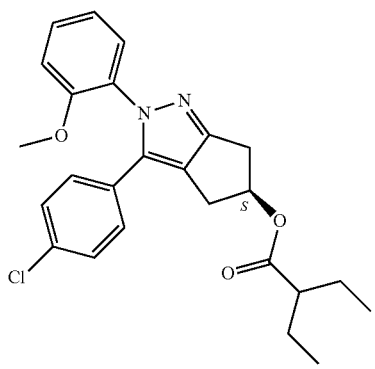

Cpd 70

Cpd 70: ¹H NMR (CHLOROFORM-d) δ: 7.39 (dd, J=7.7, 1.6 Hz, 1H), 7.32-7.38 (m, 1H), 7.16-7.24 (m, 2H), 7.05-7.10 (m, 2H), 7.02 (td, J=7.6, 1.1 Hz, 1H), 6.86-6.92 (m, 1H), 5.82-5.91 (m, 1H), 3.47-3.53 (m, 3H), 3.30-3.40 (m, 2H), 2.78-2.96 (m, 2H), 2.23 (tt, J=8.6, 5.6 Hz, 1H), 1.47-1.72 (m, 4H), 0.86-0.96 (m, 6H). ESI-MS (m/z): Calcd. for C25H27ClN2O3: 439.2 (M+1). found: 439.2.

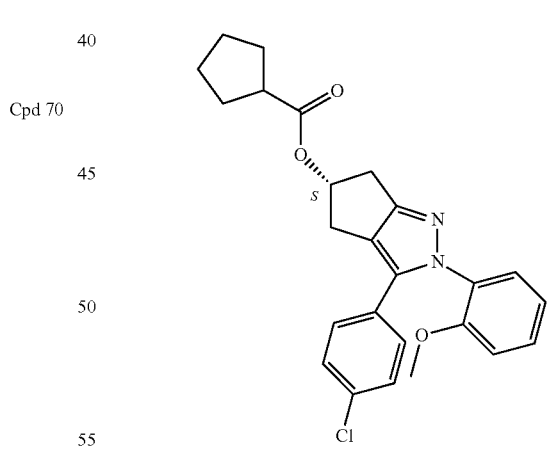

Cpd 79

Cpd 79: ¹H NMR (CHLOROFORM-d) δ: 7.32-7.42 (m, 2H), 7.17-7.23 (m, 2H), 7.05-7.09 (m, 2H), 6.99-7.05 (m, 1H), 6.89 (dd, J=8.3, 1.0 Hz, 1H), 5.83 (tt, J=7.4, 3.9 Hz, 1H), 3.50 (s, 3H), 3.34 (dd, J=16.7, 7.3 Hz, 2H), 2.80-2.95 (m, 2H), 2.75 (quin, J=8.0 Hz, 1H), 1.56-1.96 (m, 8H). ESI-MS (m/z): Calcd. for C25H25ClN2O3: 437.2 (M+1). found: 437.2.

87

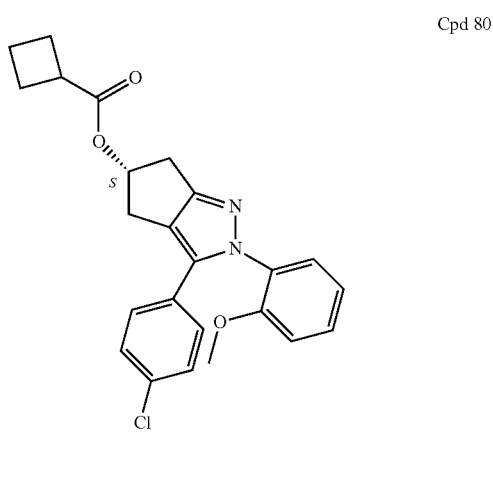
Cpd 80

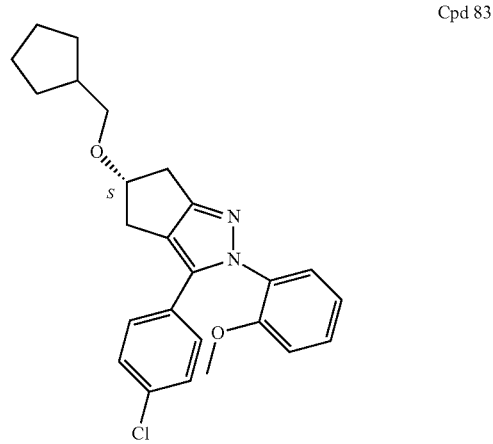
Cpd 83

Cpd 80: ¹H NMR (CHLOROFORM-d) δ: 7.39 (dd, J=7.7, 1.6 Hz, 1H), 7.35 (td, J=7.9, 1.6 Hz, 1H), 7.17-7.23 (m, 2H), 7.04-7.09 (m, 2H), 7.02 (td, J=7.6, 1.1 Hz, 1H), 6.86-6.92 (m, 1H), 5.83 (tt, J=7.3, 3.8 Hz, 1H), 3.50 (s, 3H), 3.34 (dd, J=16.7, 7.3 Hz, 2H), 3.16 (quin, J=8.3 Hz, 1H), 2.78-2.96 (m, 2H), 2.13-2.37 (m, 4H), 1.84-2.04 (m, 2H). ESI-MS (m/z): Calcd. for C24H23ClN2O3: 423.1 (M+1). found: 423.1.

Cpd 83: ¹H NMR (CHLOROFORM-d) δ: 7.38 (dd, J=7.7, 1.6 Hz, 1H), 7.30-7.36 (m, 1H), 7.16-7.23 (m, 2H), 7.04-7.10 (m, J=8.6 Hz, 2H), 7.01 (td, J=7.6, 1.0 Hz, 1H), 6.88 (d, J=8.3 Hz, 1H), 4.63-4.72 (m, 1H), 3.46-3.51 (m, 3H), 3.35-3.45 (m, 2H), 3.11-3.23 (m, 2H), 2.77-2.93 (m, 2H), 2.18 (dt, J=15.0, 7.4 Hz, 1H), 1.70-1.83 (m, 2H), 1.47-1.65 (m, 4H), 1.19-1.33 (m, 2H). ESI-MS (m/z): Calcd. for C25H27ClN2O2: 423.2 (M+1). found: 423.2.

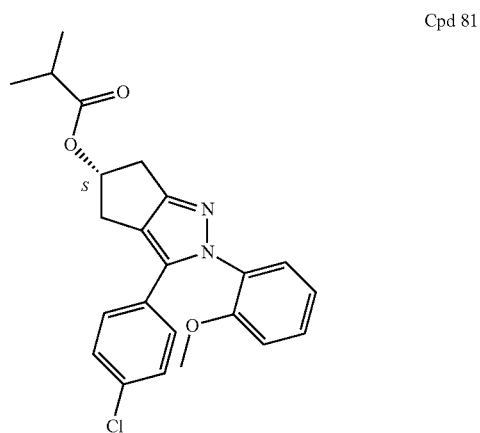
Cpd 81

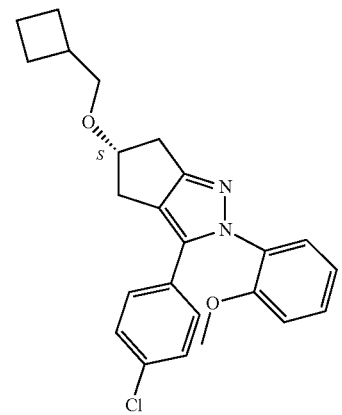
Cpd 84

Cpd 81: ¹H NMR (CHLOROFORM-d) δ: 7.31-7.43 (m, 2H), 7.16-7.24 (m, J=8.6 Hz, 2H), 7.05-7.10 (m, J=8.3 Hz, 2H), 7.02 (t, J=7.6 Hz, 1H), 6.89 (d, J=8.3 Hz, 1H), 5.83 (tt, J=7.3, 3.8 Hz, 1H), 3.50 (s, 3H), 3.34 (dd, J=16.7, 7.3 Hz, 2H), 2.77-2.96 (m, 2H), 2.57 (dt, J=14.0, 6.9 Hz, 1H), 1.19 (dd, J=7.1, 1.0 Hz, 6H). ESI-MS (m/z): Calcd. for C23H23ClN2O3: 411.1 (M+1). found: 411.1.

Cpd 84: ¹H NMR (CHLOROFORM-d) δ: 7.38 (dd, J=7.7, 1.6 Hz, 1H), 7.30-7.36 (m, 1H), 7.16-7.23 (m, 2H), 7.04-7.09 (m, 2H), 7.01 (td, J=7.6, 1.1 Hz, 1H), 6.88 (d, J=8.3 Hz, 1H), 4.62-4.72 (m, 1H), 3.43-3.57 (m, 5H), 3.11-3.23 (m, 2H), 2.76-2.92 (m, 2H), 2.60 (dt, J=14.8, 7.4 Hz, 1H), 2.03-2.15 (m, 2H), 1.83-2.00 (m, 2H), 1.69-1.81 (m, 2H). ESI-MS (m/z): Calcd. for C24H25ClN2O2: 409.2 (M+1). found: 409.2.

Cpd 85

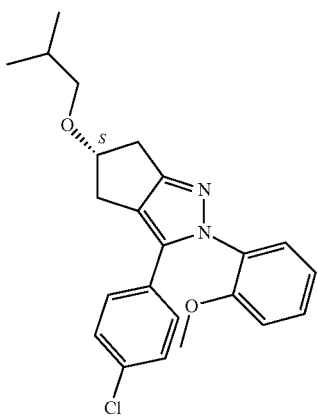

Cpd 87

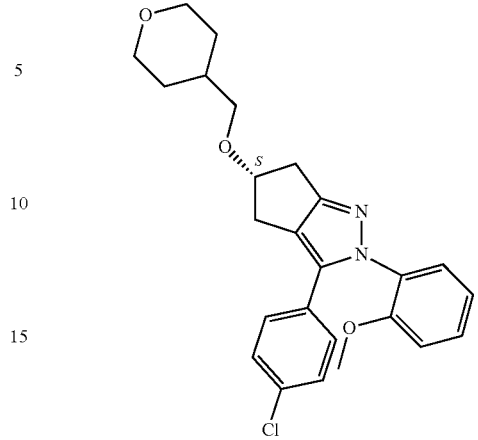

Cpd 87: ¹H NMR (CHLOROFORM-d) δ: 7.30-7.42 (m, 2H), 7.16-7.23 (m, J=8.6 Hz, 2H), 7.04-7.10 (m, J=8.3 Hz, 2H), 7.01 (t, J=7.6 Hz, 1H), 6.88 (d, J=8.3 Hz, 1H), 4.61-4.71 (m, 1H), 3.98 (dd, J=11.2, 3.9 Hz, 2H), 3.49 (s, 3H), 3.33-3.45 (m, 4H), 3.11-3.23 (m, 2H), 2.76-2.91 (m, 2H), 1.87 (br. s., 1H), 1.67 (br. s., 2H), 1.29-1.43 (m, 2H). ESI-MS (m/z): Calcd. for C25H27ClN2O3: 439.2 (M+1). found: 439.2.

Cpd 85: ¹H NMR (CHLOROFORM-d) δ: 7.30-7.45 (m, 2H), 7.20 (d, J=8.6 Hz, 2H), 7.05-7.13 (m, 2H), 6.97-7.05 (m, 1H), 6.88 (d, J=8.3 Hz, 1H), 4.62-4.74 (m, 1H), 3.49 (s, 3H), 3.25-3.37 (m, 2H), 3.11-3.25 (m, 2H), 2.76-2.96 (m, 2H), 1.81-1.98 (m, 1H), 0.94 (d, J=6.6 Hz, 6H). ESI-MS (m/z): Calcd. for C23H25ClN2O2: 397.2 (M+1). found: 397.2.

Example 20

Cpd 86

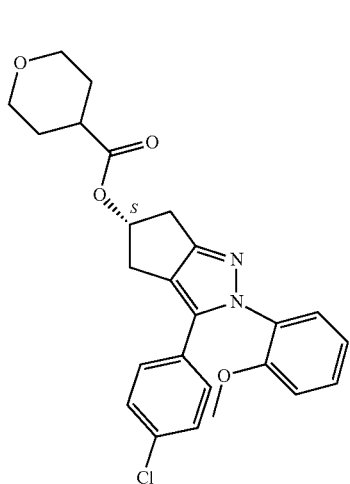

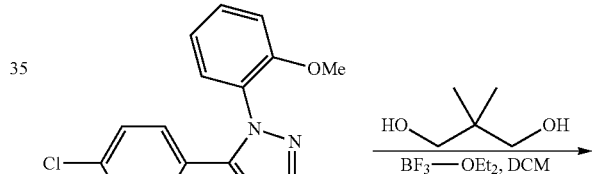

Cpd 35

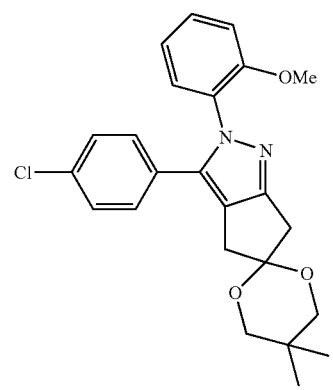

Cpd 71

Cpd 86: ¹H NMR (CHLOROFORM-d) δ: 7.32-7.42 (m, 2H), 7.17-7.23 (m, 2H), 7.05-7.09 (m, 2H), 6.99-7.05 (m, 1H), 6.89 (dd, J=8.3, 1.0 Hz, 1H), 5.85 (tt, J=7.3, 3.7 Hz, 1H), 3.97 (d, J=11.9 Hz, 2H), 3.50 (s, 3H), 3.29-3.48 (m, 4H), 2.78-2.95 (m, 2H), 2.51-2.62 (m, 1H), 1.73-1.90 (m, 4H). ESI-MS (m/z): Calcd. for C25H25ClN2O4: 453.2 (M+1). found: 453.2.

To a solution of compound 35 (24 mg, 0.07 mmol, 1 eq) and 2,2-dimethyl-1,3-propanediol (148 mg, 1.42 mmol, 20 eq) in DCM (1 mL) was added BF₃-etherate (0.009 mL, 0.07 mmol, 1 eq) and the solution was stirred overnight at rt. Water was added, and the aqueous phase was extracted with EA. The organic phases were combined, washed with brine, dried and over MgSO₄, filtered, and concentrated. Purification by column chromatography (8 g), eluting with 15 to 30% EA/hexanes, gave compound 71 (27.8 mg, 88%). ¹H NMR (CHLOROFORM-d) δ: 7.38 (dd, J=7.7, 1.6 Hz, 1H), 7.30-7.36 (m, 1H), 7.16-7.23 (m, 2H), 7.03-7.09 (m, 2H), 7.01 (td, J=7.6, 1.1 Hz, 1H), 6.84-6.89 (m, 1H), 3.61 (q, J=11.1 Hz, 4H), 3.47 (s, 3H), 3.26 (s, 2H), 3.20 (s, 2H), 1.08 (s, 3H), 1.00 (s, 3H). ESI-MS (m/z): Calcd. for C24H25ClN2O3: 425.2 (M+1). found: 425.2.

Following the procedure described above for Example 20 and substituting the appropriate reagents, starting materials and purification methods known to those skilled in the art, the following compounds were prepared:

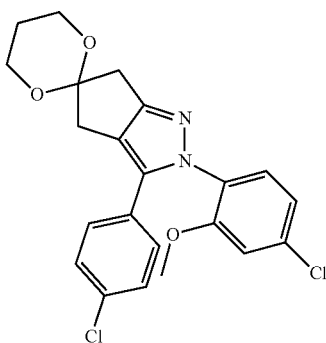

Cpd 52

Cpd 52: ¹H NMR (CHLOROFORM-d) δ: 7.33 (d, J=8.3 Hz, 1H), 7.19-7.26 (m, 2H), 7.03-7.08 (m, 2H), 7.00 (dd, J=8.3, 2.0 Hz, 1H), 6.85 (d, J=2.0 Hz, 1H), 3.95-4.09 (m, 4H), 3.47 (s, 3H), 3.27 (s, 2H), 3.18 (s, 2H), 1.83-1.97 (m, 1H), 1.69-1.81 (m, 1H). ESI-MS (m/z): Calcd. for C22H2OCl2N2O3: 431.1 (M+1). found: 431.1.

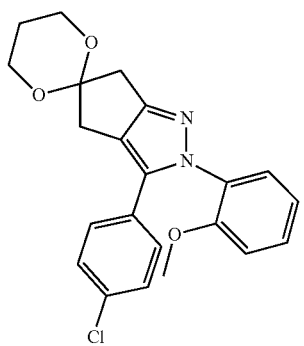

Cpd 54

Cpd 54: ¹H NMR (CHLOROFORM-d) δ: 7.38 (dd, J=7.8, 1.8 Hz, 1H), 7.34 (td, J=8.0, 1.8 Hz, 1H), 7.17-7.23 (m, 2H), 7.03-7.08 (m, 2H), 7.01 (td, J=7.6, 1.1 Hz, 1H), 6.87 (dd, J=8.3, 1.0 Hz, 1H), 3.97-4.09 (m, 4H), 3.47 (s, 3H), 3.28 (s, 2H), 3.19 (s, 2H), 1.84-1.97 (m, 1H), 1.69-1.80 (m, 1H). ESI-MS (m/z): Calcd. for C22H21ClN2O3: 397.1 (M+1). found: 397.1.

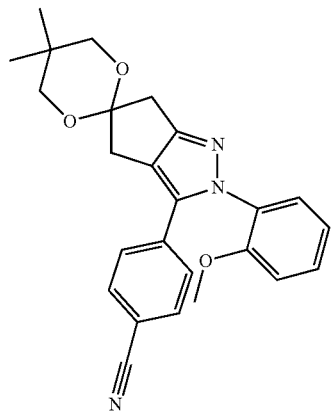

Cpd 91

Cpd 91: ¹H NMR (CHLOROFORM-d) δ: 7.49-7.55 (m, J=8.3 Hz, 2H), 7.42 (dd, J=7.8, 1.5 Hz, 1H), 7.32-7.40 (m, 1H), 7.20-7.25 (m, J=8.3 Hz, 2H), 7.04 (t, J=7.7 Hz, 1H), 6.87 (d, J=8.3 Hz, 1H), 3.62 (q, J=11.4 Hz, 4H), 3.45 (s, 3H), 3.25 (d, J=15.7 Hz, 4H), 1.09 (s, 3H), 1.00 (s, 3H). ESI-MS (m/z): Calcd. for C25H25N3O3: 416.2 (M+1). found: 416.2.

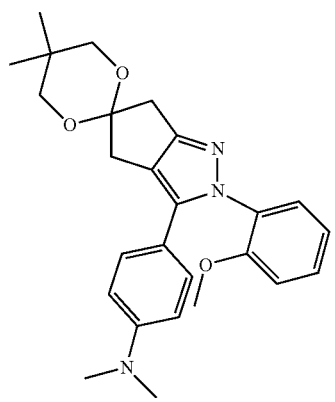

Cpd 93

Cpd 93: ¹H NMR (CHLOROFORM-d) δ: 7.29-7.39 (m, 2H), 6.94-7.05 (m, 3H), 6.90 (d, J=8.1 Hz, 1H), 6.56 (d, J=8.8 Hz, 2H), 3.57-3.69 (m, 4H), 3.55 (s, 3H), 3.23 (d, J=11.4 Hz, 4H), 2.91 (s, 6H), 1.07 (s, 3H), 1.00 (s, 3H). ESI-MS (m/z): Calcd. for C26H31N3O3: 434.2 (M+1). found: 434.2.

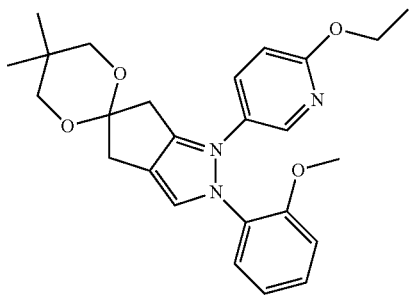

Cpd 94

Cpd 94: ¹H NMR (CHLOROFORM-d) δ: 8.02 (d, J=2.3 Hz, 1H), 7.30-7.41 (m, 2H), 7.22-7.27 (m, 1H), 7.00 (t, J=7.3 Hz, 1H), 6.89 (d, J=8.3 Hz, 1H), 6.56 (d, J=8.6 Hz, 1H), 4.31

(q, J=7.0 Hz, 2H), 3.56-3.68 (m, 4H), 3.54 (s, 3H), 3.26 (s, 2H), 3.21 (s, 2H), 1.36 (t, J=7.1 Hz, 3H), 1.07 (s, 3H), 1.01 (s, 3H). ESI-MS (m/z): Calcd. for C25H29N3O4: 436.2 (M+1). found: 436.2.

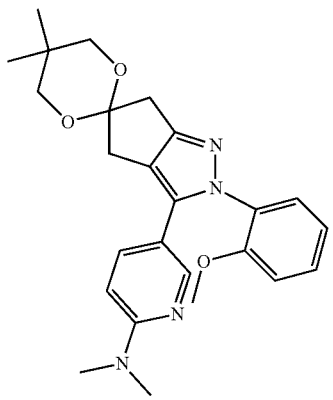

Cpd 97

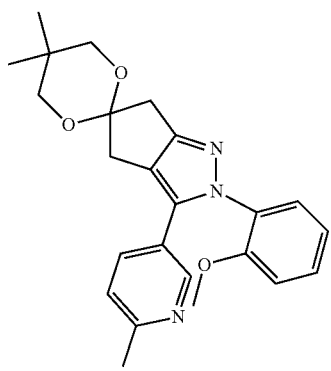

Cpd 95

Cpd 97: ¹H NMR (CHLOROFORM-d) δ: 8.08 (d, J=2.3 Hz, 1H), 7.29-7.39 (m, 2H), 7.10 (dd, J=9.0, 2.4 Hz, 1H), 6.98 (t, J=7.6 Hz, 1H), 6.91 (d, J=8.1 Hz, 1H), 6.33 (d, J=9.1 Hz, 1H), 3.53-3.67 (m, 7H), 3.25 (s, 2H), 3.21 (s, 2H), 3.05 (s, 6H), 1.05 (s, 3H), 1.01 (s, 3H). ESI-MS (m/z): Calcd. for C25H30N4O3: 435.2 (M+1). found: 435.2.

Cpd 95: ¹H NMR (CHLOROFORM-d) δ: 8.31-8.41 (m, 1H), 7.31-7.44 (m, 2H), 7.25 (d, J=2.3 Hz, 1H), 6.96-7.06 (m, 2H), 6.88 (d, J=8.3 Hz, 1H), 3.62 (q, J=11.3 Hz, 4H), 3.51 (s, 3H), 3.27 (s, 2H), 3.23 (s, 2H), 2.50 (s, 3H), 1.08 (s, 3H), 1.00 (s, 3H). ESI-MS (m/z): Calcd. for C24H27N3O3: 406.2 (M+1). found: 406.2.

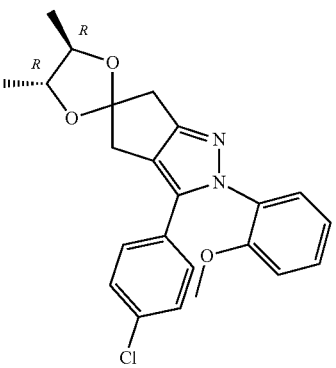

Cpd 98

Cpd 98: ¹H NMR (CHLOROFORM-d) δ: 7.38 (dd, J=7.7, 1.6 Hz, 1H), 7.30-7.36 (m, 1H), 7.16-7.22 (m, J=8.6 Hz, 2H), 7.03-7.09 (m, 2H), 7.00 (t, J=7.6 Hz, 1H), 6.87 (d, J=8.1 Hz, 1H), 3.69-3.82 (m, 2H), 3.47 (s, 3H), 3.06-3.24 (m, 4H), 1.29-1.36 (m, 6H). ESI-MS (m/z): Calcd. for C23H23ClN2O3: 411.1 (M+1). found: 411.1.

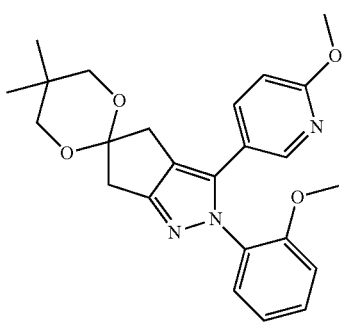

Cpd 96

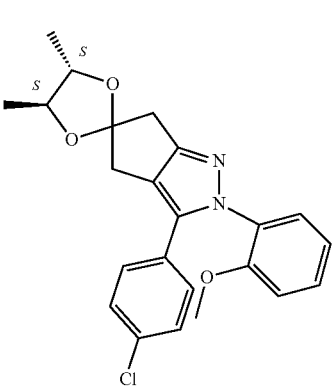

Cpd 99

Cpd 96: ¹H NMR (CHLOROFORM-d) δ: 8.04 (d, J=2.3 Hz, 1H), 7.30-7.41 (m, 2H), 7.22-7.29 (m, 3H), 7.00 (t, J=7.6 Hz, 1H), 6.89 (d, J=8.3 Hz, 1H), 6.59 (d, J=8.6 Hz, 1H), 3.90 (s, 3H), 3.56-3.68 (m, 4H), 3.54 (s, 3H), 3.26 (s, 2H), 3.21 (s, 2H), 1.07 (s, 3H), 1.01 (s, 3H). ESI-MS (m/z): Calcd. for C24H27N3O4: 422.2 (M+1). found: 422.2.

Cpd 99: ¹H NMR (CHLOROFORM-d) δ: 7.38 (dd, J=7.7, 1.6 Hz, 1H), 7.33 (td, J=7.9, 1.6 Hz, 1H), 7.16-7.23 (m, 2H), 7.03-7.09 (m, 2H), 7.01 (td, J=7.7, 1.3 Hz, 1H), 6.83-6.91 (m, 1H), 3.68-3.83 (m, 2H), 3.47 (s, 3H), 3.05-3.23 (m, 4H), 1.32 (dd, J=5.6, 1.5 Hz, 6H). ESI-MS (m/z): Calcd. for C23H23ClN2O3: 411.1 (M+1). found: 411.1.

Cpd 100

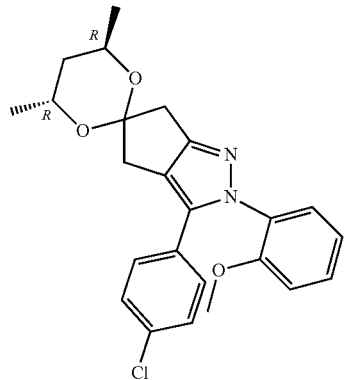

Cpd 100: ¹H NMR (CHLOROFORM-d) δ: 7.31 (dd, J=7.7, 1.6 Hz, 1H), 7.22-7.29 (m, 1H), 7.08-7.15 (m, J=8.6 Hz, 2H), 6.96-7.02 (m, J=8.3 Hz, 2H), 6.90-6.96 (m, 1H), 6.80 (d, J=8.3 Hz, 1H), 3.93-4.10 (m, 2H), 3.40 (s, 3H), 3.03-3.23 (m, 4H), 1.65 (t, J=7.3 Hz, 2H), 1.13-1.27 (m, 8H). ESI-MS (m/z): Calcd. for C24H25ClN2O3: 425.2 (M+1). found: 425.2.

Cpd 101

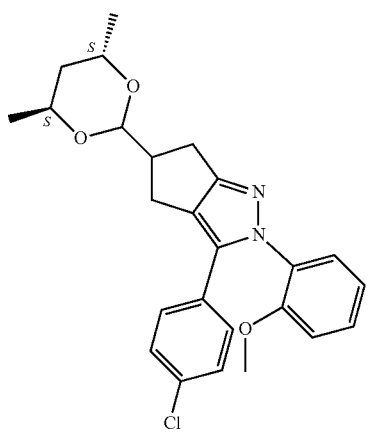

Cpd 101: ¹H NMR (CHLOROFORM-d) δ: 7.39 (dd, J=7.7, 1.6 Hz, 1H), 7.30-7.36 (m, 1H), 7.15-7.21 (m, 2H), 7.03-7.08 (m, 2H), 7.00 (td, J=7.6, 1.1 Hz, 1H), 6.87 (d, J=8.3 Hz, 1H), 4.04-4.17 (m, 2H), 3.47 (s, 3H), 3.09-3.30 (m, 4H), 1.72 (t, J=7.2 Hz, 2H), 1.22-1.29 (m, 8H). ESI-MS (m/z): Calcd. for C24H25ClN2O3: 425.2 (M+1). found: 425.2.

Cpd 102

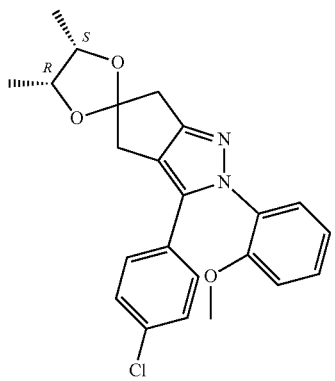

Cpd 102: ¹H NMR (CHLOROFORM-d) δ: 7.30-7.41 (m, 2H), 7.15-7.23 (m, J=8.6 Hz, 2H), 7.04-7.10 (m, J=8.6 Hz, 2H), 7.00 (t, J=7.6 Hz, 1H), 6.87 (d, J=8.3 Hz, 1H), 4.27-4.37 (m, 2H), 3.48 (s, 3H), 3.20 (br. s, 2H), 3.10 (s, 2H), 1.21 (d, J=6.1 Hz, 6H). ESI-MS (m/z): Calcd. for C23H23ClN2O3: 411.1 (M+1). found: 411.1.

Cpd 103

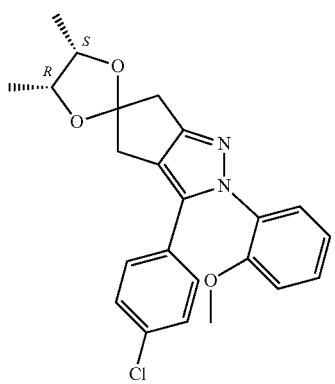

Cpd 103: ¹H NMR (CHLOROFORM-d) δ: 7.39 (dd, J=7.7, 1.6 Hz, 1H), 7.30-7.37 (m, 1H), 7.16-7.23 (m, 2H), 7.04-7.09 (m, 2H), 6.98-7.04 (m, 1H), 6.87 (d, J=8.3 Hz, 1H), 4.31 (dt, J=5.9, 4.5 Hz, 2H), 3.48 (s, 3H), 3.24 (s, 2H), 3.06 (s, 2H), 1.22 (d, J=6.1 Hz, 6H). ESI-MS (m/z): Calcd. for C23H23ClN2O3: 411.1 (M+1). found: 411.1.

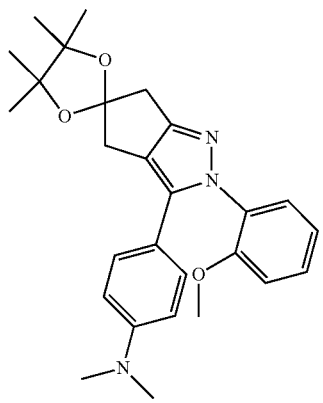

Cpd 107

Cpd 107: ¹H NMR (CHLOROFORM-d) δ: 7.28-7.37 (m, 2H), 6.93-7.03 (m, 3H), 6.89 (d, J=8.1 Hz, 1H), 6.56 (d, J=8.8 Hz, 2H), 3.53 (s, 3H), 3.11-3.22 (m, 4H), 2.91 (s, 6H), 1.26-1.32 (m, 12H). ESI-MS (m/z): Calcd. for C27H33N3O3: 448.3 (M+1). found: 448.3.

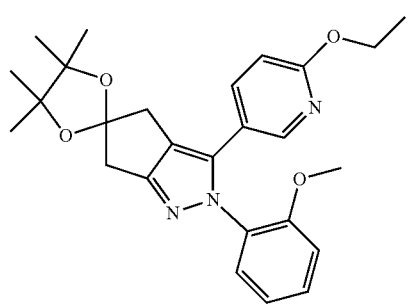

Cpd 108

Cpd 108: ¹H NMR (CHLOROFORM-d) δ: 8.02 (d, J=2.5 Hz, 1H), 7.29-7.39 (m, 2H), 7.23 (dd, J=8.6, 2.5 Hz, 1H), 6.95-7.04 (m, 1H), 6.88 (d, J=7.6 Hz, 1H), 6.55 (d, J=8.6 Hz, 1H), 4.30 (q, J=7.1 Hz, 2H), 3.53 (s, 3H), 3.09-3.26 (m, 4H), 1.36 (t, J=7.1 Hz, 3H), 1.28 (d, J=6.3 Hz, 12H). ESI-MS (m/z): Calcd. for C26H31N3O4: 450.2 (M+1). found: 450.2.

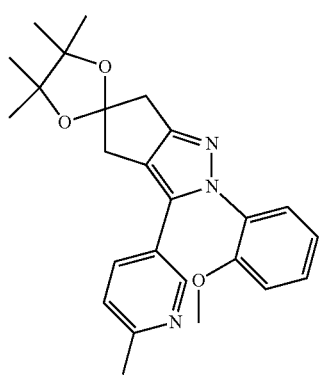

Cpd 109

Cpd 109: ¹H NMR (CHLOROFORM-d) δ: 8.36 (d, J=1.8 Hz, 1H), 7.29-7.41 (m, 2H), 7.23 (dd, J=8.1, 2.3 Hz, 1H), 6.95-7.04 (m, 2H), 6.87 (d, J=8.1 Hz, 1H), 3.50 (s, 3H), 3.12-3.27 (m, 4H), 2.50 (s, 3H), 1.29 (d, J=6.6 Hz, 12H). ESI-MS (m/z): Calcd. for C25H29N3O3: 420.2 (M+1). found: 420.2.

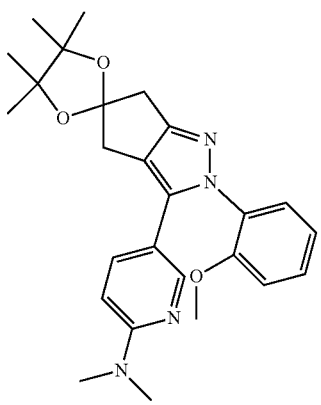

Cpd 110

Cpd 110: ¹H NMR (CHLOROFORM-d) δ: 8.09 (d, J=2.0 Hz, 1H), 7.28-7.36 (m, 2H), 7.07 (dd, J=9.0, 2.4 Hz, 1H), 6.94-7.01 (m, 1H), 6.91 (d, J=8.6 Hz, 1H), 6.32 (d, J=8.8 Hz, 1H), 3.58 (s, 3H), 3.18 (d, J=6.8 Hz, 4H), 3.05 (s, 6H), 1.28 (d, J=6.6 Hz, 12H). ESI-MS (m/z): Calcd. for C26H32N4O3: 449.3 (M+1). found: 449.3.

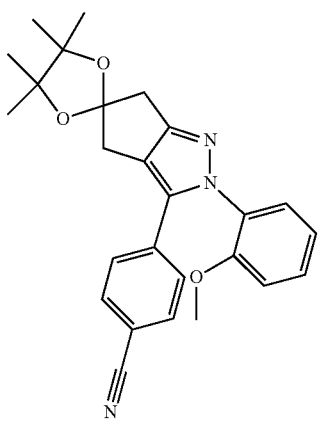

Cpd 111

Cpd 111: ¹H NMR (CHLOROFORM-d) δ: 7.51 (d, J=8.1 Hz, 2H), 7.32-7.49 (m, 2H), 7.21 (d, J=8.3 Hz, 2H), 7.05 (d, J=7.6 Hz, 1H), 6.87 (d, J=8.3 Hz, 1H), 3.44 (s, 3H), 3.12-3.33 (m, 4H), 1.21-1.43 (m, 12H). ESI-MS (m/z): Calcd. for C26H27N3O3: 430.2 (M+1). found: 430.2.

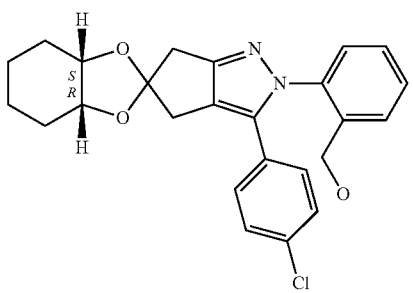

Cpd 112

Cpd 112: ¹H NMR (CHLOROFORM-d) δ: 7.30-7.41 (m, 2H), 7.16-7.23 (m, 2H), 7.04-7.10 (m, J=8.6 Hz, 2H), 6.97-7.04 (m, 1H), 6.87 (d, J=8.3 Hz, 1H), 4.14-4.22 (m, 2H), 3.48 (s, 3H), 3.25 (br. s., 2H), 3.11 (s, 2H), 1.75-1.85 (m, 4H), 1.50-1.60 (m, 2H), 1.27-1.40 (m, 2H). ESI-MS (m/z): Calcd. for C25H25ClN2O3: 437.2 (M+1). found: 437.2.

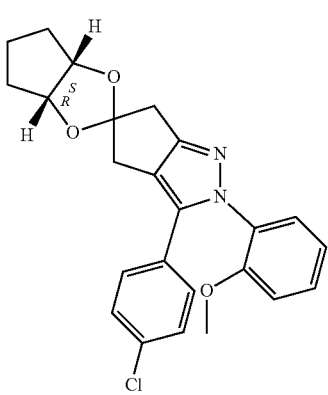

Cpd 114

Cpd 114: ¹H NMR (CHLOROFORM-d) δ: 7.38 (dd, J=7.7, 1.6 Hz, 1H), 7.30-7.36 (m, 1H), 7.16-7.22 (m, 2H), 7.03-7.08 (m, 2H), 6.97-7.03 (m, 1H), 6.84-6.89 (m, 1H), 4.70 (d, J=3.9 Hz, 2H), 3.47 (s, 3H), 3.27 (s, 2H), 3.02 (s, 2H), 1.96 (dd, J=13.6, 6.2 Hz, 2H), 1.81 (tt, J=12.3, 6.0 Hz, 2H), 1.61 (dt, J=12.3, 6.3 Hz, 1H), 1.38-1.54 (m, 1H). ESI-MS (m/z): Calcd. for C24H23ClN2O3: 423.1 (M+1). found: 423.1.

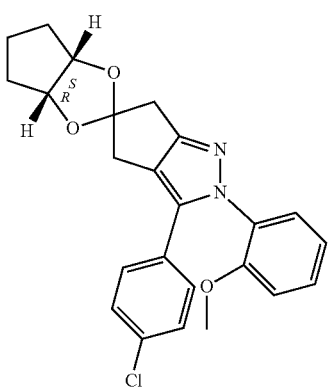

Cpd 115

Cpd 115: ¹H NMR (CHLOROFORM-d) δ: 7.30-7.41 (m, 2H), 7.16-7.22 (m, 2H), 7.04-7.09 (m, 2H), 6.98-7.04 (m, 1H), 6.84-6.90 (m, 1H), 4.72 (d, J=4.4 Hz, 2H), 3.48 (s, 3H), 3.16-3.28 (m, 2H), 3.06 (s, 2H), 1.95 (dd, J=13.7, 5.9 Hz, 2H), 1.78 (d, J=6.1 Hz, 1H), 1.61 (dt, J=12.2, 6.3 Hz, 1H), 1.41-1.54 (m, 2H). ESI-MS (m/z): Calcd. for C24H23ClN2O3: 423.1 (M+1). found: 423.1.

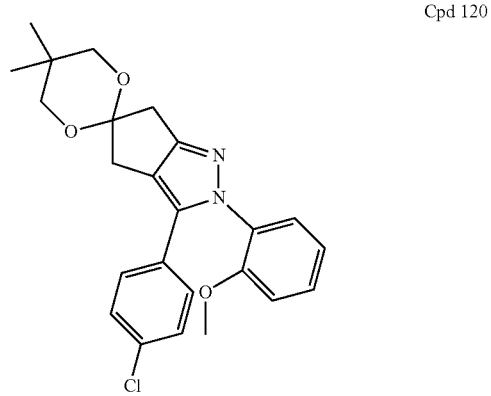 [SMILES: COc1ccccc1-n1nc2c(c1-c1ccc(Cl)cc1)CC1(C2)OCC(C)(C)CO1]

Cpd 120

Cpd 120: ¹H NMR (CHLOROFORM-d) δ: 7.45 (t, J=8.0 Hz, 1H), 7.36 (d, J=7.4 Hz, 1H), 7.05 (t, J=7.6 Hz, 1H), 7.00 (d, J=8.6 Hz, 1H), 6.71 (d, J=3.9 Hz, 1H), 6.53 (d, J=3.9 Hz, 1H), 3.69 (s, 3H), 3.56-3.67 (m, 4H), 3.23 (d, J=7.4 Hz, 4H), 1.09 (s, 3H), 1.00 (s, 3H). ESI-MS (m/z): Calcd. for C22H23ClN2O3S: 431.1 (M+1). found: 431.1.

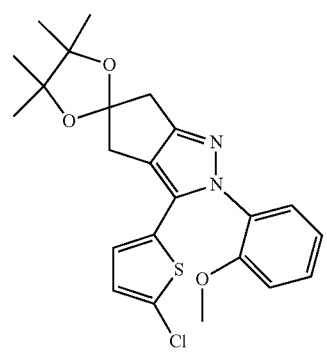

Cpd 121

Cpd 121: ¹H NMR (CHLOROFORM-d) δ: 7.41-7.51 (m, 1H), 7.35 (dd, J=7.8, 1.7 Hz, 1H), 7.02-7.10 (m, 1H), 6.99 (d, J=8.3 Hz, 1H), 6.70 (d, J=3.9 Hz, 1H), 6.50 (d, J=3.9 Hz, 1H), 3.68 (s, 3H), 3.18 (s, 4H), 1.30 (s, 12H). ESI-MS (m/z): Calcd. for C23H25ClN2O3S: 445.1 (M+1). found: 445.1.

Example 21

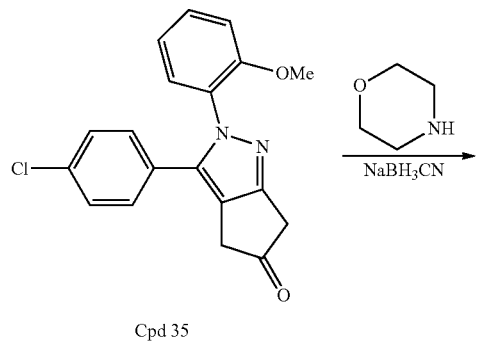

Cpd 35

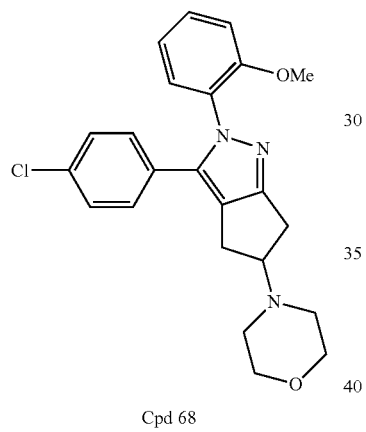

Cpd 68

To a solution of compound 35 (30 mg, 0.09 mmol, 1 eq) in DCM (2 mL) and acetic acid (0.01 mL) was added morpholine (16 mg, 0.18 mmol, 2 eq). After 30 min, sodium cyanoborohydride (22 mg, 0.35 mmol, 4 eq) was added and the solution was stirred overnight. DCM was added, and the reaction mixture was washed sequentially with NaHCO₃ and water, dried over MgSO₄, filtered, and concentrated. Purification by column chromatography (8 g), eluting with 50 to 100% EA/hexanes to 2 to 5% MeOH/DCM+1% NH₃ gave compound 68 (24.8 mg, 67%). ¹H NMR (CHLOROFORM-d) δ: 7.30-7.42 (m, 2H), 7.17-7.24 (m, 2H), 7.04-7.10 (m, J=8.6 Hz, 2H), 7.01 (td, J=7.6, 1.1 Hz, 1H), 6.88 (d, J=8.1 Hz, 1H), 3.79 (t, J=4.5 Hz, 4H), 3.59-3.71 (m, 1H), 3.49 (s, 3H), 2.94-3.10 (m, 2H), 2.77-2.92 (m, 2H), 2.62 (br. s., 4H). ESI-MS (m/z): Calcd. for C23H24ClN3O2: 410.2 (M+1). found: 410.2.

Following the procedure described above for Example 21 and substituting the appropriate reagents, starting materials and purification methods known to those skilled in the art, the following compounds were prepared:

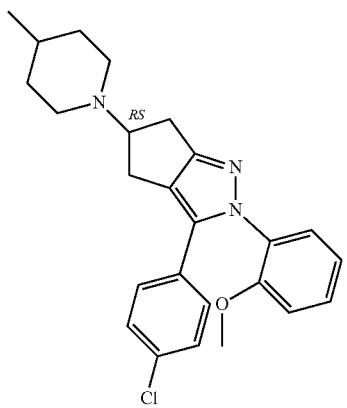

Cpd 117

Cpd 117: ¹H NMR (CHLOROFORM-d) δ: 7.29-7.42 (m, 2H), 7.21 (d, J=8.3 Hz, 2H), 7.07 (d, J=8.1 Hz, 2H), 7.01 (t, J=7.6 Hz, 1H), 6.88 (d, J=8.1 Hz, 1H), 3.54-3.92 (m, 2H), 3.49 (s, 3H), 2.80-3.17 (m, 3H), 2.14-2.31 (m, 2H), 1.73 (d, J=12.2 Hz, 2H), 1.31-1.54 (m, 3H), 0.97 (d, J=5.6 Hz, 3H). ESI-MS (m/z): Calcd. for C25H28ClN3O: 422.2 (M+1). found: 422.2.

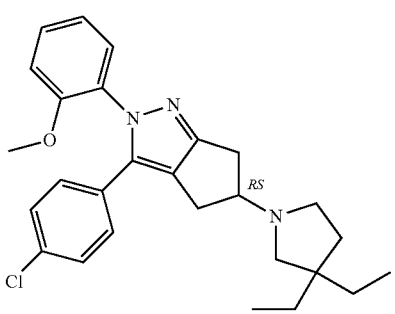

Cpd 118

Cpd 118: ¹H NMR (CHLOROFORM-d) δ: 7.30-7.40 (m, 2H), 7.17-7.23 (m, 2H), 7.04-7.09 (m, 2H), 7.01 (td, J=7.6, 1.1 Hz, 1H), 6.88 (d, J=7.6 Hz, 1H), 3.81 (t, J=7.9 Hz, 1H), 3.49 (s, 3H), 2.92-3.12 (m, 6H), 2.74 (q, J=10.3 Hz, 2H), 1.72 (t, J=7.0 Hz, 2H), 1.41-1.57 (m, 4H), 0.80-0.89 (m, 6H). ESI-MS (m/z): Calcd. for C27H32ClN3O: 450.2 (M+1). found: 450.2.

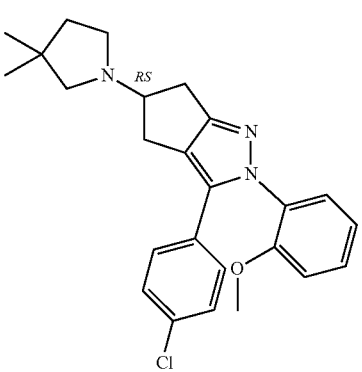

Cpd 119

Cpd 119: ¹H NMR (CHLOROFORM-d) δ: 7.38 (dd, J=7.7, 1.6 Hz, 1H), 7.30-7.36 (m, 1H), 7.16-7.23 (m, 2H), 7.04-7.10

(m, 2H), 6.97-7.04 (m, 1H), 6.87 (d, J=7.3 Hz, 1H), 3.56 (t, J=7.9 Hz, 1H), 3.49 (s, 3H), 2.90-3.05 (m, 2H), 2.79-2.90 (m, 2H), 2.69-2.79 (m, 2H), 2.47 (s, 2H), 1.65 (t, J=6.8 Hz, 2H), 1.13 (s, 6H). ESI-MS (m/z): Calcd. for C25H28ClN3O: 422.2 (M+1). found: 422.2.

Cpd 123

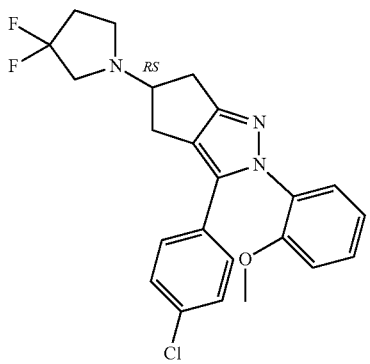

Cpd 123: $^1$H NMR (CHLOROFORM-d) δ: 7.30-7.42 (m, 2H), 7.17-7.25 (m, J=8.6 Hz, 2H), 7.04-7.10 (m, J=8.6 Hz, 2H), 7.01 (td, J=7.6, 1.1 Hz, 1H), 6.88 (d, J=8.3 Hz, 1H), 3.65 (quin, J=7.7 Hz, 1H), 3.49 (s, 3H), 2.92-3.13 (m, 4H), 2.74-2.92 (m, 4H), 2.25-2.42 (m, 2H). ESI-MS (m/z): Calcd. for C23H22ClF2N3O: 430.1 (M+1). found: 430.1.

Example 22

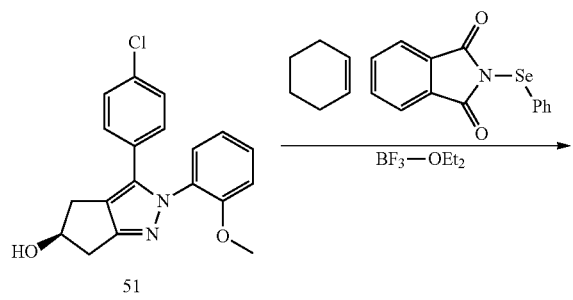

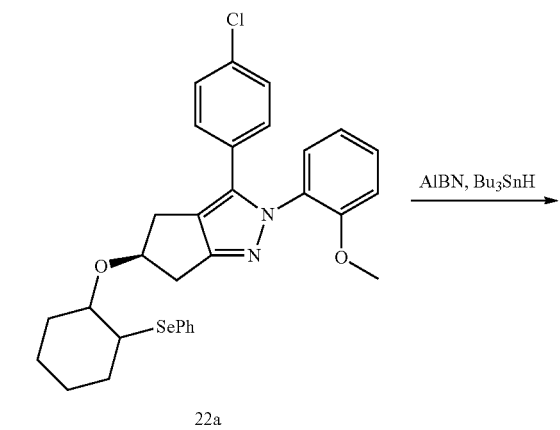

Cpd 88

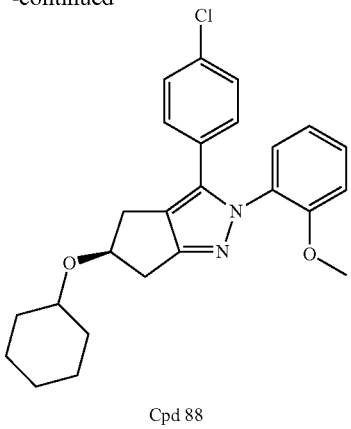

Cpd 88

A. To a suspension of compound 51 (50 mg, 0.15 mmol, 1 eq) in DCM (2 mL) was added cyclohexene (0.045 mL, 0.44 mmol, 3 eq), N-(phenylseleno)phthalimide (47 mg, 0.15 mmol, 1 eq) and BF$_3$-etherate (0.002 mL, 0.015 mmol, 0.1 eq). After 3 hrs, 1 N NaOH was added and the reaction mixture was extracted with DCM. The combined organic phase was dried over MgSO$_4$, filtered, and concentrated. Purification by column chromatography (12 g), eluting with 20 to 40% EA/hexanes, gave compound 22a (40 mg, 47%, mix of diastereomers). ESI-MS (m/z): Calcd. for C31H31ClN2O2Se: 579.1 (M+1). found: 579.1.

B. To a solution of compound 22a (40 mg, 0.07 mmol, 1 eq) in benzene (2 mL) was added Bu$_3$SnH (0.072 mL, 0.28 mmol, 4 eq) and AIBN (12 mg, 0.07 mmol, 1 eq) and the reaction mixture was heated to 80° C. in a vial overnight. The solution was concentrated, and purification by column chromatography (8 g), eluting with 7 to 15 to 20% EA/hexanes, gave impure compound 88. Further purification by HPLC eluting with 30 to 100% ACN/H$_2$O gave compound 88 in the desired purity (16 mg, 54%). $^1$H NMR (CHLOROFORM-d) δ: 7.37 (dd, J=7.7, 1.6 Hz, 1H), 7.33 (td, J=7.9, 1.6 Hz, 1H), 7.16-7.22 (m, 2H), 7.04-7.10 (m, 2H), 7.01 (td, J=7.6, 1.1 Hz, 1H), 6.84-6.90 (m, 1H), 4.78-4.87 (m, 1H), 3.49 (s, 3H), 3.35-3.45 (m, 1H), 3.10-3.23 (m, 2H), 2.75-2.90 (m, 2H), 1.97 (d, J=9.9 Hz, 2H), 1.74-1.81 (m, 2H), 1.55-1.61 (m, 1H), 1.14-1.41 (m, 5H). ESI-MS (m/z): Calcd. for C25H27ClN2O2: 423.2 (M+1). found: 423.2.

Following the procedure described above for Example 22 and substituting the appropriate reagents, starting materials and purification methods known to those skilled in the art, the following compounds were prepared:

Cpd 89

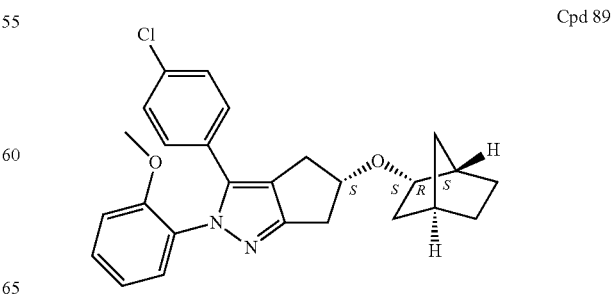

Cpd 89: $^1$H NMR (CHLOROFORM-d) δ: 7.38 (dd, J=7.8, 1.5 Hz, 1H), 7.30-7.37 (m, 1H), 7.20 (d, J=8.1 Hz, 2H), 7.07 (dd, J=8.6, 1.8 Hz, 2H), 6.98-7.04 (m, 1H), 6.88 (d, J=8.3 Hz, 1H), 4.68-4.78 (m, 1H), 3.54 (d, J=6.6 Hz, 1H), 3.49 (s, 3H), 3.10-3.23 (m, 2H), 2.74-2.91 (m, 2H), 2.36 (d, J=4.3 Hz, 1H), 2.26 (br. s., 1H), 1.39-1.68 (m, 5H), 0.98-1.16 (m, 3H). ESI-MS (m/z): Calcd. for C26H27ClN2O2: 435.2 (M+1). found: 435.2.

Cpd 90

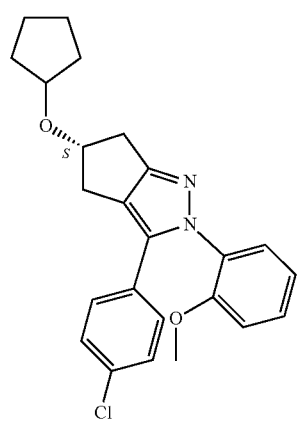

Cpd 90: $^1$H NMR (CHLOROFORM-d) δ: 7.30-7.41 (m, 2H), 7.17-7.23 (m, 2H), 7.05-7.10 (m, 2H), 6.99-7.04 (m, 1H), 6.88 (d, J=8.3 Hz, 1H), 4.68-4.77 (m, 1H), 4.04-4.13 (m, 1H), 3.50 (s, 3H), 3.11-3.24 (m, 2H), 2.84 (ddd, J=21.9, 15.7, 5.7 Hz, 2H), 1.48-1.87 (m, 6H), 0.81-1.03 (m, 2H). ESI-MS (m/z): Calcd. for C24H25ClN2O2: 409.2 (M+1). found: 409.2.

Example 23

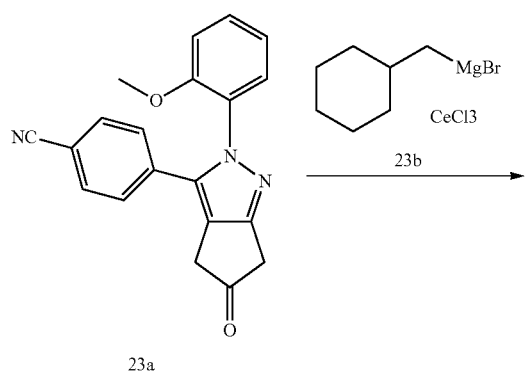

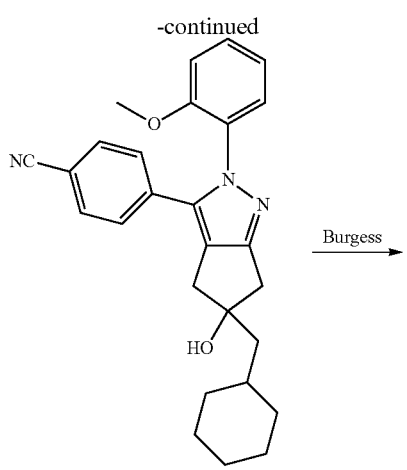

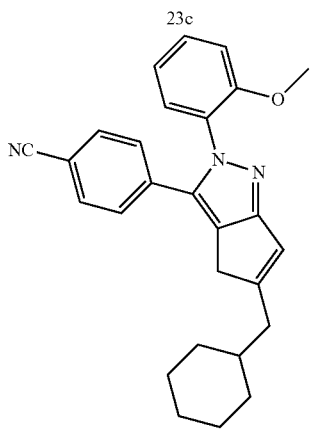

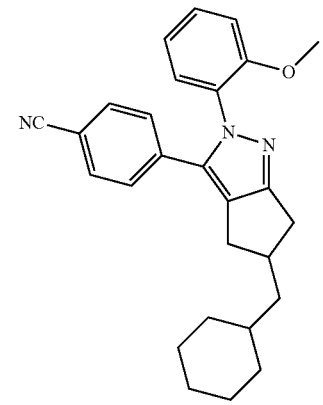

Cpd 106

A. To a suspension of anhydrous CeCl$_3$ (36 mg, 0.15 mmol, 0.5 eq) in THF (5 mL) at rt under Argon was added compound 23a (100 mg, 0.3 mmol, 1 eq) followed by cyclohexylmethylmagnesium bromide (23b) (1.82 mL of a 0.5 M solution in THF, 0.91 mmol, 3 eq). After stirring overnight, water and 1 N HCl were added, the reaction mixture was extracted with ether, and the organic phases were combined, dried over MgSO$_4$, filtered, and concentrated. Purification by chromatography (12 g), eluting with 30 to 60 to 100% EA/hexanes gave compound 23c (12 mg, 9%). ESI-MS (m/z): Calcd. for C27H29N3O2: 428.2 (M+1). found: 428.2.

B. To a solution of compound 23c (12 mg, 0.028 mmol, 1 eq) in THF (2 mL) at rt under Argon was added Burgess reagent (33 mg, 0.14 mmol, 5 eq). After 1 hr, water was added, extracted with DCM, the organics combined, dried over MgSO$_4$ and concentrated. Purification by chromatography (4 g), eluting with 15 to 30% EA/hexanes, gave compound 23d (3 mg, 26%, mix of isomers). ESI-MS (m/z): Calcd. for C27H27N3O: 410.2 (M+1). found: 410.2.

C. A solution of compound 23d (3 mg) and 10% Pd/C (5 mg) in methanol (5 mL) were placed under a hydrogen gas atmosphere overnight. The reaction was filtered through diatomaceous earth and concentrated. Purification by HPLC gave compound 106 (1.2 mg, 38%). $^1$H NMR (CHLOROFORM-d) δ: 7.51 (d, J=8.3 Hz, 2H), 7.42 (d, J=7.6 Hz, 1H), 7.33-7.39 (m, 1H), 7.24 (d, J=8.6 Hz, 2H), 7.04 (t, J=7.2 Hz, 1H), 6.88 (d, J=7.6 Hz, 1H), 3.46 (s, 3H), 2.91-3.13 (m, 3H), 2.43-2.55 (m, 2H), 1.64-1.83 (m, 4H), 1.48-1.56 (m, 3H), 1.13-1.32 (m, 4H), 0.80-1.00 (m, 2H). ESI-MS (m/z): Calcd. for C27H29N3O: 412.2 (M+1). found: 412.2.

Following the procedure described above for Example 23 and substituting the appropriate reagents, starting materials and purification methods known to those skilled in the art, the following compounds were prepared:

Cpd 104

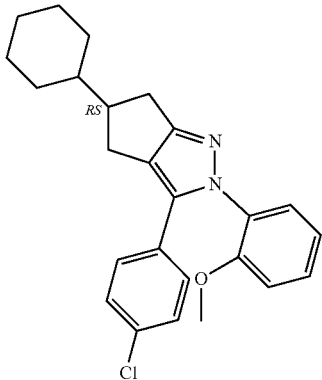

Cpd 104: $^1$H NMR (CHLOROFORM-d) δ: 7.38 (dd, J=7.7, 1.1 Hz, 1H), 7.33 (t, J=8.0 Hz, 1H), 7.16-7.22 (m, J=8.6 Hz, 2H), 7.05-7.11 (m, J=8.3 Hz, 2H), 6.97-7.04 (m, 1H), 6.88 (d, J=8.3 Hz, 1H), 3.49 (s, 3H), 2.83-2.97 (m, 2H), 2.48-2.73 (m, 3H), 1.74 (br. s., 5H), 1.44 (br. s., 1H), 1.15-1.35 (m, 3H), 0.78-1.12 (m, 2H). ESI-MS (m/z): Calcd. for C25H27ClN2O: 407.2 (M+1). found: 407.2.

Cpd 105

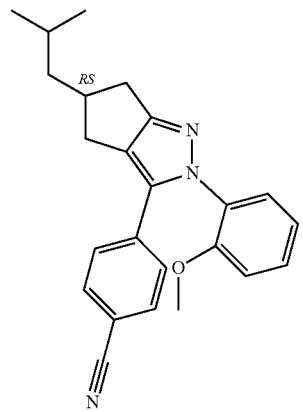

Cpd 105: $^1$H NMR (CHLOROFORM-d) δ: 7.51 (d, J=8.6 Hz, 2H), 7.42 (dd, J=7.7, 1.6 Hz, 1H), 7.33-7.39 (m, 1H), 7.24 (d, J=8.6 Hz, 2H), 7.00-7.08 (m, 1H), 6.85-6.91 (m, 1H), 3.46 (s, 3H), 2.91-3.10 (m, 3H), 2.42-2.58 (m, 2H), 1.66-1.78 (m, 1H), 1.47-1.56 (m, 2H), 0.96 (d, J=6.6 Hz, 6H). ESI-MS (m/z): Calcd. for C24H25N3O: 372.2 (M+1). found: 372.2.

The compounds of Table 1, exemplified hereinbelow, were prepared according to the schemes and specific examples described herein.

TABLE 1

Compounds of Formula (I)

Formula (I)

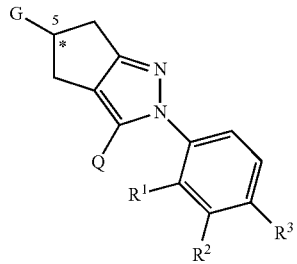

| Cpd No. | R$^1$ | R$^2$ | R$^3$ | Q | G | Configuration at C-5 |
|---|---|---|---|---|---|---|
| 1 | methoxy | H | H | 4-chlorophenyl | hydroxyethyl | RS |
| 2 | methoxy | H | H | 4-chlorophenyl | 2-(morpholin-4-ylcarbonyloxy)ethyl | RS |
| 3 | methoxy | H | H | 4-chlorophenyl | 2-(dimethylaminocarbonyloxy)ethyl | RS |
| 4 | methoxy | H | H | 4-chlorophenyl | prop-2-en-1-yl | RS |
| 5 | methoxy | H | H | 4-chlorophenyl | ethoxycarbonyl | RS |
| 6 | methoxy | H | H | 4-chlorophenyl | aminocarbonyl | RS |

TABLE 1-continued

Compounds of Formula (I)

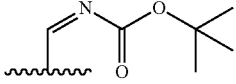 [SMILES: */C=N\C(=O)OC(C)(C)C]

Formula (I)

| Cpd No. | R¹ | R² | R³ | Q | G | Configuration at C-5 |
|---|---|---|---|---|---|---|
| 7 | methoxy | H | H | phenyl | methanesulfonyl-amino-methyl | RS |
| 8 | methoxy | H | H | 4-chloro-phenyl | methanesulfonyl-amino-methyl | RS |
| 9 | methoxy | H | H | phenyl | cyano | RS |
| 10 | methoxy | H | H | 4-chloro-phenyl | cyano | RS |
| 11 | methoxy | H | H | 4-chloro-phenyl | 2-(methanesulfonyl-amino)ethyl | RS |
| 12 | methoxy | H | H | 4-chloro-phenyl | 2-(methylcarbonyl-amino)ethyl | RS |
| 13 | methoxy | H | H | 4-chloro-phenyl | 2-(t-butoxycarbonyl-amino)ethyl | RS |
| 14 | ethyl | H | H | 4-chlorophenyl | ethoxycarbonyl | RS |
| 15 | ethyl | H | H | 4-chloro-phenyl | (see structure) | RS |
| 16 | ethyl | H | H | 4-chloro-phenyl | t-butoxycarbonyl-amino-methyl | RS |
| 17 | ethyl | H | H | 4-chloro-phenyl | diethylamino-carbonyloxy-methyl | RS |
| 18 | ethyl | H | H | 4-chloro-phenyl | methanesulfonyl-amino-methyl | RS |
| 19 | ethyl | H | H | 4-chloro-phenyl | trifluoromethyl-carbonylamino-methyl | RS |
| 20 | trifluoro-methyl | H | H | 4-chloro-phenyl | 2-(t-butoxycarbonyl-amino)ethyl | RS |
| 21 | trifluoro-methyl | H | H | 4-chloro-phenyl | 2-(methanesulfonyl-amino)ethyl | RS |
| 22 | trifluoro-methyl | H | H | 4-chloro-phenyl | 2-(dimethylamino-carbonylamino)ethyl | RS |
| 23 | trifluoro-methoxy | H | H | 4-chloro-phenyl | dimethylamino-carbonyloxy | RS |
| 24 | trifluoro-methoxy | H | H | 4-chloro-phenyl | morpholin-4-yl-carbonyloxy | RS |
| 25 | trifluoro-methoxy | H | H | 4-chloro-phenyl | hydroxy | RS |
| 26 | methoxy | H | H | 4-chloro-phenyl | hydroxy | RS |
| 27 | trifluoro-methoxy | H | H | 4-chloro-phenyl | oxo | N/A |
| 28 | methoxy | H | H | 4-chloro-phenyl | dimethylamino-carbonyloxy | RS |
| 29 | methoxy | H | H | 4-chloro-phenyl | morpholin-4-yl-carbonyloxy | RS |
| 30 | ethoxy | H | H | 4-chloro-phenyl | dimethylamino-carbonyloxy | RS |
| 31 | ethoxy | H | H | 4-chloro-phenyl | morpholin-4-yl-carbonyloxy | RS |
| 32 | methoxy | H | H | 4-chloro-phenyl | methanesulfonyl-amino | RS |

TABLE 1-continued

Compounds of Formula (I)

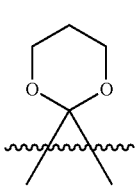

Formula (I)

| Cpd No. | $R^1$ | $R^2$ | $R^3$ | Q | G | Configuration at C-5 |
|---|---|---|---|---|---|---|
| 33 | methoxy | H | H | 4-chloro-phenyl | isopropylsulfonyl-amino | RS |
| 34 | methoxy | H | H | 4-chloro-phenyl | dimethylamino-carbonylamino | RS |
| 35 | methoxy | H | H | 4-chloro-phenyl | oxo | N/A |
| 36 | ethoxy | H | H | 4-chloro-phenyl | oxo | N/A |
| 37 | methoxy | H | H | 4-chloro-phenyl | methanesulfonyl-N-methyl-amino | RS |
| 38 | ethoxy | H | H | 4-chloro-phenyl | 2,5-dioxo-pyrrolidin-1-yl | RS |
| 39 | ethoxy | H | H | 4-chloro-phenyl | 1H-imidazol-1-yl | RS |
| 40 | ethoxy | H | H | 4-chloro-phenyl | 2-oxo-pyrrolidin-1-yl | RS |
| 41 | ethoxy | H | H | 4-chloro-phenyl | 4-(trimethylsilyl)-1H-1,2,3-triazol-1-yl | RS |
| 42 | ethoxy | H | H | 4-chloro-phenyl | 1H-1,2,3-triazol-1-yl | RS |
| 43 | ethoxy | H | H | 4-chloro-phenyl | 1H-imidazol-1-yl | R |
| 44 | ethoxy | H | H | 4-chloro-phenyl | isopropylsulfonyl-amino | R |
| 45 | ethoxy | H | H | 4-chloro-phenyl | trifluoromethyl-carbonylamino | R |
| 46 | ethoxy | H | H | 4-chloro-phenyl | dimethylamino-sulfonyl-N-methyl-amino | R |
| 47 | ethoxy | H | H | 4-chloro-phenyl | dimethylamino-sulfonylamino | RS |
| 48 | ethoxy | H | H | 4-chloro-phenyl | dimethylamino-sulfonyl-N-methyl-amino | RS |
| 49 | methoxy | H | H | 4-chloro-phenyl | methoxy | R |
| 50 | $R^2$ taken with $R^1$ and the phenyl ring to which $R^1$ and $R^2$ are both attached to form 2,3-dihydro-1-benzofuran-7-yl | | H | 4-chloro-phenyl | dimethylamino-sulfonyl-N-methyl-amino | S |
| 51 | $R^2$ taken with $R^1$ and the phenyl ring to which $R^1$ and $R^2$ are both attached to form 2,3-dihydro-1-benzofuran-7-yl | | H | 4-chloro-phenyl | isopropylsulfonyl-N-methyl-amino | S |
| 52 | methoxy | H | chloro | 4-chloro-phenyl | | spiro fused |

TABLE 1-continued

Compounds of Formula (I)

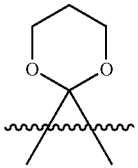

Formula (I)

| Cpd No. | R¹ | R² | R³ | Q | G | Configuration at C-5 |
|---|---|---|---|---|---|---|
| 53 | methoxy | H | H | 4-chloro-phenyl | =N(OH) | N/A |
| 54 | methoxy | H | H | 4-chloro-phenyl | 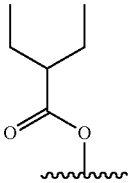 [SMILES: *OC(=O)C(CC)CC] | spiro fused |
| 55 | methoxy | H | H | 4-chloro-phenyl |  | R |
| 56 | methoxy | H | H | 6-methoxy-pyridin-3-yl | dimethylamino-sulfonyl-N-methyl-amino | R |
| 57 | methoxy | H | H | 6-isopropyl-oxy pyridin-3-yl | dimethylamino-sulfonyl-N-methyl-amino | R |
| 58 | methoxy | H | H | 4-chloro-phenyl | phenyloxy | S |
| 59 | methoxy | H | H | 4-chloro-phenyl | pyridin-3-yloxy | S |
| 60 | methoxy | H | H | 4-chloro-phenyl | 6-isopropyloxy-pyridin-3-yl | RS |
| 61 | methoxy | H | H | 4-chloro-phenyl | pyridin-2-yloxy | R |
| 62 | methoxy | H | H | 4-chloro-phenyl | 6-(morpholin-4-yl)pyridin-3-yl | RS |
| 63 | methoxy | H | H | 4-chloro-phenyl | pyridin-3-yl | RS |
| 64 | methoxy | H | H | 4-chloro-phenyl | 4,4-dimethyl-cyclohexyl | RS |
| 65 | methoxy | H | H | 4-chloro-phenyl | (3-RS)-1,2,3,4-tetrahydroquinolin-3-yl | RS |
| 66 | methoxy | H | H | 4-chloro-phenyl | 5-(ethoxycarbonyl)pyridin-3-yl | RS |
| 67 | methoxy | H | H | 4-chloro-phenyl | isopropyloxy | S |
| 68 | methoxy | H | H | 4-chloro-phenyl | morpholin-4-yl | RS |
| 69 | methoxy | H | H | 4-chloro-phenyl | trimethylsilyloxy | S |

TABLE 1-continued

Compounds of Formula (I)

Formula (I)

| Cpd No. | R¹ | R² | R³ | Q | G | Configuration at C-5 |
|---|---|---|---|---|---|---|
| 70 | methoxy | H | H | 4-chloro-phenyl | | S |
| 71 | methoxy | H | H | 4-chloro-phenyl | | spiro fused |
| 72 | methoxy | H | H | 4-chloro-phenyl | 2-ethylbutoxy | S |
| 73 | methoxy | H | H | 4-chloro-phenyl | 6-methyl-pyridin-3-yl | RS |
| 74 | methoxy | H | H | 4-chloro-phenyl | 6-ethoxy-pyridin-3-yl | RS |
| 75 | methoxy | H | H | 4-chloro-phenyl | 2-chloro-6-isopropyl-pyridin-3-yl | RS |
| 76 | methoxy | H | H | 4-chloro-phenyl | tetrahydro-2H-pyran-2-yloxy | S |
| 77 | methoxy | H | H | 4-chloro-phenyl | 6-(cyclopropyl)pyridin-3-yl | RS |
| 78 | methoxy | H | H | 4-chloro-phenyl | cyclohexyl-carbonyloxy | S |
| 79 | methoxy | H | H | 4-chloro-phenyl | cyclopentyl-carbonyloxy | S |
| 80 | methoxy | H | H | 4-chloro-phenyl | cyclobutyl-carbonyloxy | S |
| 81 | methoxy | H | H | 4-chloro-phenyl | isopropyl-carbonyloxy | S |
| 82 | methoxy | H | H | 4-chloro-phenyl | cyclohexyl-methyloxy | S |
| 83 | methoxy | H | H | 4-chloro-phenyl | cyclopentyl-methyloxy | S |
| 84 | methoxy | H | H | 4-chloro-phenyl | cyclobutyl-methyloxy | S |
| 85 | methoxy | H | H | 4-chloro-phenyl | 2-methylpropyloxy | S |
| 86 | methoxy | H | H | 4-chloro-phenyl | tetrahydro-2H-pyran-4-ylcarbonyloxy | S |
| 87 | methoxy | H | H | 4-chloro-phenyl | tetrahydro-2H-pyran-4-yl-methyloxy | S |
| 88 | methoxy | H | H | 4-chloro-phenyl | cyclohexyloxy | S |
| 89 | methoxy | H | H | 4-chloro-phenyl | (1S,2S,4R)-bicyclo[2.2.1]hept-2-yloxy | S |

TABLE 1-continued

Compounds of Formula (I)

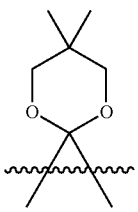

Formula (I)

| Cpd No. | R¹ | R² | R³ | Q | G | Configuration at C-5 |
|---|---|---|---|---|---|---|
| 90 | methoxy | H | H | 4-chloro-phenyl | cyclopentyloxy | S |
| 91 | methoxy | H | H | 4-cyano phenyl | 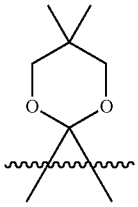 | spiro fused |
| 92 | methoxy | H | H | 4-chloro-phenyl | isopropyl | RS |
| 93 | methoxy | H | H | 4-dimethyl-amino-phenyl | 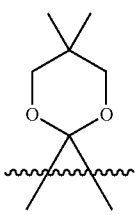 | spiro fused |
| 94 | methoxy | H | H | 6-ethoxy-pyridin-3-yl | 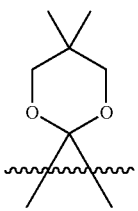 | spiro fused |
| 95 | methoxy | H | H | 6-methyl-pyridin-3-yl | 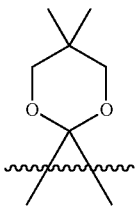 | spiro fused |
| 96 | methoxy | H | H | 6-methoxy-pyridin-3-yl | 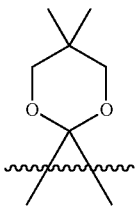 | spiro fused |

TABLE 1-continued

Compounds of Formula (I)

Formula (I)

| Cpd No. | R¹ | R² | R³ | Q | G | Configuration at C-5 |
|---|---|---|---|---|---|---|
| 97 | methoxy | H | H | 6-dimethyl-amino-pyridin-3-yl | | spiro fused |
| 98 | methoxy | H | H | 4-chloro-phenyl | R,R | spiro fused |
| 99 | methoxy | H | H | 4-chloro-phenyl | S,S | spiro fused |
| 100 | methoxy | H | H | 4-chloro-phenyl | R,R | spiro fused |
| 101 | methoxy | H | H | 4-chloro-phenyl | S,S | spiro fused |
| 102 | methoxy | H | H | 4-chloro-phenyl | R,S,R | spiro fused |

TABLE 1-continued

Compounds of Formula (I)

Formula (I)

| Cpd No. | R¹ | R² | R³ | Q | G | Configuration at C-5 |
|---|---|---|---|---|---|---|
| 103 | methoxy | H | H | 4-chlorophenyl | (R,S,S-dioxolane spiro) | spiro fused |
| 104 | methoxy | H | H | 4-chlorophenyl | cyclohexyl | RS |
| 105 | methoxy | H | H | 4-cyanophenyl | 2-methylpropyl | RS |
| 106 | methoxy | H | H | 4-cyanophenyl | cyclohexylmethyl | RS |
| 107 | methoxy | H | H | 4-dimethylaminophenyl | (dioxolane spiro) | spiro fused |
| 108 | methoxy | H | H | 6-ethoxypyridin-3-yl | (dioxolane spiro) | spiro fused |
| 109 | methoxy | H | H | 6-methylpyridin-3-yl | (dioxolane spiro) | spiro fused |
| 110 | methoxy | H | H | 6-dimethylaminopyridin-3-yl | (dioxolane spiro) | spiro fused |

TABLE 1-continued

Compounds of Formula (I)

Formula (I)

| Cpd No. | R¹ | R² | R³ | Q | G | Configuration at C-5 |
|---|---|---|---|---|---|---|
| 111 | methoxy | H | H | 4-cyano-phenyl | | spiro fused |
| 112 | methoxy | H | H | 4-chloro-phenyl | | spiro fused |
| 113 | methoxy | H | H | 4-chloro-phenyl | | spiro fused |
| 114 | methoxy | H | H | 4-chloro-phenyl | | spiro fused |
| 115 | methoxy | H | H | 4-chloro-phenyl | | spiro fused |
| 116 | methoxy | H | H | 4-chloro-phenyl | 2,6-dimethyl-morpholin-4-yl | RS |
| 117 | methoxy | H | H | 4-chloro-phenyl | 4-methyl-piperidin-1-yl | RS |
| 118 | methoxy | H | H | 4-chloro-phenyl | 3,3-diethyl-pyrrolidin-1-yl | RS |
| 119 | methoxy | H | H | 4-chloro-phenyl | 3,3-dimethyl-pyrrolidin-1-yl | RS |
| 120 | methoxy | H | H | 5-chloro-thien-2-yl | | spiro fused |

TABLE 1-continued

Compounds of Formula (I)

Formula (I)

| Cpd No. | R¹ | R² | R³ | Q | G | Configuration at C-5 |
|---|---|---|---|---|---|---|
| 121 | methoxy | H | H | 5-chloro-thien-2-yl | | spiro fused |
| 122 | methoxy | H | H | 4-chloro-phenyl | pyrrolidin-1-yl | RS |
| 123 | methoxy | H | H | 4-chloro-phenyl | 3,3-difluoro-pyrrolidin-1-yl | RS |
| 124 | methoxy | H | H | 4-cyano-phenyl | 4-cyclopentyl-1H-1,2,3-triazol-1-yl | S |
| 125 | methoxy | H | H | 4-cyano-phenyl | 4-methoxycarbonyl-1H-1,2,3-triazol-1-yl | S |
| 126 | methoxy | H | H | 4-cyano-phenyl | 4-(1-hydroxy-1-methylethyl)-1H-1,2,3-triazol-1-yl | S |
| 127 | methoxy | H | H | 4-cyano-phenyl | 4-(2-methyl-propyl)-1H-1,2,3-triazol-1-yl | S |
| 128 | methoxy | H | H | 4-cyano-phenyl | 4-(methylcarbonyloxy-methyl)-1H-1,2,3-triazol-1-yl | S |
| 129 | methoxy | H | H | 4-cyano-phenyl | 4-(methoxymethyl)-1H-1,2,3-triazol-1-yl | S |
| 130 | methoxy | H | H | 4-cyano-phenyl | 4-t-butyl-1H-1,2,3-triazol-1-yl | S |
| 131 | methoxy | H | H | 4-cyano-phenyl | 4,5-dimethyl-1H-imidazol-1-yl | S |
| 132 | methoxy | H | H | 4-cyano-phenyl | 2,4,5-trimethyl-1H-imidazol-1-yl | S |
| 133 | methoxy | H | H | 4-cyano-phenyl | 2-ethyl-4,5-dimethyl-1H-imidazol-1-yl | S |
| 134 | methoxy | H | H | 4-cyano-phenyl | 2-ethyl-1H-imidazol-1-yl | S |
| 135 | methoxy | H | H | 4-cyano-phenyl | 2-methyl-1H-imidazol-1-yl | S |
| 136 | methoxy | H | H | 4-cyano-phenyl | 4,5-diethyl-1H-1,2,3-triazol-1-yl | S |
| 137 | methoxy | H | H | 4-cyano-phenyl | 2,4,5-triethyl-1H-imidazol-1-yl | S |
| 138 | methoxy | H | H | 4-cyano-phenyl | 2-methyl-4,5-diethyl-1H-imidazol-1-yl | S |
| 139 | methoxy | H | H | 4-cyano-phenyl | 4,5-diethyl-1H-imidazol-1-yl | S |

BIOLOGICAL EXAMPLES

In Vitro Assays

Example 1

Functional Assay: Antagonism of N-Type Calcium Channel

A stable cell line (HEK parent) co-expressing the $\alpha_{1B}$ (Cav2.2), $\beta_3$ and $\alpha_2\delta$ subunits of the N-type calcium channel subunits was used. These cells were routinely grown as monolayers in low glucose-containing Dulbecco's Modified Eagle Medium supplemented with 10% FBS, 2 mM L-glutamine, 100 I.U./mL penicillin, 100 μg/mL streptomycin, 400 μg/mL G418 and 200 μg/mL Zeocin (split ratio=1:5). Cells were maintained in 5% $CO_2$ at 37° C. Compounds of Formula (I) were prepared as 10 mM stocks in DMSO from neat compound, if available. Otherwise, the 5 or 10 mM DMSO stock solutions provided in-house were used.

Calcium mobilization responses to KCl depolarization were evaluated by measuring the intensity of calcium-mediated fluorescent signal in the presence of BD Calcium Assay Dye (BD Biosciences, Franklin Lakes, N.J., U.S.A.), utilizing a Functional Drug Screening System (FDSS) by Hamamatsu Corporation (Bridgewater, N.J. U.S.A.).

Twenty-four hr prior to assay, cells were seeded in clear-base poly-D-lysine-coated 384-well plates (BD Biosciences) at a density of 5,000 cells per well in culture medium and grown overnight in 5% $CO_2$ at 37° C. On the day of assay, growth media were removed, and cells were loaded with BD calcium assay dye (BD Biosciences) for 35 min at 37° C. under 5% $CO_2$ and then for 25 min at room temp. Utilizing the FDSS, cells were exposed to representative compounds of Formula (I) at varying concentrations, and intracellular calcium was measured for 5 min prior to the addition of 50 mM KCl for an additional 3 min of measurement.

Calculations and Formulas $IC_{50}$ values for representative compounds of Formula (I) were determined from six-point concentration-response experiments and represent the concentration of said compound required to inhibit 50% of the maximal response. Maximal fluorescence intensity (FI) achieved upon addition of 50 mM KCl was exported from the FDSS software and further analyzed using GraphPad Prism 3.02 (Graph Pad Software Inc., San Diego, Calif., U.S.A.). Data were normalized to the maximum average counts from quadruplicate wells for each condition in the presence of 50 mM KCl and to the minimum average counts in the presence of buffer. Theoretical curves were generated using nonlinear regression curve-fitting analysis of either sigmoidal concentration-response or sigmoidal concentration-response (variable slope), and the $IC_{50}$ values with the best-fit curve determined by GraphPad Prism were reported. Resultant data are shown in Table 2.

TABLE 2

| Compound No | FDSS $IC_{50}$ (μM) | % Inhibition (%) at 0.33 μM | % Inhibition (%) at 1 μM |
|---|---|---|---|
| 1 | 0.20 | | |
| 2 | 0.033 | | |
| 3 | 0.026 | | |
| 4 | | | 81 |
| 5 | 0.043 | | |
| 6 | 0.49 | 75 | |
| 7 | | 68 | |
| 8 | 0.055 | 96 | |
| 9 | | 59 | |
| 10 | 0.30 | 83 | |
| 11 | 0.073 | 99 | |
| 12 | 0.070 | | |
| 13 | 0.038 | | |
| 14 | 0.090 | | |
| 15 | 0.30 | | |
| 16 | 0.13 | | |
| 17 | 0.18 | | |
| 18 | 0.20 | | |
| 19 | 0.13 | | |
| 20 | 0.26 | | |
| 21 | | | 65 |
| 22 | 0.22 | | |
| 23 | 0.14 | | |
| 24 | 0.15 | | |
| 25 | | | 61 |
| 26 | | | 62 |
| 27 | 0.011 | | |
| 28 | 0.015 | | |
| 29 | 0.043 | | |
| 30 | 0.028 | | |
| 31 | 0.018 | | |
| 32 | 0.026 | | |
| 33 | 0.018 | | |
| 34 | 0.014 | | |
| 35 | 0.059 | | |
| 36 | 0.029 | | |
| 37 | 0.0064 | | |
| 38 | 0.0075 | | |
| 39 | 0.038 | 81 | |
| 40 | 0.019 | | |
| 41 | 0.024 | 92 | |
| 42 | 0.019 | 91 | |
| 43 | 0.042 | 87 | |
| 44 | 0.032 | 89 | |
| 45 | 0.0040 | 94 | |
| 46 | 0.0026 | 99 | |
| 47 | 0.0040 | 92 | |
| 48 | 0.0012 | 97 | |
| 49 | 0.052 | 76 | |
| 50 | 0.014 | 95 | |
| 51 | 0.034 | 94 | |
| 52 | 0.13 | 64 | |
| 53 | | 31 | |
| 54 | 0.050 | 86 | |
| 55 | 0.011 | 95 | |
| 56 | 0.013 | 93 | |
| 57 | 0.018 | 99 | |
| 58 | 0.13 | 65 | |
| 59 | 0.094 | 76 | |
| 60 | 0.28 | 62 | |
| 61 | 0.098 | 77 | |
| 62 | | 42 | |
| 63 | 0.0086 | 98 | |
| 64 | 0.28 | 66 | |
| 65 | 0.28 | 59 | |
| 66 | 0.066 | 79 | |
| 67 | 0.0057 | 100 | |
| 68 | 0.016 | 95 | |
| 69 | 0.0096 | 93 | |
| 70 | 0.015 | 96 | |
| 71 | 0.013 | 89 | |
| 72 | 0.061 | 78 | |
| 73 | 0.086 | 81 | |
| 74 | 0.15 | 61 | |
| 75 | 0.23 | 53 | |
| 76 | 0.028 | 92 | |
| 77 | 0.062 | 81 | |
| 78 | 0.093 | 78 | |
| 79 | 0.075 | 82 | |
| 80 | 0.031 | 89 | |
| 81 | 0.048 | 86 | |
| 82 | 0.13 | 76 | |

TABLE 2-continued

| Compound No | FDSS IC$_{50}$ (µM) | % Inhibition (%) at 0.33 µM | % Inhibition (%) at 1 µM |
|---|---|---|---|
| 83 | 0.049 | 92 | |
| 84 | 0.06 | 80 | |
| 85 | 0.023 | 94 | |
| 86 | 0.082 | 82 | |
| 87 | 0.092 | 82 | |
| 88 | 0.043 | 83 | |
| 89 | 0.049 | 85 | |
| 90 | 0.022 | 89 | |
| 91 | 0.019 | 89 | |
| 92 | | 43 | |
| 93 | 0.012 | 91 | |
| 94 | 0.060 | 81 | |
| 95 | 0.11 | 67 | |
| 96 | 0.034 | 81 | |
| 97 | 0.029 | 88 | |
| 98 | 0.0059 | 102 | |
| 99 | 0.013 | 93 | |
| 100 | 0.0044 | 101 | |
| 101 | 0.027 | 98 | |
| 102 | 0.0076 | 97 | |
| 103 | 0.0048 | 101 | |
| 104 | 0.14 | 61 | |
| 105 | 0.046 | 81 | |
| 106 | 0.27 | 64 | |
| 107 | 0.0030 | 92 | |
| 108 | 0.010 | 86 | |
| 109 | 0.019 | 84 | |
| 110 | 0.0028 | 90 | |
| 111 | 0.0037 | 90 | |
| 112 | 0.018 | 90 | |
| 113 | 0.042 | 82 | |
| 114 | 0.0050 | 90 | |
| 115 | 0.011 | 85 | |
| 116 | 0.048 | 77 | |
| 117 | 0.044 | 75 | |
| 118 | 0.046 | 76 | |
| 119 | 0.084 | 76 | |
| 120 | 0.091 | 78 | |
| 121 | 0.030 | 86 | |
| 122 | | 33 | |
| 123 | 0.019 | 91 | |
| 124 | 0.043 | 88 | |
| 125 | 0.081 | 70 | |
| 126 | | 33 | |
| 127 | 0.017 | 97 | |
| 128 | 0.17 | 59 | |
| 129 | | 47 | |
| 130 | 0.050 | 92 | |
| 131 | 0.1045 | 67 | |
| 132 | | 29 | |
| 133 | | 35 | |
| 134 | 0.20 | 50 | |
| 135 | | 44 | |
| 136 | 0.016 | 89 | |
| 137 | | 49 | |
| 138 | 0.32 | 63 | |
| 139 | 0.037 | 87 | |

Example 2

Automated Electrophysiology Assay

Cells were grown in T175 flasks to 50%-90% confluence. At the time of use, cells were enzymatically treated with Detachin (Genlantis, San Diego, Calif. USA), centrifuged, rinsed, and resuspended in 293 SFM II media (Life Technologies, Grand Island, N.Y. U.S.A.) supplemented with 25 mM HEPES (Sigma-Aldrich, St. Louis, Mo. U.S.A.) to a concentration of 2-3×10$^6$ cells/mL. Cells were added to the automated cell preparation station on the QPatch-HT (Sophion Biosciences, North Brunswick, N.J. U.S.A.), and following a 10- to 30-min recovery period with gentle stirring, the assay protocol was initiated. During the automated cell preparation, cells were collected, centrifuged and resuspended in an extracellular (EC) solution containing 132 mM NaCl, 1.8 mM CaCl$_2$, 5.4 mM KCl, 0.8 mM MgCl$_2$, 10 mM glucose, and 10 mM HEPES (pH=7.4), adjusted with sucrose to approximately 315 mOsm. The QPlate was primed with an intracellular solution containing 135 mM CsCl, 10 mM EGTA, 4 MgATP, 0.3 NaGTP, and 20 mM HEPES (pH=7.2), adjusted to approximately 290 mOsm with deionized water and the EC solution. Cells were added to the prepared QPlate wells by robotic pipettes of the QPatch-HT.

For cells determined to be in stable whole-cell patch clamp, the EC solution was replaced with a barium (Ba)/triethylammonium (TEA) solution containing 140 mM TEA-Cl, 10 mM BaCl$_2$, 0.8 mM MgCl$_2$, 10 mM glucose and 10 mM HEPES (pH=7.4). High (40 mM) BaCl$_2$ concentrations were made with adjustments to TEA-Cl (90 mM) to maintain the osmolarity. From a resting potential of −80 mV, a train of depolarizing pulses (15 pulses at 5 Hz, +20 mV) was delivered to the cell once every 30 sec for eight trains (4 min total), and the resulting currents were measured during a control period (no compound). This protocol was repeated for each subsequent addition of control buffer with or without compound (three periods total, each with four trains). The current generated in the 1$^{st}$ and 15$^{th}$ pulses of the last train of each period in the presence of each drug concentration was normalized to the current generated during the control period at the respective pulses (representing low- and high-frequency stimulation, respectively). Data from both the second and third drug application periods were analyzed for each cell. A final addition of Ba/TEA solution containing 60-100 µM CdCl$_2$ was made to block all N-type current and to "zero" the currents for each cell. All buffer/compound additions were made using a "spitting" feature of the QPatch-HT, which added three repetitions of 5 µL solution at the beginning of each recording period.

To examine closed-state inactivation, cells were subjected to a channel-activating 50-msec depolarizing step pulse from −80 to +10 mV, followed by a 5-sec nonactivating step to voltages ranging from −130 to −60 mV in 10 mV increments and then a 50-ms step from −80 to +10 mV to assess the remaining current. Currents from the activating voltage pulse were normalized to the peak value of the test pulse following the −130 mV step and fit to a Boltzman equation to obtain the $V_{1/2}$. Roscovitine (Sigma-Aldrich) was prepared as a 100 mM stock in dimethyl sulfoxide and diluted to the indicated working concentrations. Tetrandrine (Sigma-Aldrich) was prepared as a 4 mM stock in acidic water (pH=2.0) and then diluted to working concentrations in the external solution. ω-Conotoxin MVIIA (Sigma-Aldrich) was prepared as a 0.3 mg/mL stock solution in water, with 0.1% bovine serum albumin V (Life Technologies). Compounds of Formula (I) were diluted first into dimethyl sulfoxide and then into 10% pluronic F-127 in water (Life Technologies), sonicated for 1 min and diluted into EC buffer. Vehicle controls were run in parallel in all experiments.

Unless otherwise indicated, statistics for comparing among electrophysiological results utilized a one-way analysis of variance with Fisher's least squares determination test for pair-wise comparison. Resultant data are shown in Tables 3 and 4, below.

TABLE 3

QPatch at Low Frequency

| Cpd No. | 0.01 | 0.03 | 0.1 | 0.25 | 1 | 5 |
| --- | --- | --- | --- | --- | --- | --- |
| 2 | | | | 54 | 76 | 90 |
| 3 | | | | 35 | 69 | 93 |
| 5 | | | | | | 82 |
| 8 | | | −9 | | 62 | |
| 11 | | | | | 29 | |
| 12 | | | | | 15 | |
| 13 | | | | | 42 | |
| 16 | | | | | 19 | |
| 27 | | | −16 | | | |
| 28 | | | 25 | | | |
| 29 | | | −8 | | | |
| 30 | | | 9 | | | |
| 31 | | | 14 | | | |
| 32 | | | 18 | | | |
| 33 | | | 35 | | | |
| 34 | | | 34 | | | |
| 36 | | | 18 | | | |
| 37 | | | 44 | | | |
| 38 | | | 47 | | | |
| 39 | | | 13 | 34 | 51 | |
| 41 | | | 58 | | | |
| 42 | | | | | 86 | |
| 43 | | | −22 | | | |
| 44 | | | 42 | | | |
| 45 | | | 60 | | | |
| 46 | | | 21 | | | |
| 47 | | | 15 | | | |
| 48 | | | 52 | | | |
| 50 | | | 33 | | | |
| 51 | | | | | 49 | |
| 54 | | | | | 55 | |
| 55 | | 15 | 12 | | 57 | |
| 56 | | | −1 | | 32 | |
| 57 | | | | | 75 | |
| 63 | | | | | 40 | |
| 67 | | | 48 | | | |
| 68 | | | 33 | | | |
| 69 | | | 15 | | | |
| 71 | | | 21 | | | |
| 76 | | | 27 | | | |
| 78 | | | 15 | | | |
| 79 | | | −7 | | | |
| 80 | | | 7 | | 6 | |
| 81 | | | −4 | | | |
| 85 | | | −5 | | | |
| 88 | | | 22 | | | |
| 89 | | | 6 | | | |
| 90 | | | 10 | | | |
| 91 | 19 | | 28 | | 40 | |
| 93 | | | 12 | | | |
| 96 | | | −1 | | | |
| 97 | | | 27 | | | |
| 98 | | | −6 | | | |
| 99 | | | −4 | | | |
| 100 | 10 | | 46 | | 72 | |
| 101 | | | 3 | | | |
| 102 | | | | | 42 | |
| 103 | −21 | | 12 | | 36 | |
| 105 | | | −1 | | 10 | |
| 107 | | | 34 | | | |
| 108 | | | 3 | | | |
| 109 | | | 8 | | | |
| 110 | | | −9 | | | |
| 111 | | | −5 | | | |
| 112 | | | 7 | | | |
| 113 | | | −4 | | | |
| 114 | | | 44 | | | |
| 115 | | | 8 | | | |
| 123 | | | 2 | | | |
| 124 | | | | | 68 | |
| 127 | | | 13 | | | |
| 130 | | | | | 39 | |
| 139 | | | | | 72 | |

TABLE 4

QPatch at High Frequency

| Cpd No. | 0.01 | 0.03 | 0.1 | 0.25 | 1 | 5 |
| --- | --- | --- | --- | --- | --- | --- |
| 2 | | | | 58 | 69 | 97 |
| 3 | | | | 57 | 76 | 88 |
| 5 | | | | | | 85 |
| 8 | | | −12 | | 57 | |
| 11 | | | | | 28 | |
| 12 | | | | | 26 | |
| 13 | | | | | 67 | |
| 16 | | | | | 43 | |
| 27 | | | −14 | | | |
| 28 | | | 45 | | | |
| 29 | | | 21 | | | |
| 30 | | | 25 | | | |
| 31 | | | 22 | | | |
| 32 | | | 20 | | | |
| 33 | | | 42 | | | |
| 34 | | | 37 | | | |
| 36 | | | 26 | | | |
| 37 | | | 46 | | | |
| 38 | | | 53 | | | |
| 39 | | | 29 | 47 | 72 | |
| 41 | | | 60 | | | |
| 42 | | | | | 87 | |
| 43 | | | 5 | | | |
| 44 | | | 48 | | | |
| 45 | | | 68 | | | |
| 46 | | | 50 | | | |
| 47 | | | 19 | | | |
| 48 | | | 63 | | | |
| 50 | | | 41 | | | |
| 51 | | | | | 66 | |
| 54 | | | | | 67 | |
| 55 | | 19 | 29 | | 79 | |
| 56 | | | 2 | | 47 | |
| 57 | | | | | 83 | |
| 63 | | | | | 62 | |
| 67 | | | 61 | | | |
| 68 | | | 31 | | | |
| 69 | | | 26 | | | |
| 70 | | | 19 | | | |
| 71 | | | 37 | | | |
| 76 | | | 42 | | | |
| 78 | | | 27 | | | |
| 79 | | | 11 | | | |
| 80 | | | 22 | | 43 | |
| 81 | | | 12 | | | |
| 85 | | | 2 | | | |
| 88 | | | 33 | | | |
| 89 | | | 26 | | | |
| 90 | | | 21 | | | |
| 91 | 20 | | 39 | | 61 | |
| 93 | | | 30 | | | |
| 96 | | | 20 | | | |
| 97 | | | 33 | | | |
| 98 | | | 28 | | | |
| 99 | | | 34 | | | |
| 100 | 21 | | 69 | | 83 | |
| 101 | | | 40 | | | |
| 102 | | | | | 58 | |
| 103 | | | 46 | | 69 | |
| 105 | | | 20 | | 40 | |
| 107 | | | 33 | | | |
| 108 | | | 13 | | | |
| 109 | | | 9 | | | |
| 110 | | | 1 | | | |
| 111 | | | 21 | | | |
| 112 | | | 26 | | | |
| 113 | | | 3 | | | |
| 114 | | | 65 | | | |
| 115 | | | 37 | | | |
| 123 | | | 26 | | | |
| 124 | | | | | 73 | |
| 127 | | | 26 | | | |

TABLE 4-continued

QPatch at High Frequency

| | % Inhibition at Various Concentrations (μM) | | | | | |
|---|---|---|---|---|---|---|
| Cpd No. | 0.01 | 0.03 | 0.1 | 0.25 | 1 | 5 |
| 130 | | | | | 57 | |
| 139 | | | | | 66 | |

In Vivo Assays

Example 3

Complete Freund's Adjuvant (CFA)-Induced Hyperalgesia

The intraplantar injection of complete Freund's adjuvant (CFA) in rodents results in a long-lasting inflammatory reaction, characterized by a pronounced hypersensitivity to both thermal and mechanical stimuli, which peaks between 24-72 hr following injection and can last for several weeks. This test predicts the analgesic, anti-allodynic and/or antihyperalgesic effect of numerous efficacious clinical agents, including acetaminophen, NSAIDS, such as aspirin and ibuprofen, opioids, such as morphine, and especially the N-type calcium channel blocker ziconotide, which is marketed as Prialt® for the management of severe chronic pain, including several types of neuropathic pain.

To assess whether test compounds of Formula (I) reverse established hypersensitivity, a 100 μL of CFA (suspended in a 1:1 emulsion of saline and heat-killed *Mycobacterium tuberculosis* in mineral oil) was injected into a single hind paw of Sprague-Dawley rats (typically males ranging from 150-350 g).

Each rat was placed in a test chamber on a warm glass surface and allowed to acclimate for approximately 10 min. A radiant thermal stimulus (beam of light) was then focused through the glass onto the plantar surface of each hind paw in turn. The thermal stimulus was automatically shut off by a photoelectric relay when the paw was moved or when the cut-off time was reached (20 sec for radiant heat at ~5 Amps). An initial (baseline) response latency to the thermal stimulus was recorded for each animal prior to the injection of CFA. Twenty-four hr following intraplantar CFA injection, the response latency of the animal to the thermal stimulus was then re-evaluated and compared to the animal's baseline response time. Only rats that exhibited at least a 25% reduction in response latency (i.e., hyperalgesia) were included in further analysis. Immediately following the post-CFA latency assessment, test compound or vehicle (usually Solutol, hydroxypropyl methylcellulose, hydroxypropyl beta-cyclodextrin or PEG-400) was administered i.p. or p.o. to rats. Post-compound treatment withdrawal latencies were assessed at fixed time intervals, typically 30, 60 and 120 min. Resultant data for Compound 71 of Formula (I) is shown in FIG. 1.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

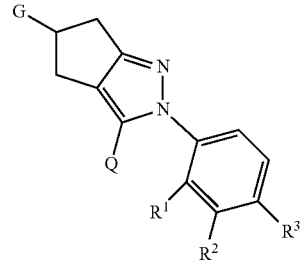

Formula (I)

wherein
$R^1$ is selected from the group consisting of $C_{1-4}$alkyl, $C_{1-4}$alkoxy, trifluoromethoxy, and trifluoromethyl;
$R^2$ is hydrogen; or, $R^2$ may be taken with $R^1$ and the phenyl ring to which $R^1$ and $R^2$ are both attached to form 2,3-dihydrobenzofuran-7-yl;
$R^3$ is hydrogen, chloro, or fluoro;
Q is selected from the group consisting of Q1, Q2, and Q3;

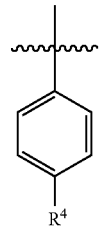

Q1

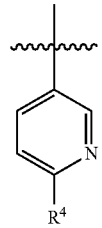

Q2

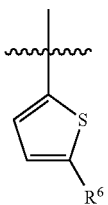

Q3 wherein
$R^4$ is selected from the group consisting of hydrogen, $C_{1-4}$alkyl, $C_{1-4}$alkoxy, cyano, fluoro, chloro, hydroxy, di($C_{1-4}$alkyl)amino, ($C_{1-4}$alkyl)amino, amino, $C_{1-4}$alkylcarbonyl, and $C_{1-4}$alkylsulfonyl;
$R^5$ and $R^6$ are each independently selected from the group consisting of hydrogen, $C_{1-4}$alkyl, $C_{1-4}$alkoxy, cyano, chloro, and di($C_{1-4}$alkyl)amino;
G is selected from the group consisting of $C_{1-6}$alkyl, hydroxy($C_{1-4}$)alkyl, $C_{1-6}$alkoxy, hydroxy, allyl, 2-methylprop-1-enyl, cyano, oxime, phenoxy, $C_{1-4}$alkoxycarbonyl, $C_{3-6}$cycloalkyl, 4,4-dimethyl-cyclohexyl, $C_{3-6}$cycloalkyl($C_{1-4}$)alkyl, $C_{3-6}$cycloalkyloxy, $C_{1-6}$alkylcarbonyloxy, di($C_{1-4}$alkyl)aminocarbonyloxy, di($C_{1-4}$alkyl)aminocarbonyloxy-$C_{1-4}$alkyl, $C_{1-4}$alkoxycarbonylamino-$C_{1-4}$alkyl, $C_{3-6}$cycloalkyl($C_{1-4}$)alkoxy, $C_{3-6}$cycloalkylcarbonyloxy, di($C_{1-4}$alkyl)aminosulfonyl-amino, di($C_{1-4}$alkyl)aminosulfonyl-(N-methyl)amino, $C_{1-4}$alkylsulfonyl-(N-methyl)amino, $C_{1-4}$alkylsulfonylamino, $C_{1-4}$alkylsulfonylamino-$C_{1-4}$alkyl, $C_{1-4}$alkylcarbonylamino-$C_{1-4}$alkyl, di($C_{1-4}$alkyl)aminocarbonylamino-$C_{1-4}$alkyl, trifluoromethylcarbonylamino, trifluoromethylcarbonylamino-$C_{1-4}$alkyl, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-$C_{1-4}$alkyl, 6-(morpholin-4-yl)-pyrimidin-3-yl, 4-methyl-piperidin-1-yl, (1,2,4)-bicyclo[2.2.1]heptan-2-yloxy, tetrahydro-2H-pyran-4-ylcarbonyloxy, tetrahydro-2H-pyran-4-yl($C_{1-4}$alkoxy, 1,2,3,4-tetrahydroquinolin-3-yl, aminocarbonyl, pyridin-3-yl optionally substituted with one to two substituents each independently selected from the group consisting of $C_{1-4}$alkyl, $C_{1-4}$alkoxy, chloro, cyclopropyl, morpholin-4-yl, and $C_{1-4}$alkoxycarbonyl;

1H-1,2,3-triazol-1-yl optionally substituted with one to two substituents each independently selected from the group consisting of $C_{1-4}$alkyl, 2-hydroxypropan-2-yl, methoxymethyl, $C_{3-6}$cycloalkyl, $C_{1-4}$alkoxycarbonyl, $C_{1-4}$alkylcarbonyloxy-$C_{1-4}$alkyl, and trimethylsilyl;

1H-imidazol-1-yl optionally independently substituted with one to three $C_{1-3}$alkyl substituents;

and a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;

provided that a compound of Formula (I) is other than

N-[3-(4-chlorophenyl)-2-(2-methoxyphenyl)-2,4,5,6-tetrahydrocyclopenta[c]pyrazol-5-yl]-N,N',N'-trimethylsulfamide; or 3-(4-chlorophenyl)-2-(2-methoxyphenyl)-4',4',5',5'-tetramethyl-2,6-dihydro-4H-spiro[cyclopenta[c]pyrazole-5,2'-[1,3]dioxolane];

or an enantiomer, diastereomer, or pharmaceutically acceptable salt thereof.

2. The compound of claim 1 wherein $R^1$ is selected from the group consisting of $C_{1-4}$alkyl, $C_{1-4}$alkoxy, and trifluoromethoxy.

3. The compound of claim 2 wherein $R^1$ is selected from the group consisting of $C_{1-4}$alkoxy, and trifluoromethoxy.

4. The compound of claim 1 wherein $R^2$ is hydrogen.

5. The compound of claim 1 wherein $R^3$ is hydrogen or chloro.

6. The compound of claim 5 wherein $R^3$ is hydrogen.

7. The compound of claim 1 wherein $R^4$ is selected from the group consisting of $C_{1-4}$alkyl, $C_{1-4}$alkoxy, cyano, chloro, and di($C_{1-4}$alkyl)amino.

8. The compound of claim 1 wherein $R^6$ is chloro.

9. The compound of claim 1 wherein G is selected from the group consisting of $C_{1-6}$alkyl, hydroxy($C_{1-4}$)alkyl, $C_{1-6}$alkoxy, 2-methylprop-1-enyl, cyano, phenoxy, $C_{1-4}$alkoxycarbonyl, $C_{3-6}$cycloalkyl, 4,4-dimethyl-cyclohexyl, $C_{3-6}$cycloalkyl($C_{1-4}$)alkyl, $C_{3-6}$cycloalkyloxy, $C_{1-6}$alkylcarbonyloxy, di($C_{1-4}$alkyl)aminocarbonyloxy, di($C_{1-4}$alkyl)aminocarbonyloxy-$C_{1-4}$alkyl, $C_{1-4}$alkoxycarbonylamino-$C_{1-4}$alkyl, $C_{3-6}$cycloalkyl($C_{1-4}$)alkoxy, $C_{3-6}$cycloalkylcarbonyloxy, di($C_{1-4}$alkyl)aminosulfonyl-amino, di($C_{1-4}$alkyl)aminosulfonyl-(N-methyl)amino, $C_{1-4}$alkylsulfonyl-(N-methyl)amino, $C_{1-4}$alkylsulfonylamino, $C_{1-4}$alkylsulfonylamino-$C_{1-4}$alkyl, $C_{1-4}$alkylcarbonylamino-$C_{1-4}$alkyl, di($C_{1-4}$alkyl)aminocarbonylamino-$C_{1-4}$alkyl, trifluoromethylcarbonylamino, trifluoromethylcarbonylamino-$C_{1-4}$alkyl, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-$C_{1-4}$alkyl, 4-methyl-piperidin-1-yl, (1,2,4)-bicyclo[2.2.1]heptan-2-yloxy, tetrahydro-2H-pyran-4-yl($C_{1-4}$)alkoxy, 1,2,3,4-tetrahydroquinolin-3-yl, aminocarbonyl, pyridin-3-yl optionally substituted with one to two substituents each independently selected from the group consisting of $C_{1-4}$alkyl, $C_{1-4}$alkoxy, chloro, cyclopropyl, and $C_{1-4}$alkoxycarbonyl;

1H-1,2,3-triazol-1-yl optionally substituted with one to two substituents each independently selected from the group consisting of $C_{1-4}$alkyl, $C_{3-6}$cycloalkyl, $C_{1-4}$alkoxycarbonyl, $C_{1-4}$alkylcarbonyloxy-$C_{1-4}$alkyl, and trimethylsilyl;

1H-imidazol-1-yl optionally independently substituted with one to three $C_{1-3}$alkyl substituents;

and a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl.

10. The compound of claim 9 wherein G is selected from the group consisting of $C_{1-6}$alkyl, $C_{1-6}$alkoxy, $C_{1-4}$alkoxycarbonyl, $C_{3-6}$cycloalkyloxy, $C_{1-6}$alkylcarbonyloxy, di($C_{1-4}$alkyl)aminocarbonyloxy, di($C_{1-4}$alkyl)aminocarbonyloxy-$C_{1-4}$alkyl, $C_{1-4}$alkoxycarbonylamino-$C_{1-4}$alkyl, $C_{3-6}$cycloalkyl($C_{1-4}$)alkoxy, $C_{3-6}$cycloalkylcarbonyloxy, di($C_{1-4}$alkyl)aminosulfonyl-amino, di($C_{1-4}$alkyl)aminosulfonyl-(N-methyl)amino, $C_{1-4}$alkylsulfonyl-(N-methyl)amino, $C_{1-4}$alkylsulfonylamino, $C_{1-4}$alkylsulfonylamino-$C_{1-4}$alkyl, $C_{1-4}$alkylcarbonylamino-$C_{1-4}$alkyl, trifluoromethylcarbonylamino, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-$C_{1-4}$alkyl, 4-methyl-piperidin-1-yl, (1,2,4)-bicyclo[2.2.1]heptan-2-yloxy, tetrahydro-2H-pyran-4-yl($C_{1-4}$)alkoxy, pyridin-3-yl optionally substituted with a substituent independently selected from the group consisting of $C_{1-4}$alkyl, cyclopropyl, and $C_{1-4}$alkoxycarbonyl;

1H-1,2,3-triazol-1-yl optionally substituted with one to two substituents each independently selected from the group consisting of $C_{1-4}$alkyl, $C_{3-6}$cycloalkyl, $C_{1-4}$alkoxycarbonyl, and trimethylsilyl;

1H-imidazol-1-yl optionally independently substituted with one to three $C_{1-3}$alkyl substituents;

and
a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl.

11. The compound of Formula (I) as in claim 1

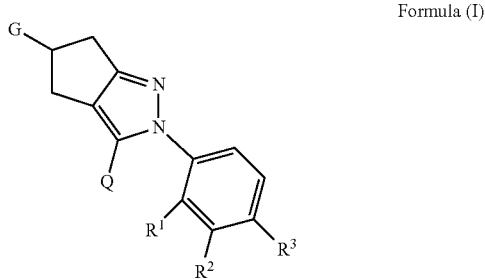

Formula (I)

wherein
$R^1$ is selected from the group consisting of $C_{1-4}$alkyl, $C_{1-4}$alkoxy, and trifluoromethoxy;
$R^2$ is hydrogen; or, $R^2$ may be taken with $R^1$ and the phenyl ring to which $R^1$ and $R^2$ are both attached to form 2,3-dihydrobenzofuran-7-yl;
$R^3$ is hydrogen or chloro;
Q is selected from the group consisting of Q1, Q2, and Q3;

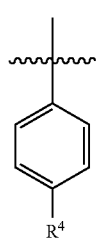

Q1

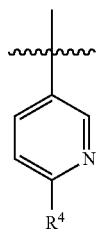

Q2

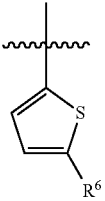

Q3 wherein
$R^4$ is selected from the group consisting of $C_{1-4}$alkyl, $C_{1-4}$alkoxy, cyano, chloro, and di($C_{1-4}$alkyl)amino;
$R^5$ and $R^6$ are each independently selected from the group consisting of $C_{1-4}$alkyl, $C_{1-4}$alkoxy, cyano, chloro, and di($C_{1-4}$alkyl)amino;

G is selected from the group consisting of $C_{1-6}$alkyl, hydroxy($C_{1-4}$)alkyl, $C_{1-6}$alkoxy, 2-methylprop-1-enyl, cyano, phenoxy, $C_{1-4}$alkoxycarbonyl, $C_{3-6}$cycloalkyl, 4,4-dimethyl-cyclohexyl, $C_{3-6}$cycloalkyl($C_{1-4}$)alkyl, $C_{3-6}$cycloalkyloxy, $C_{1-6}$alkylcarbonyloxy, di($C_{1-4}$alkyl)aminocarbonyloxy, di($C_{1-4}$alkyl)aminocarbonyloxy-$C_{1-4}$alkyl, $C_{1-4}$alkoxycarbonylamino-$C_{1-4}$alkyl, $C_{3-6}$cycloalkyl($C_{1-4}$)alkoxy, $C_{3-6}$cycloalkylcarbonyloxy, di($C_{1-4}$alkyl)aminosulfonyl-amino, di($C_{1-4}$alkyl)aminosulfonyl-(N-methyl)amino, $C_{1-4}$alkylsulfonyl-(N-methyl)amino, $C_{1-4}$alkylsulfonylamino, $C_{1-4}$alkylsulfonylamino-$C_{1-4}$alkyl, $C_{1-4}$alkylcarbonylamino-$C_{1-4}$alkyl, di($C_{1-4}$alkyl)aminocarbonylamino-$C_{1-4}$alkyl, trifluoromethylcarbonylamino, trifluoromethylcarbonylamino-$C_{1-4}$alkyl, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-$C_{1-4}$alkyl, 4-methyl-piperidin-1-yl, (1,2,4)-bicyclo[2.2.1]heptan-2-yloxy, tetrahydro-2H-pyran-4-yl($C_{1-4}$)alkoxy, 1,2,3,4-tetrahydroquinolin-3-yl, aminocarbonyl,
pyridin-3-yl optionally substituted with morpholin-4-yl or one to two substituents each independently selected from the group consisting of $C_{1-4}$alkyl, $C_{1-4}$alkoxy, chloro, cyclopropyl, and $C_{1-4}$alkoxycarbonyl;
1H-1,2,3-triazol-1-yl optionally substituted with one to two substituents each independently selected from the group consisting of $C_{1-4}$alkyl, $C_{3-6}$cycloalkyl, $C_{1-4}$alkoxycarbonyl, $C_{1-4}$alkylcarbonyloxy-$C_{1-4}$alkyl, and trimethylsilyl;
1H-imidazol-1-yl optionally independently substituted with one to three $C_{1-3}$alkyl substituents;
and
a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;
provided that a compound of Formula (I) is other than N-[3-(4-chlorophenyl)-2-(2-methoxyphenyl)-2,4,5,6-tetrahydrocyclopenta[c]pyrazol-5-yl]-N,N',N'-trimethylsulfamide; or
3-(4-chlorophenyl)-2-(2-methoxyphenyl)-4',4',5',5'-tetramethyl-2,6-dihydro-4H-spiro[cyclopenta[c]pyrazole-5,2'-[1,3]dioxolane];
or an enantiomer, diastereomer, or pharmaceutically acceptable salt thereof.

12. The compound of Formula (I) as in claim 1

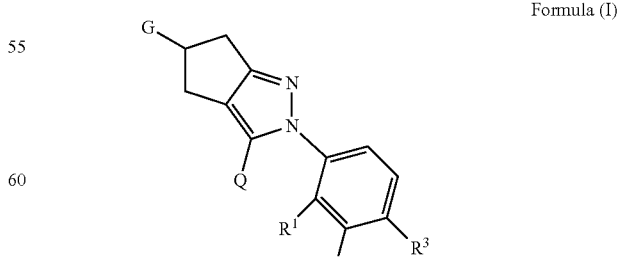

Formula (I)

wherein
$R^1$ is selected from the group consisting of $C_{1-4}$alkyl, $C_{1-4}$alkoxy, and trifluoromethoxy;

R² is hydrogen; or, R² may be taken with R¹ and the phenyl ring to which R¹ and R² are both attached to form 2,3-dihydrobenzofuran-7-yl;

R³ is hydrogen;

Q is selected from the group consisting of Q1, Q2, and Q3;

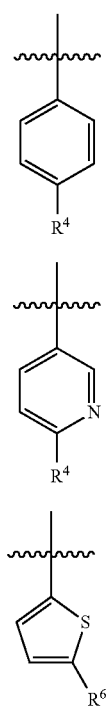

wherein

R⁴ is selected from the group consisting of $C_{1-4}$alkyl, $C_{1-4}$alkoxy, cyano, chloro, and di($C_{1-4}$alkyl)amino;

R⁵ is selected from the group consisting of $C_{1-4}$alkyl, $C_{1-4}$alkoxy, cyano, chloro, and di($C_{1-4}$alkyl)amino;

R⁶ is chloro;

G is selected from the group consisting of $C_{1-6}$alkyl, hydroxy($C_{1-4}$)alkyl, $C_{1-6}$alkoxy, 2-methylprop-1-enyl, cyano, phenoxy, $C_{1-4}$alkoxycarbonyl, $C_{3-6}$cycloalkyl, 4,4-dimethyl-cyclohexyl, $C_{3-6}$cycloalkyl($C_{1-4}$)alkyl, $C_{3-6}$cycloalkyloxy, $C_{1-6}$alkylcarbonyloxy, di($C_{1-4}$alkyl)aminocarbonyloxy, di($C_{1-4}$alkyl)aminocarbonyloxy-$C_{1-4}$alkyl, $C_{1-4}$alkoxycarbonylamino-$C_{1-4}$alkyl, $C_{3-6}$cycloalkyl($C_{1-4}$alkoxy, $C_{3-6}$cycloalkylcarbonyloxy, di($C_{1-4}$alkyl)aminosulfonyl-amino, di($C_{1-4}$alkyl)aminosulfonyl-(N-methyl)amino, $C_{1-4}$alkylsulfonyl-(N-methyl)amino, $C_{1-4}$alkylsulfonylamino, $C_{1-4}$alkylsulfonylamino-$C_{1-4}$alkyl, $C_{1-4}$-alkylcarbonylamino-$C_{1-4}$alkyl, di($C_{1-4}$alkyl)aminocarbonylamino-$C_{1-4}$alkyl, trifluoromethylcarbonylamino, trifluoromethylcarbonylamino-$C_{1-4}$alkyl, 2,5-dioxo-pyrrolidin-1-yl, 2-oxopyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-$C_{1-4}$alkyl, 4-methyl-piperidin-1-yl, (1,2,4)-bicyclo[2.2.1]heptan-2-yloxy, tetrahydro-2H-pyran-4-yl($C_{1-4}$)alkoxy, 1,2,3,4-tetrahydroquinolin-3-yl, aminocarbonyl, pyridin-3-yl optionally substituted with one to two substituents each independently selected from the group consisting of $C_{1-4}$alkyl, $C_{1-4}$alkoxy, chloro, cyclopropyl, and $C_{1-4}$alkoxycarbonyl;

1H-1,2,3-triazol-1-yl optionally substituted with one to two substituents each independently selected from the group consisting of $C_{1-4}$alkyl, $C_{3-6}$cycloalkyl, $C_{1-4}$alkoxycarbonyl, $C_{1-4}$alkylcarbonyloxy-$C_{1-4}$alkyl, and trimethylsilyl;

1H-imidazol-1-yl optionally independently substituted with one to three $C_{1-3}$alkyl substituents;

and a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;

provided that a compound of Formula (I) is other than

N-[3-(4-chlorophenyl)-2-(2-methoxyphenyl)-2,4,5,6-tetrahydrocyclopenta[c]pyrazol-5-yl]-N,N',N'-trimethylsulfamide; or 3-(4-chlorophenyl)-2-(2-methoxyphenyl)-4',4',5',5'-tetramethyl-2,6-dihydro-4H-spiro[cyclopenta[c]pyrazole-5,2'-[1,3]dioxolane];

or an enantiomer, diastereomer, or pharmaceutically acceptable salt thereof.

13. The compound of Formula (I) as in claim 1

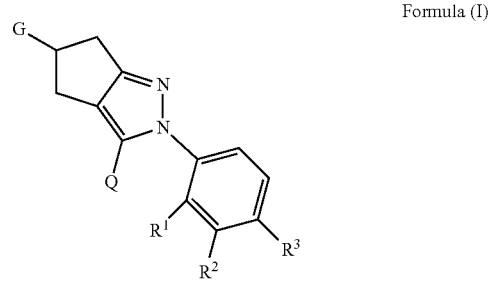

Formula (I)

wherein

R¹ is selected from the group consisting of $C_{1-4}$alkoxy and trifluoromethoxy;

R² is hydrogen;

R³ is hydrogen;

Q is selected from the group consisting of Q1, Q2, and Q3;

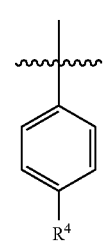

-continued

Q2
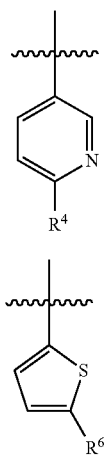

Q3
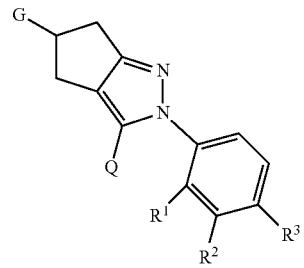

wherein
R⁴ is selected from the group consisting of $C_{1-4}$alkyl, $C_{1-4}$alkoxy, cyano, chloro, and di($C_{1-4}$alkyl)amino;
R⁵ is selected from the group consisting of $C_{1-4}$alkyl, $C_{1-4}$alkoxy, cyano, chloro, and di($C_{1-4}$alkyl)amino;
R⁶ is chloro;
G is selected from the group consisting of $C_{1-6}$alkyl, $C_{1-6}$alkoxy, $C_{1-6}$alkoxycarbonyl, $C_{3-6}$cycloalkyloxy, $C_{1-6}$alkylcarbonyloxy, di($C_{1-4}$alkyl)aminocarbonyloxy, di($C_{1-4}$alkyl)aminocarbonyloxy-$C_{1-4}$alkyl, $C_{1-4}$alkoxycarbonylamino-$C_{1-4}$alkyl, $C_{3-6}$cycloalkyl($C_{1-4}$)alkoxy, $C_{3-6}$cycloalkylcarbonyloxy, di($C_{1-4}$alkyl)aminosulfonyl-amino, di($C_{1-4}$alkyl)aminosulfonyl-(N-methyl)amino, $C_{1-4}$alkylsulfonyl-(N-methyl)amino, $C_{1-4}$alkylsulfonylamino, $C_{1-4}$alkylsulfonylamino-$C_{1-4}$alkyl, $C_{1-4}$alkylcarbonylamino-$C_{1-4}$alkyl, trifluoromethylcarbonylamino, 2,5-dioxo-pyrrolidin-1-yl, 2-oxo-pyrrolidin-1-yl, 3,3-difluoro-pyrrolidin-1-yl, 3,3-diethyl-pyrrolidin-1-yl, 3,3-dimethyl-pyrrolidin-1-yl, pyridinyloxy, trimethylsilyloxy, oxo, (tetrahydro-2H-pyran-2-yl)oxy, morpholin-4-yl, 2,6-dimethyl-morpholin-4-yl, morpholin-4-ylcarbonyloxy, morpholin-4-ylcarbonyloxy-$C_{1-4}$alkyl, 4-methyl-piperidin-1-yl, (1,2,4)-bicyclo[2.2.1]heptan-2-yloxy, tetrahydro-2H-pyran-4-yl($C_{1-4}$)alkoxy,
pyridin-3-yl optionally substituted with a substituent independently selected from the group consisting of $C_{1-4}$alkyl, cyclopropyl, and $C_{1-4}$alkoxycarbonyl;
1H-1,2,3-triazol-1-yl optionally substituted with one to two substituents each independently selected from the group consisting of $C_{1-4}$alkyl, $C_{3-6}$cycloalkyl, $C_{1-4}$alkoxycarbonyl, and trimethylsilyl;
1H-imidazol-1-yl optionally independently substituted with one to three $C_{1-3}$alkyl substituents;
and
a spirofused heterocyclyl independently selected from the group consisting of 4,4,5,5-tetramethyl-1,3-dioxolan-2-yl, 4,5-dimethyl-1,3-dioxolan-2-yl, 1,3-dioxan-2-yl, 4,6-dimethyl-1,3-dioxan-2-yl, (3a,6a)-tetrahydro-3aH-cyclopenta[d][1,3]dioxol-2-yl, 5,5-dimethyl-1,3-dioxan-2-yl, and (3a,7a)-hexahydrobenzo[d][1,3]dioxol-2-yl;
provided that a compound of Formula (I) is other than
N-[3-(4-chlorophenyl)-2-(2-methoxyphenyl)-2,4,5,6-tetrahydrocyclopenta[c]pyrazol-5-yl]-N,N',N'-trimethylsulfamide; or
3-(4-chlorophenyl)-2-(2-methoxyphenyl)-4',4',5',5'-tetramethyl-2,6-dihydro-4H-spiro[cyclopenta[c]pyrazole-5,2'-[1,3]dioxolane];
or an enantiomer, diastereomer, or pharmaceutically acceptable salt thereof.

14. The compound of Formula (I) as in claim 1

Formula (I)

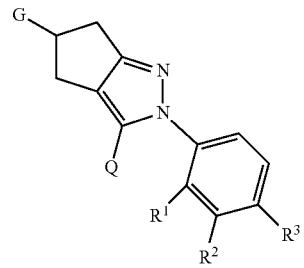

selected from the group consisting of
2-[3-(4-chlorophenyl)-2-(2-methoxyphenyl)-2,4,5,6-tetrahydrocyclopenta[c]pyrazol-5-yl]ethanol;
2-[3-(4-chlorophenyl)-2-(2-methoxyphenyl)-2,4,5,6-tetrahydrocyclopenta[c]pyrazol-5-yl]ethyl morpholine-4-carboxylate;
2-[3-(4-chlorophenyl)-2-(2-methoxyphenyl)-2,4,5,6-tetrahydrocyclopenta[c]pyrazol-5-yl]ethyl dimethylcarbamate;
3-(4-chlorophenyl)-2-(2-methoxyphenyl)-5-prop-2-en-1-yl-2,4,5,6-tetrahydrocyclopenta[c]pyrazole;
ethyl 3-(4-chlorophenyl)-2-(2-methoxyphenyl)-2,4,5,6-tetrahydrocyclopenta[c]pyrazole-5-carboxylate;
3-(4-chlorophenyl)-2-(2-methoxyphenyl)-2,4,5,6-tetrahydrocyclopenta[c]pyrazole-5-carboxamide;
N-{[2-(2-methoxyphenyl)-3-phenyl-2,4,5,6-tetrahydrocyclopenta[c]pyrazol-5-yl]methyl}methanesulfonamide;
N-{[3-(4-chlorophenyl)-2-(2-methoxyphenyl)-2,4,5,6-tetrahydrocyclopenta[c]pyrazol-5-yl]methyl}methanesulfonamide;
2-(2-methoxyphenyl)-3-phenyl-2,4,5,6-tetrahydrocyclopenta[c]pyrazole-5-carbonitrile;
3-(4-chlorophenyl)-2-(2-methoxyphenyl)-2,4,5,6-tetrahydrocyclopenta[c]pyrazole-5-carbonitrile;
N-{2-[3-(4-chlorophenyl)-2-(2-methoxyphenyl)-2,4,5,6-tetrahydrocyclopenta[c]pyrazol-5-yl]ethyl}methanesulfonamide;
N-{2-[3-(4-chlorophenyl)-2-(2-methoxyphenyl)-2,4,5,6-tetrahydrocyclopenta[c]pyrazol-5-yl]ethyl}acetamide;
tert-butyl{2-[3-(4-chlorophenyl)-2-(2-methoxyphenyl)-2,4,5,6-tetrahydrocyclopenta[c]pyrazol-5-yl]ethyl}carbamate;
ethyl 3-(4-chlorophenyl)-2-(2-ethylphenyl)-2,4,5,6-tetrahydrocyclopenta[c]pyrazole-5-carboxylate;
tert-butyl{[3-(4-chlorophenyl)-2-(2-ethylphenyl)-2,4,5,6-tetrahydrocyclopenta[c]pyrazol-5-yl]methylidene}carbamate;
tert-butyl{[3-(4-chlorophenyl)-2-(2-ethylphenyl)-2,4,5,6-tetrahydrocyclopenta[c]pyrazol-5-yl]methyl}carbamate;
[3-(4-chlorophenyl)-2-(2-ethylphenyl)-2,4,5,6-tetrahydrocyclopenta[c]pyrazol-5-yl]methyl diethylcarbamate;
N-{[3-(4-chlorophenyl)-2-(2-ethylphenyl)-2,4,5,6-tetrahydrocyclopenta[c]pyrazol-5-yl]methyl}methanesulfonamide;

N-{[3-(4-chlorophenyl)-2-(2-ethylphenyl)-2,4,5,6-tetrahydrocyclopenta[c]pyrazol-5-yl]methyl}-2,2,2-trifluoroacetamide;

tert-butyl (2-{3-(4-chlorophenyl)-2-[2-(trifluoromethyl)phenyl]-2,4,5,6-tetrahydrocyclopenta[c]pyrazol-5-yl}ethyl)carbamate;

N-(2-{3-(4-chlorophenyl)-2-[2-(trifluoromethyl)phenyl]-2,4,5,6-tetrahydrocyclopenta[c]pyrazol-5-yl}ethyl) methanesulfonamide;

3-(2-{3-(4-chlorophenyl)-2-[2-(trifluoromethyl)phenyl]-2,4,5,6-tetrahydrocyclopenta[c]pyrazol-5-yl}ethyl)-1,1-dimethylurea;

3-(4-chlorophenyl)-2-[2-(trifluoromethoxy)phenyl]-2,4,5,6-tetrahydrocyclopenta[c]pyrazol-5-yl dimethylcarbamate;

3-(4-chlorophenyl)-2-[2-(trifluoromethoxy)phenyl]-2,4,5,6-tetrahydrocyclopenta[c]pyrazol-5-ylmorpholine-4-carboxylate;

3-(4-chlorophenyl)-2-[2-(trifluoromethoxy)phenyl]-2,4,5,6-tetrahydrocyclopenta[c]pyrazol-5-ol;

3-(4-chlorophenyl)-2-(2-methoxyphenyl)-2,4,5,6-tetrahydrocyclopenta[c]pyrazol-5-ol;

3-(4-chlorophenyl)-2-[2-(trifluoromethyl)phenyl]-2,6-dihydrocyclopenta[c]pyrazol-5(4H)-one;

3-(4-chlorophenyl)-2-(2-methoxyphenyl)-2,4,5,6-tetrahydrocyclopenta[c]pyrazol-5-yl dimethylcarbamate;

3-(4-chlorophenyl)-2-(2-methoxyphenyl)-2,4,5,6-tetrahydrocyclopenta[c]pyrazol-5-yl morpholine-4-carboxylate;

3-(4-chlorophenyl)-2-(2-ethoxyphenyl)-2,4,5,6-tetrahydrocyclopenta[c]pyrazol-5-yl dimethylcarbamate;

3-(4-chlorophenyl)-2-(2-ethoxyphenyl)-2,4,5,6-tetrahydrocyclopenta[c]pyrazol-5-yl morpholine-4-carboxylate;

N-[3-(4-chlorophenyl)-2-(2-methoxyphenyl)-2,4,5,6-tetrahydrocyclopenta[c]pyrazol-5-yl]methanesulfonamide;

N-[3-(4-chlorophenyl)-2-(2-methoxyphenyl)-2,4,5,6-tetrahydrocyclopenta[c]pyrazol-5-yl]propane-2-sulfonamide;

N'-[3-(4-chlorophenyl)-2-(2-methoxyphenyl)-2,4,5,6-tetrahydrocyclopenta[c]pyrazol-5-yl]-N,N-dimethylsulfamide;

3-(4-chlorophenyl)-2-(2-methoxyphenyl)-2,6-dihydrocyclopenta[c]pyrazol-5(4H)-one;

3-(4-chlorophenyl)-2-(2-ethoxyphenyl)-2,6-dihydrocyclopenta[c]pyrazol-5(4H)-one;

N-[3-(4-chlorophenyl)-2-(2-methoxyphenyl)-2,4,5,6-tetrahydrocyclopenta[c]pyrazol-5-yl]-N-methylmethanesulfonamide;

1-[3-(4-chlorophenyl)-2-(2-ethoxyphenyl)-2,4,5,6-tetrahydrocyclopenta[c]pyrazol-5-yl]pyrrolidine-2,5-dione;

3-(4-chlorophenyl)-2-(2-ethoxyphenyl)-5-(1H-imidazol-1-yl)-2,4,5,6-tetrahydrocyclopenta[c]pyrazole;

1-[3-(4-chlorophenyl)-2-(2-ethoxyphenyl)-2,4,5,6-tetrahydrocyclopenta[c]pyrazol-5-yl]pyrrolidin-2-one;

3-(4-chlorophenyl)-2-(2-ethoxyphenyl)-5-[4-(trimethylsilyl)-1H-1,2,3-triazol-1-yl]-2,4,5,6-tetrahydrocyclopenta[c]pyrazole;

3-(4-chlorophenyl)-2-(2-ethoxyphenyl)-5-(1H-1,2,3-triazol-1-yl)-2,4,5,6-tetrahydrocyclopenta[c]pyrazole;

(5R)-3-(4-chlorophenyl)-2-(2-ethoxyphenyl)-5-(1H-imidazol-1-yl)-2,4,5,6-tetrahydrocyclopenta[c]pyrazole;

N-[(5R)-3-(4-chlorophenyl)-2-(2-ethoxyphenyl)-2,4,5,6-tetrahydrocyclopenta[c]pyrazol-5-yl]propane-2-sulfonamide;

N-[(5R)-3-(4-chlorophenyl)-2-(2-ethoxyphenyl)-2,4,5,6-tetrahydrocyclopenta[c]pyrazol-5-yl]-2,2,2-trifluoroacetamide;

N-[(5R)-3-(4-chlorophenyl)-2-(2-ethoxyphenyl)-2,4,5,6-tetrahydrocyclopenta[c]pyrazol-5-yl]-N,N',N'-trimethylsulfamide;

N'-[3-(4-chlorophenyl)-2-(2-ethoxyphenyl)-2,4,5,6-tetrahydrocyclopenta[c]pyrazol-5-yl]-N,N-dimethylsulfamide;

N-[3-(4-chlorophenyl)-2-(2-ethoxyphenyl)-2,4,5,6-tetrahydrocyclopenta[c]pyrazol-5-yl]-N,N',N'-trimethylsulfamide;

(5R)-3-(4-chlorophenyl)-5-methoxy-2-(2-methoxyphenyl)-2,4,5,6-tetrahydrocyclopenta[c]pyrazole;

N-[(5S)-3-(4-chlorophenyl)-2-(2,3-dihydro-1-benzofuran-7-yl)-2,4,5,6-tetrahydrocyclopenta[c]pyrazol-5-yl]-N,N',N'-trimethylsulfamide;

N-[(5S)-3-(4-chlorophenyl)-2-(2,3-dihydro-1-benzofuran-7-yl)-2,4,5,6-tetrahydrocyclopenta[c]pyrazol-5-yl]-N-methylpropane-2-sulfonamide;

2-(4-Chloro-2-methoxyphenyl)-3-(4-chlorophenyl)-2,6-dihydro-4H-spiro[cyclopenta[c]pyrazole-5,2'-[1,3]dioxane];

(5Z)-3-(4-chlorophenyl)-2-(2-methoxyphenyl)-2,6-dihydrocyclopenta[c]pyrazol-5(4H)-one oxime;

3-(4-chlorophenyl)-2-(2-methoxyphenyl)-2,6-dihydro-4H-spiro[cyclopenta[c]pyrazole-5,2'-[1,3]dioxane];

(5R)-3-(4-chlorophenyl)-2-(2-methoxyphenyl)-2,4,5,6-tetrahydrocyclopenta[c]pyrazol-5-yl 2-ethylbutanoate;

N-[(5R)-2-(2-Methoxyphenyl)-3-(6-methoxypyridin-3-yl)-2,4,5,6-tetrahydrocyclopenta[c]pyrazol-5-yl]-N,N',N'-trimethylsulfamide;

N-{(5R)-2-(2-Methoxyphenyl)-3-[6-(1-methylethoxy)pyridin-3-yl]-2,4,5,6-tetrahydrocyclopenta[c]pyrazol-5-yl}-N,N',N'-trimethylsulfamide;

(5S)-3-(4-chlorophenyl)-2-(2-methoxyphenyl)-5-phenoxy-2,4,5,6-tetrahydrocyclopenta[c]pyrazole;

(5S)-3-(4-chlorophenyl)-2-(2-methoxyphenyl)-5-(pyridin-3-yloxy)-2,4,5,6-tetrahydrocyclopenta[c]pyrazole;

3-(4-chlorophenyl)-2-(2-methoxyphenyl)-5-[6-(1-methylethoxy)pyridin-3-yl]-2,4,5,6-tetrahydrocyclopenta[c]pyrazole;

(5R)-3-(4-chlorophenyl)-2-(2-methoxyphenyl)-5-(pyridin-2-yloxy)-2,4,5,6-tetrahydrocyclopenta[c]pyrazole;

3-(4-chlorophenyl)-2-(2-methoxyphenyl)-5-(6-morpholin-4-ylpyridin-3-yl)-2,4,5,6-tetrahydrocyclopenta[c]pyrazole;

3-(4-chlorophenyl)-2-(2-methoxyphenyl)-5-pyridin-3-yl-2,4,5,6-tetrahydrocyclopenta[c]pyrazole;

3-(4-chlorophenyl)-5-(4,4-dimethylcyclohexyl)-2-(2-methoxyphenyl)-2,4,5,6-tetrahydrocyclopenta[c]pyrazole;

3-[3-(4-chlorophenyl)-2-(2-methoxyphenyl)-2,4,5,6-tetrahydrocyclopenta[c]pyrazol-5-yl]-1,2,3,4-tetrahydroquinoline;

Ethyl 5-[3-(4-chlorophenyl)-2-(2-methoxyphenyl)-2,4,5,6-tetrahydrocyclopenta[c]pyrazol-5-yl]pyridine-3-carboxylate;

(5S)-3-(4-chlorophenyl)-2-(2-methoxyphenyl)-5-(1-methylethoxy)-2,4,5,6-tetrahydrocyclopenta[c]pyrazole;

3-(4-chlorophenyl)-2-(2-methoxyphenyl)-5-morpholin-4-yl-2,4,5,6-tetrahydrocyclopenta[c]pyrazole;

(5S)-3-(4-chlorophenyl)-2-(2-methoxyphenyl)-5-[(trimethylsilyl)oxy]-2,4,5,6-tetrahydrocyclopenta[c]pyrazole;

(5S)-3-(4-chlorophenyl)-2-(2-methoxyphenyl)-2,4,5,6-tetrahydrocyclopenta[c]pyrazol-5-yl 2-ethylbutanoate;

3-(4-chlorophenyl)-2-(2-methoxyphenyl)-5',5'-dimethyl-2,6-dihydro-4H-spiro[cyclopenta[c]pyrazole-5,2'-[1,3]dioxane];

(5S)-3-(4-chlorophenyl)-5-(2-ethylbutoxy)-2-(2-methoxyphenyl)-2,4,5,6-tetrahydrocyclopenta[c]pyrazole;

3-(4-chlorophenyl)-2-(2-methoxyphenyl)-5-(6-methylpyridin-3-yl)-2,4,5,6-tetrahydrocyclopenta[c]pyrazole;

3-(4-chlorophenyl)-5-(6-ethoxypyridin-3-yl)-2-(2-methoxyphenyl)-2,4,5,6-tetrahydrocyclopenta[c]pyrazole;

5-[2-Chloro-6-(1-methylethyl)pyridin-3-yl]-3-(4-chlorophenyl)-2-(2-methoxyphenyl)-2,4,5,6-tetrahydrocyclopenta[c]pyrazole;

(5S)-3-(4-chlorophenyl)-2-(2-methoxyphenyl)-5-(tetrahydro-2H-pyran-2-yloxy)-2,4,5,6-tetrahydrocyclopenta[c]pyrazole 3-(4-chlorophenyl)-5-(6-cyclopropylpyridin-3-yl)-2-(2-methoxyphenyl)-2,4,5,6-tetrahydrocyclopenta[c]pyrazole;

(5S)-3-(4-chlorophenyl)-2-(2-methoxyphenyl)-2,4,5,6-tetrahydrocyclopenta[c]pyrazol-5-yl cyclohexanecarboxylate;

(5S)-3-(4-chlorophenyl)-2-(2-methoxyphenyl)-2,4,5,6-tetrahydrocyclopenta[c]pyrazol-5-yl cyclopentanecarboxylate;

(5S)-3-(4-chlorophenyl)-2-(2-methoxyphenyl)-2,4,5,6-tetrahydrocyclopenta[c]pyrazol-5-yl cyclobutanecarboxylate;

(5S)-3-(4-chlorophenyl)-2-(2-methoxyphenyl)-2,4,5,6-tetrahydrocyclopenta[c]pyrazol-5-yl 2-methylpropanoate;

(5S)-3-(4-chlorophenyl)-5-(cyclohexylmethoxy)-2-(2-methoxyphenyl)-2,4,5,6-tetrahydrocyclopenta[c]pyrazole;

(5S)-3-(4-chlorophenyl)-5-(cyclopentylmethoxy)-2-(2-methoxyphenyl)-2,4,5,6-tetrahydrocyclopenta[c]pyrazole;

(5S)-3-(4-chlorophenyl)-5-(cyclobutylmethoxy)-2-(2-methoxyphenyl)-2,4,5,6-tetrahydrocyclopenta[c]pyrazole;

(5S)-3-(4-chlorophenyl)-2-(2-methoxyphenyl)-5-(2-methylpropoxy)-2,4,5,6-tetrahydrocyclopenta[c]pyrazole;

(5S)-3-(4-chlorophenyl)-2-(2-methoxyphenyl)-2,4,5,6-tetrahydrocyclopenta[c]pyrazol-5-yl tetrahydro-2H-pyran-4-carboxylate;

(5S)-3-(4-chlorophenyl)-2-(2-methoxyphenyl)-5-(tetrahydro-2H-pyran-4-ylmethoxy)-2,4,5,6-tetrahydrocyclopenta[c]pyrazole;

(5S)-3-(4-chlorophenyl)-5-(cyclohexyloxy)-2-(2-methoxyphenyl)-2,4,5,6-tetrahydrocyclopenta[c]pyrazole;

(5S)-5-[(1S,2S,4R)-bicyclo[2.2.1]hept-2-yloxy]-3-(4-chlorophenyl)-2-(2-methoxyphenyl)-2,4,5,6-tetrahydrocyclopenta[c]pyrazole;

(5S)-3-(4-chlorophenyl)-5-(cyclopentyloxy)-2-(2-methoxyphenyl)-2,4,5,6-tetrahydrocyclopenta[c]pyrazole;

4-[2-(2-methoxyphenyl)-5',5'-dimethyl-2,6-dihydro-4H-spiro[cyclopenta[c]pyrazole-5,2'-[1,3]dioxan-3-yl]benzonitrile;

3-(4-chlorophenyl)-2-(2-methoxyphenyl)-5-(1-methylethyl)-2,4,5,6-tetrahydrocyclopenta[c]pyrazole;

4-[2-(2-methoxyphenyl)-5',5'-dimethyl-2,6-dihydro-4H-spiro[cyclopenta[c]pyrazole-5,2'-[1,3]dioxan-3-yl]-N,N-dimethylaniline;

3-(6-ethoxypyridin-3-yl)-2-(2-methoxyphenyl)-5',5'-dimethyl-2,6-dihydro-4H-spiro[cyclopenta[c]pyrazole-5,2'-[1,3]dioxane];

2-(2-methoxyphenyl)-5',5'-dimethyl-3-(6-methylpyridin-3-yl)-2,6-dihydro-4H-spiro[cyclopenta[c]pyrazole-5,2'-[1,3]dioxane];

2-(2-methoxyphenyl)-3-(6-methoxypyridin-3-yl)-5',5'-dimethyl-2,6-dihydro-4H-spiro[cyclopenta[c]pyrazole-5,2'-[1,3]dioxane];

5-[2-(2-methoxyphenyl)-5',5'-dimethyl-2,6-dihydro-4H-spiro[cyclopenta[c]pyrazole-5,2'-[1,3]dioxan]-3-yl]-N,N-dimethylpyridin-2-amine;

(4'R,5'R)-3-(4-chlorophenyl)-2-(2-methoxyphenyl)-4',5'-dimethyl-2,6-dihydro-4H-spiro[cyclopenta[c]pyrazole-5,2'-[1,3]dioxolane];

(4'S,5'S)-3-(4-chlorophenyl)-2-(2-methoxyphenyl)-4',5'-dimethyl-2,6-dihydro-4H-spiro[cyclopenta[c]pyrazole-5,2'-[1,3]dioxolane];

(4'R,6'R)-3-(4-chlorophenyl)-2-(2-methoxyphenyl)-4',6'-dimethyl-2,6-dihydro-4H-spiro[cyclopenta[c]pyrazole-5,2'-[1,3]dioxane];

(4'S,6'S)-3-(4-chlorophenyl)-2-(2-methoxyphenyl)-4',6'-dimethyl-2,6-dihydro-4H-spiro[cyclopenta[c]pyrazole-5,2'-[1,3]dioxane];

(4'R,5'S)-3-(4-chlorophenyl)-2-(2-methoxyphenyl)-4',5'-dimethyl-2,6-dihydro-4H-spiro[cyclopenta[c]pyrazole-5,2'-[1,3]dioxolane];

(4'R,5'S)-3-(4-chlorophenyl)-2-(2-methoxyphenyl)-4',5'-dimethyl-2,6-dihydro-4H-spiro[cyclopenta[c]pyrazole-5,2'-[1,3]dioxolane];

3-(4-chlorophenyl)-5-cyclohexyl-2-(2-methoxyphenyl)-2,4,5,6-tetrahydrocyclopenta[c]pyrazole;

4-[2-(2-methoxyphenyl)-5-(2-methylpropyl)-2,4,5,6-tetrahydrocyclopenta[c]pyrazol-3-yl]benzonitrile;

4-[5-(cyclohexylmethyl)-2-(2-methoxyphenyl)-2,4,5,6-tetrahydrocyclopenta[c]pyrazol-3-yl]benzonitrile;

4-[2-(2-methoxyphenyl)-4',4',5',5'-tetramethyl-2,6-dihydro-4H-spiro[cyclopenta[c]pyrazole-5,2'-[1,3]dioxolan]-3-yl]-N,N-dimethylaniline;

3-(6-ethoxypyridin-3-yl)-2-(2-methoxyphenyl)-4',4',5',5'-tetramethyl-2,6-dihydro-4H-spiro[cyclopenta[c]pyrazole-5,2'-[1,3]dioxolane];

2-(2-methoxyphenyl)-4',4',5',5'-tetramethyl-3-(6-methylpyridin-3-yl)-2,6-dihydro-4H-spiro[cyclopenta[c]pyrazole-5,2'-[1,3]dioxolane];

5-[2-(2-methoxyphenyl)-4',4',5',5'-tetramethyl-2,6-dihydro-4H-spiro[cyclopenta[c]pyrazole-5,2'-[1,3]dioxolan]-3-yl]-N,N-dimethylpyridin-2-amine;

4-[2-(2-methoxyphenyl)-4',4',5',5'-tetramethyl-2,6-dihydro-4H-spiro[cyclopenta[c]pyrazole-5,2'-[1,3]dioxolan]-3-yl]benzonitrile;

(3aR,7aS)-3'-(4-chlorophenyl)-2'-(2-methoxyphenyl)-2',3a,4,5,6,6',7,7a-octahydro-4'H-spiro[1,3-benzodioxole-2,5'-cyclopenta[c]pyrazole];

(3aS,6aS)-3'-(4-chlorophenyl)-2'-(2-methoxyphenyl)-2',4,5,6,6',6a-hexahydro-3aH,4'H-spiro[cyclopenta[d][1,3]dioxole-2,5'-cyclopenta[c]pyrazole];

(3aR,6aS)-3'-(4-chlorophenyl)-2'-(2-methoxyphenyl)-2',4,5,6,6',6a-hexahydro-3aH,4'H-spiro[cyclopenta[d][1,3]dioxole-2,5'-cyclopenta[c]pyrazole];

(3aR,6aS)-3'-(4-chlorophenyl)-2'-(2-methoxyphenyl)-2',4,5,6,6',6a-hexahydro-3aH,4'H-spiro[cyclopenta[d][1,3]dioxole-2,5'-cyclopenta[c]pyrazole];

3-(4-chlorophenyl)-5-(2,6-dimethylmorpholin-4-yl)-2-(2-methoxyphenyl)-2,4,5,6-tetrahydrocyclopenta[c]pyrazole;

3-(4-chlorophenyl)-2-(2-methoxyphenyl)-5-(4-methylpiperidin-1-yl)-2,4,5,6-tetrahydrocyclopenta[c]pyrazole;

3-(4-chlorophenyl)-5-(3,3-diethylpyrrolidin-1-yl)-2-(2-methoxyphenyl)-2,4,5,6-tetrahydrocyclopenta[c]pyrazole;

3-(4-chlorophenyl)-5-(3,3-dimethylpyrrolidin-1-yl)-2-(2-methoxyphenyl)-2,4,5,6-tetrahydrocyclopenta[c]pyrazole;

3-(5-chlorothiophen-2-yl)-2-(2-methoxyphenyl)-5',5'-dimethyl-2,6-dihydro-4H-spiro[cyclopenta[c]pyrazole-5,2'-[1,3]dioxane];

3-(5-chlorothiophen-2-yl)-2-(2-methoxyphenyl)-4',4',5',5'-tetramethyl-2,6-dihydro-4H-spiro[cyclopenta[c]pyrazole-5,2'-[1,3]dioxolane];

3-(4-chlorophenyl)-2-(2-methoxyphenyl)-5-pyrrolidin-1-yl-2,4,5,6-tetrahydrocyclopenta[c]pyrazole;

3-(4-chlorophenyl)-5-(3,3-difluoropyrrolidin-1-yl)-2-(2-methoxyphenyl)-2,4,5,6-tetrahydrocyclopenta[c]pyrazole;

4-[(5S)-5-(4-cyclopentyl-1H-1,2,3-triazol-1-yl)-2-(2-methoxyphenyl)-2,4,5,6-tetrahydrocyclopenta[c]pyrazol-3-yl]benzonitrile;

methyl 1-[(5S)-3-(4-cyanophenyl)-2-(2-methoxyphenyl)-2,4,5,6-tetrahydrocyclopenta[c]pyrazol-5-yl]-1H-1,2,3-triazole-4-carboxylate;

4-[(5S)-5-[4-(1-hydroxy-1-methylethyl)-1H-1,2,3-triazol-1-yl]-2-(2-methoxyphenyl)-2,4,5,6-tetrahydrocyclopenta[c]pyrazol-3-yl]benzonitrile;

4-{(5S)-2-(2-methoxyphenyl)-5-[4-(2-methylpropyl)-1H-1,2,3-triazol-1-yl]-2,4,5,6-tetrahydrocyclopenta[c]pyrazol-3-yl}benzonitrile;

{1-[(5S)-3-(4-cyanophenyl)-2-(2-methoxyphenyl)-2,4,5,6-tetrahydrocyclopenta[c]pyrazol-5-yl]-1H-1,2,3-triazol-4-yl}methyl acetate;

4-[(5S)-5-[4-(methoxymethyl)-1H-1,2,3-triazol-1-yl]-2-(2-methoxyphenyl)-2,4,5,6-tetrahydrocyclopenta[c]pyrazol-3-yl]benzonitrile;

4-[(5S)-5-(4-tert-butyl-1H-1,2,3-triazol-1-yl)-2-(2-methoxyphenyl)-2,4,5,6-tetrahydrocyclopenta[c]pyrazol-3-yl]benzonitrile;

4-[(5S)-5-(4,5-dimethyl-1H-imidazol-1-yl)-2-(2-methoxyphenyl)-2,4,5,6-tetrahydrocyclopenta[c]pyrazol-3-yl]benzonitrile;

4-[(5S)-2-(2-methoxyphenyl)-5-(2,4,5-trimethyl-1H-imidazol-1-yl)-2,4,5,6-tetrahydrocyclopenta[c]pyrazol-3-yl]benzonitrile;

4-[(5S)-5-(2-ethyl-4,5-dimethyl-1H-imidazol-1-yl)-2-(2-methoxyphenyl)-2,4,5,6-tetrahydrocyclopenta[c]pyrazol-3-yl]benzonitrile;

4-[(5S)-5-(2-ethyl-1H-imidazol-1-yl)-2-(2-methoxyphenyl)-2,4,5,6-tetrahydrocyclopenta[c]pyrazol-3-yl]benzonitrile;

4-[(5S)-2-(2-methoxyphenyl)-5-(2-methyl-1H-imidazol-1-yl)-2,4,5,6-tetrahydrocyclopenta[c]pyrazol-3-yl]benzonitrile;

4-[(5S)-5-(4,5-diethyl-1H-1,2,3-triazol-1-yl)-2-(2-methoxyphenyl)-2,4,5,6-tetrahydrocyclopenta[c]pyrazol-3-yl]benzonitrile;

4-[(5S)-2-(2-methoxyphenyl)-5-(2,4,5-triethyl-1H-imidazol-1-yl)-2,4,5,6-tetrahydrocyclopenta[c]pyrazol-3-yl]benzonitrile;

4-[(5S)-5-(4,5-diethyl-2-methyl-1H-imidazol-1-yl)-2-(2-methoxyphenyl)-2,4,5,6-tetrahydrocyclopenta[c]pyrazol-3-yl]benzonitrile;

4-[(5S)-5-(4,5-diethyl-1H-imidazol-1-yl)-2-(2-methoxyphenyl)-2,4,5,6-tetrahydrocyclopenta[c]pyrazol-3-yl] benzonitrile;

or a pharmaceutically acceptable salt form thereof.

15. A pharmaceutical composition comprising a compound of claim 1 or 14 and at least one of a pharmaceutically acceptable carrier, a pharmaceutically acceptable excipient, and a pharmaceutically acceptable diluent.

16. The pharmaceutical composition of claim 15, wherein the composition is a solid oral dosage form.

17. The pharmaceutical composition of claim 15, wherein the composition is a syrup, an elixir or a suspension.

18. A method for treating inflammatory pain in a subject in need thereof comprising administering to the subject a therapeutically effective amount of a compound of claim 1 or 14.

19. The method of claim 18 wherein the inflammatory pain is due to inflammatory bowel disease, irritable bowel syndrome, visceral pain, migraine, post-operative pain, osteoarthritis, rheumatoid arthritis, back pain, lower back pain, joint pain, abdominal pain, chest pain, labor pain, musculoskeletal diseases, skin diseases, toothache, pyresis, burn, sunburn, snake bite, venomous snake bite, spider bite, insect sting, neurogenic/overactive bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache or arachnoiditis.

20. A method for treating neuropathic pain in a subject in need thereof comprising administering to the subject a therapeutically effective amount of a compound of claim 1 or 14.

21. The method of claim 20, wherein the neuropathic pain is caused by cancer pain, neurological disorders, spine and peripheral nerve surgery, brain tumor, traumatic brain injury (TBI), chemotherapy-induced pain, pain chronification, radicular pain, HIV pain, spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

* * * * *